United States Patent
Cole et al.

(10) Patent No.: US 7,820,825 B2
(45) Date of Patent: Oct. 26, 2010

(54) N-SUBSTITUTED-AZACYCLYLAMINES AS HISTAMINE-3 ANTAGONISTS

(75) Inventors: Derek Cecil Cole, New City, NY (US); Magda Asselin, Mahwah, NJ (US); Joseph Raymond Stock, Monroe, NY (US); Albert Jean Robichaud, Ringoes, NJ (US); Ji-In Kim, Princeton, NJ (US); William Ronald Solvibile, East Windsor, NJ (US); Jonathan Laird Gross, Cranbury, NJ (US)

(73) Assignee: Wyeth LLC, Madison, NJ (US)

( * ) Notice: Subject to any disclaimer, the term of this patent is extended or adjusted under 35 U.S.C. 154(b) by 499 days.

(21) Appl. No.: 11/724,078

(22) Filed: Mar. 14, 2007

(65) Prior Publication Data
US 2007/0219240 A1 Sep. 20, 2007

Related U.S. Application Data

(60) Provisional application No. 60/782,513, filed on Mar. 15, 2006, provisional application No. 60/859,079, filed on Nov. 15, 2006.

(51) Int. Cl.
- A61K 31/41 (2006.01)
- A61K 31/415 (2006.01)
- C07D 207/00 (2006.01)
- C07D 233/00 (2006.01)
- C07D 249/00 (2006.01)

(52) U.S. Cl. ............ 546/249; 548/250; 548/255; 548/262.2; 548/300.1; 548/400

(58) Field of Classification Search .............. 546/249; 548/250, 262.2, 255, 300.1, 400
See application file for complete search history.

(56) References Cited

U.S. PATENT DOCUMENTS

| | | | |
|---|---|---|---|
| 3,933,829 A | 1/1976 | Archibald et al. | |
| 4,159,331 A | 6/1979 | McCall | |
| 4,166,853 A | 9/1979 | McCall | |
| 5,294,631 A | 3/1994 | Franz et al. | |
| 5,883,096 A | 3/1999 | Lowe et al. | |
| 6,034,093 A * | 3/2000 | Ewing et al. | 514/301 |
| 6,541,499 B1 | 4/2003 | Bastian et al. | |
| 6,699,873 B1 * | 3/2004 | Maguire et al. | 514/256 |
| 2004/0082779 A1 | 4/2004 | Vos et al. | |
| 2005/0256102 A1 | 11/2005 | Claiborne et al. | |
| 2006/0014733 A1 | 1/2006 | Howard, Jr. et al. | |
| 2006/0089496 A1 | 4/2006 | Lam et al. | |
| 2006/0166960 A1 | 7/2006 | Aslanian et al. | |
| 2007/0004713 A1 | 1/2007 | Barlaam et al. | |
| 2007/0032475 A1 | 2/2007 | Ye et al. | |
| 2007/0270440 A1 * | 11/2007 | Cole et al. | 514/260.1 |
| 2008/0119458 A1 * | 5/2008 | Solvibile et al. | 514/217.08 |

FOREIGN PATENT DOCUMENTS

| | | |
|---|---|---|
| GB | 1416872 | 12/1975 |
| WO | WO 94/22826 | 10/1994 |
| WO | WO 98/48800 | 11/1998 |
| WO | WO 01/42224 A1 | 6/2001 |
| WO | WO 01/74773 A2 | 10/2001 |
| WO | WO 03/004467 A2 | 1/2003 |
| WO | WO 03/082272 A1 | 10/2003 |
| WO | WO 2004/081011 A1 | 9/2004 |
| WO | WO 2005/115977 A1 | 12/2005 |
| WO | WO 2006/011042 A1 | 2/2006 |
| WO | WO 2006/019833 A1 | 2/2006 |
| WO | WO 2006/023462 A1 | 3/2006 |
| WO | WO 2006/028269 A2 | 3/2006 |
| WO | WO 2006/040281 A1 | 4/2006 |
| WO | WO 2007/107539 A1 | 9/2007 |
| WO | WO 2007/108936 A | 9/2007 |
| WO | WO 2007/115933 A1 | 10/2007 |
| WO | WO 2008/045371 A | 4/2008 |

OTHER PUBLICATIONS

Patani et al., Chem Rev, 1996, vol. 96 (8), pp. 3147-3176, especially p. 3148.*

Blandina, P. et al., "Inhibition of cortical acetylcholine release and cognitive performance by histamine H3 receptor activation in rats", Br J Pharmacol. Dec. 1996;119(8):1656-64.

Database Chemcats [Online] chemical abstract service. Ambinter Stock Screening Collection; Feb. 13, 2008.

Esbenshade et al., "Histamine H3 receptor antagonists: preclinical promise for treating obesity and cognitive disorders". Mol Interv. Apr. 2006;6(2):77-88.

Fox, G. B. et al., "Effects of histamine H(3) receptor ligands GT-2331 and ciproxifan in a repeated acquisition avoidance response in the spontaneously hypertensive rat pup", Behav Brain Res. Apr. 1, 2002;131(1-2):151-61.

Hancock et al., Perspectives on cognitive domains, H3 receptor ligands and neurological disease. Expert Opin Investig Drugs. Oct. 2004;13(10):1237-48.

Koh et al. "Conformational and structural features determining in vitro antimalarial activity in some indolo 3, 2-couinolines, anilinoquinolines and tetrahydroindolo3, 2-dbenzazepines". European Journal of Medicinal Chemistry. vol. 29, No. 2, 1994, p. 107-113.

(Continued)

Primary Examiner—Susannah Chung
(74) Attorney, Agent, or Firm—Gregg C. Benson; Robert T. Ronau

(57) ABSTRACT

The present invention provides a compound of formula I and the use thereof for the treatment of a central nervous system disorder related to or affected by the histamine-3 receptor.

(I)

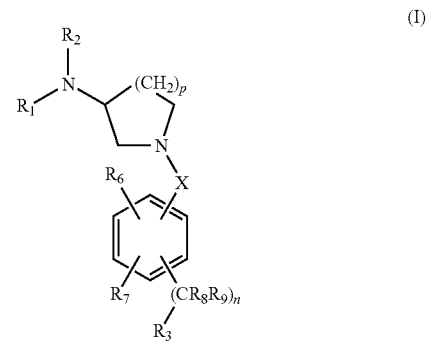

11 Claims, No Drawings

OTHER PUBLICATIONS

Komater, V.A., et al., "H3 receptor blockade by thioperamide enhances cognition in rats without inducing locomotor sensitization", Psychopharmacology (Berl). Jun. 2003;167(4):363-72.

Meguro, K. et al., "Effects of thioperamide, a histamine H3 antagonist, on the step-through passive avoidance response and histidine decarboxylase activity in senescence-accelerated mice", Pharmacol Biochem Behav. Mar. 1995;50(3):321-5.

Miyazaki, S. et al., "Effects of clobenpropit (VUF-9153), a histamine H3-receptor antagonist, on learning and memory, and on cholinergic and monoaminergic systems in mice", Life Sci. 1997;61(4):355-61.

PCT International Search Report, Written Opinion of the International Searching Authority for corresponding PCT/US2007/005776, International filing date Mar. 8, 2007.

Prast, H. et al., "Histaminergic neurons facilitate social memory in rats", Brain Res. Sep. 23, 1996;734(1-2):316-8.

\* cited by examiner

N-SUBSTITUTED-AZACYCLYLAMINES AS HISTAMINE-3 ANTAGONISTS

This application claims the benefit under 35 U.S.C. §119 (e) to co-pending U.S. provisional application No. 60/782,513, filed Mar. 15, 2006 and U.S. provisional application No. 60/859,079, filed Nov. 15, 2006, each of which is hereby incorporated by reference in its entirety.

BACKGROUND OF THE INVENTION

The histamine-3 (H3) receptor is one of four histamine receptor subtypes (H1-H4), all of which are members of the larger G-protein-coupled receptor (GPCR) superfamily of receptors. The H3 receptor is predominantly expressed in the central nervous system. In the brain, it is located in regions associated with learning and memory such as the cerebral cortex, hippocampus and striatum. The H3 receptor acts as both auto- and hetero-receptor to regulate the release of histamine and other neurotransmitters. Within the cortex, the H3 receptor appears to directly modify GABA release from cortical interneurons. Antagonism of the H3 receptor produces a decrease in GABA-release and disinhibition of the cortical cholinergic system, resulting in increased acetylcholine levels (Bacciottini, L. et al, Behavioral Brain Research, 124, 2001, 183-194). In addition to direct regulation of cholinergic neurotransmission, the H3 receptor has been shown to modulate the release of dopamine, serotonin and norepinephrine (Leurs, R., et al, Trends in Pharmacological Sciences, 19, 1998, 177-183). A postmortem study in humans suggests that a decrease in brain histamine levels may contribute to the cognitive decline that occurs in Alzheimer's disease, directly or through the cholinergic system (Panula, P., et al, Neuroscience, 82, 1998, 993-997). H3 agonists have been reported to impair memory in various tasks, such as object recognition, passive avoidance (Blandina, P., et al, British Journal of Pharmacology, 119(8), 1996, 1656-1664) and social olfactory memory (Prast, H., et al, 734, 1996, 316-318), whereas H3 antagonists have been reported to rescue impairments produced pharmacologically or genetically, i.e. Miyazaki, S., et al, Life Sciences, 61, 1997, 355-361; Meguro, K., et al, Pharmacology, Biochemistry and Behavior, 50, 1995, 321-325; Fox, G. B., et. al, Beharioral Brain Research, 131, 2002, 151-161; and Komater, V. A., et al, Psychopharmacology, 167, 2003, 363-372.

Accumulating neuroanatomical, neurochemical, pharmacological and behavioral data support the concept that H3 receptor antagonists may improve cognitive performance in disease states such as mild cognitive impairment and Alzheimer's disease and may have therapeutic value in the treatment of attention deficit hyperactivity disorder (ADHD), schizophrenia, obesity and sleep disorders.

Therefore, it is an object of this invention to provide compounds which are inhibitors of the H3 receptor and are useful as therapeutic agents in the treatment of a variety of central nervous system disorders related to or affected by the H3 receptor.

It is another object of this invention to provide therapeutic methods and pharmaceutical compositions useful for the treatment of central nervous system disorders related to or affected by the H3 receptor.

It is a feature of this invention that the compounds provided may also be useful to further study and elucidate the H3 receptor.

SUMMARY OF THE INVENTION

The present invention provides an N-substituted-azacyclylamine compound of formula I

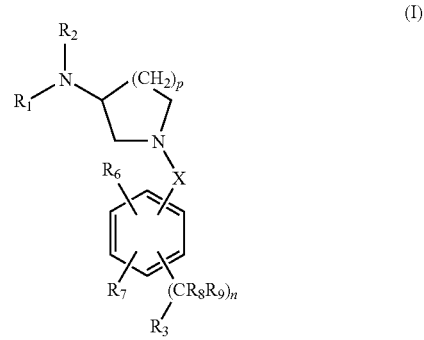

wherein
X is CO, $CH_2$ or $SO_m$;
p and n are each individually an integer of 1, 2 or 3;
m is 0 or an integer of 1 or 2;
$R_1$ and $R_2$ are each independently H or an optionally substituted alkyl group or $R_1$ and $R_2$ may be taken together with the atom to which they are attached to form an optionally substituted 4- to 7-membered ring optionally containing one or two additional heteroatoms selected from N, O or S
$R_3$ is $NR_4R_5$ or an aryl or heteroaryl group each group optionally substituted;
$R_4$ and $R_5$ are taken together with the atom to which they are attached to form an optionally substituted fused bicyclic, tricyclic or tetracyclic 9- to 15-membered ring system optionally containing one to three additional heteroatoms selected from N, O or S;
$R_6$ and $R_7$ are each independently H, halogen, $OR_{10}$ or an alkyl, alkenyl, alkynyl, cycloalkyl, cycloheteroalkyl, aryl or heteroaryl group each optionally substituted;
$R_8$ and $R_9$ are each independently H, or an alkyl, cycloalkyl, or aryl group each optionally substituted; and
$R_{10}$ is H or an optionally substituted alkyl group; or
a stereoisomer thereof or a pharmaceutically acceptable salt thereof.

The present invention also provides methods and compositions useful for the therapeutic treatment of central nervous system disorders related to or affected by the Histamine-3 receptor.

DETAILED DESCRIPTION OF THE INVENTION

Alzheimer's disease (AD) is characterized by a progressive loss of memory and cognitive function and is the most common cause of dementia in the elderly. AD is believed to affect approximately 15-20 million people worldwide. The goal of treatment in AD, in addition to reversing the disease process, is to improve or at least slow the loss of memory and cognition and to maintain independent function in patients with mild to moderate disease. AD is characterized by numerous deficits in neurotransmitter function (Möller, H-J., European Neuropsychopharmacology, 9, 1999, S53-S59), further a postmortem study in humans suggests that a decrease in brain histamine levels may contribute to the cognitive decline associated with AD, directly or through the cholinergic system (Panula, P., et al, Neuroscience, 82, 1998, 993-997). Histamine-3 (H3) receptor antagonists have been reported to rescue impairments produced pharmacologically or genetically (Miyazaki, S., et al, Life Sciences, 61, 1997, 355-361; Meguro, K., et al, Pharmacology, Biochemistry and Behavior, 50, 1995, 321-325; Fox, G. B., et. al, Beharioral Brain Research, 131, 2002, 151-161; and Komater, V. A., et al, Psychopharmacology, 167, 2003, 363-372). Neuroanatomical, neurochemical, pharmacological and behavioral data support the belief that H3 receptor antagonists may improve cognitive performance in disease states such as mild cognitive impairment and Alzheimer's disease and may have therapeutic value in the treatment of attention deficit hyperactivity disorder (ADHD), schizophrenia, obesity and sleep disorders. To that end, compounds which inhibit the H3 receptor and act as H3 antagonists are earnestly sought.

Surprisingly it has now been found that N-substituted-azacyclylamine compounds of formula I demonstrate H-3 affinity along with significant sub-type selectivity and function as H-3 antagonists. Advantageously, said formula I compounds are effective therapeutic agents for the treatment of central nervous system (CNS) disorders associated with or affected by the H-3 receptor. Accordingly, the present invention provides an N-substituted-azacyclylamine compound of formula I

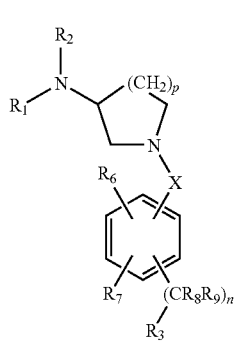

(I)

wherein

X is CO, CH$_2$ or SO$_m$;

p and n are each individually an integer of 1, 2 or 3;

m is 0 or an integer of 1 or 2;

R$_1$ and R$_2$ are each independently H or an optionally substituted alkyl group or R$_1$ and R$_2$ may be taken together with the atom to which they are attached to form an optionally substituted 4- to 7-membered ring optionally containing one or two additional heteroatoms selected from N, O or S R$_3$ is NR$_4$R$_5$ or an aryl or heteroaryl group each group optionally substituted;

R$_4$ and R$_5$ are taken together with the atom to which they are attached to form an optionally substituted fused bicyclic, tricyclic or tetracyclic 9- to 15-membered ring system optionally containing one to three additional heteroatoms selected from N, O or S;

R$_6$ and R$_7$ are each independently H, halogen, OR$_{10}$ or an alkyl, alkenyl, alkynyl, cycloalkyl, cycloheteroalkyl, aryl or heteroaryl group each optionally substituted;

R$_8$ and R$_9$ are each independently H, or an alkyl, cycloalkyl, or aryl group each optionally substituted; and R$_{10}$ is H or an optionally substituted alkyl group; or a stereoisomer thereof or a pharmaceutically acceptable salt thereof.

It is understood that the claims encompass all possible stereoisomers and prodrugs. Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents. The substituent groups, which are optionally present, may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, oxo, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term alkyl includes both (C$_1$-C$_{10}$) straight chain and (C$_3$-C$_{12}$) branched-chain (unless defined otherwise) monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Specifically included within the definition of alkyl are those alkyl groups that are optionally substituted. Suitable alkyl substitutions include, but are not limited to, CN, OH, NR$_{10}$R$_{11}$, halogen, phenyl, carbamoyl, carbonyl, alkoxy or aryloxy.

As used herein, the term haloalkyl designates a C$_n$H$_{2n+1}$ group having from one to 2n+1 halogen atoms which may be the same or different. Examples of haloalkyl groups include CF$_3$, CH$_2$Cl, C$_2$H$_3$BrCl, C$_3$H$_5$F$_2$, or the like.

The term halogen, as used herein, designates fluorine, chlorine, bromine, and iodine.

The term alkenyl, as used herein, refers to either a (C$_2$-C$_{10}$) straight chain or (C$_3$-C$_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term alkynyl, as used in the specification and claims, designates either a (C$_2$-C$_{10}$) straight chain or (C$_3$-C$_{10}$) branched chain monovalent hydrocarbon moiety having at least one triple bond. Such hydrocarbon alkynyl moieties may be mono or polyunsaturated, and may exist in the E or Z configurations. The compounds of this invention are meant to include all possible E and Z configurations. Examples of mono or polyunsaturated hydrocarbon alkynyl moieties include, but are not limited to, propynyl, butynyl, 1,3-butadiynyl, pentynyl, hexynyl, or the like.

The term cycloalkyl, as used herein, refers to a monocyclic, bicyclic, tricyclic, fused, bridged, or spiro monovalent saturated hydrocarbon moiety of 3-10 carbon atoms. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, or the like.

The term cycloheteroalkyl, as used herein, designates a $C_5$-$C_7$ cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein $X_1$ is NR', O or S and R' is H or an optional substituent as defined hereinabove.

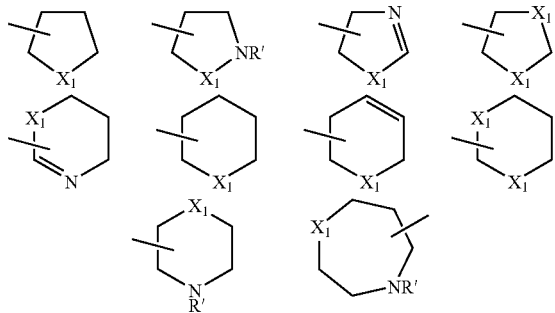

The term aryl, as used herein, refers to an aromatic carbocyclic moiety of up to 20 carbon atoms, which may be a single ring (monocyclic) or multiple rings (bicyclic, up to three rings) fused together or linked covalently. Examples of aryl moieties include, but are not limited to, chemical groups such as phenyl, 1-naphthyl, 2-naphthyl, biphenyl, anthryl, phenanthryl, fluorenyl, indanyl, acenaphthenyl, or the like.

The term heteroaryl as used herein designates an aromatic heterocyclic ring system, which may be a single ring (monocyclic) or multiple rings (bicyclic, up to three rings) fused together or linked covalently. Preferably, heteroaryl is a 5- to 6-membered ring or a fused bicyclic 9- to 11-membered ring system. The rings may contain from one to four hetero atoms selected from nitrogen, oxygen, or sulfur, wherein the nitrogen or sulfur atoms are optionally oxidized, or the nitrogen atom is optionally quarternized. Examples of heteroaryl moieties include, but are not limited to, heterocycles such as: furan, thiophene, pyrrole, pyrazole, imidazole, oxazole, isoxazole, thiazole, isothiazole, oxadiazole, triazole, pyridine, pyrimidine, pyrazine, pyridazine, benzimidazole, benzoxazole, benzisoxazole, benzothiazole, benzofuran, benzothiophene, thianthrene, dibenzofuran, dibenzothiophene, indole, indazole, azaindole, azaindazole, imidazopyridine, indoline, pyridoindole, quinoline, isoquinoline, quinazoline, quinoxaline, purine, tetrahydrocarbazole, hexahydroindolizinoindolone, tetrahydropyranoindole, tetrahydroquinoline, dihydrodibenzoazepine, or the like, preferably benzimidazole, indole, indazole, azaindole or azaindazole.

Exemplary of the fused bicyclic, tricyclic or tetracyclic 9- to 15-membered ring systems formed when $R_4$ and $R_5$ are taken together with the nitrogen atom to which they are attached include indole, indazole, benzimidazole, 1H-carbazole, 2,3,4,9-tetrahydro-1H-carbazole, 5,6,11,11b-tetrahydro-1H-indolizino[8,7-b]indole, 1,2,5,6,11,11b-hexahydro-3H-indolizino[8,7-b]indole, imidazo[4,5-b]pyridine, indoline, 1,2,3,4-tetrahydroquinoline, imidazole or dibenzo[b,f]azepine or the like.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived from organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Preferred compounds of the invention are those compounds of formula I wherein X is CO or $CH_2$. Another group of preferred compounds is those formula I compounds wherein n is 1 and p is 1 or 2. Also preferred are those formula I compounds wherein $R_8$ and $R_9$ are each independently H or methyl.

More preferred compounds of the invention are those compounds of formula I wherein X is CO or $CH_2$ and $R_1$ and $R_2$ are taken together with the atom to which they are attached to form a 5-membered ring. Another group of more preferred compounds is those compounds of formula I wherein X is CO or CH$_2$ and R$_3$ is NR$_4$R$_5$ or an optionally substituted indole, indazole, phenyl or benzimidazole ring. A further group of more preferred compounds are those compounds of formula I wherein X is CO; n is 1; p is 1 or 2; R$_1$ and R$_2$ are taken together with the atom to which they are attached to form a 5-membered ring; and R$_3$ is NR$_4$R$_5$ or an optionally substituted benzimidazole or indole ring. More preferred compounds of formula I are also those formula I compounds wherein R$_3$ is an optionally substituted benzimidazole ring attached at the 2-position of said benzimidazole ring or R$_3$ is NR$_4$R$_5$; and R$_4$ and R$_5$ are taken together with the atom to which they are attached to form an optionally substituted indole, indazole or benzimidazole ring.

Among the preferred compounds of the invention are:

N,N-Dimethyl-1-{4-[(2-phenyl-1H-benzimidazol-1-yl)methyl]-benzoyl}pyrrolidin-3-ylamine;
(3-S)-N,N-Dimethyl-1-{4-[(2-phenyl-1H-benzimidazol-1-yl)methyl]-benzoyl}pyrrolidin-3-ylamine;
(3-R)-N,N-Dimethyl-1-{4-[(2-phenyl-1H-benzimidazol-1-yl)methyl]-benzoyl}pyrrolidin-3-ylamine;
N,N-Dimethyl-1-{4-[(6-fluoro-1H-benzimidazol-1-yl)methyl]-benzoyl}pyrrolidin-3-ylamine;
N,N-Dimethyl-1-{4-[(6-methyl-1H-benzimidazol-1-yl)methyl]-benzoyl}pyrrolidin-3-ylamine;
N,N-Dimethyl-1-{4-[(5-fluoro-1H-benzimidazol-1-yl)methyl]-benzoyl}pyrrolidin-3-ylamine;
N,N-Dimethyl-1-{4-[(4-fluoro-1H-benzimidazol-1-yl)methyl]-benzoyl}pyrrolidin-3-ylamine;
N,N-Dimethyl-1-{[3-(1H-benzimidazol-1-yl)methyl]-benzoyl}pyrrolidin-3-ylamine;
N,N-Dimethyl1-[4-(1H-indol-1-ylmethyl)benzoyl]pyrrolidin-3-ylamine;
N,N-Dimethyl1-{[4-(2,3,4,9-tetrahydro-1H-carbazole)methyl]benzoyl}pyrrolidin-3-ylamine;
N,N-Dimethyl1-{[4-(2-methyl-1H-indol-1-yl)methyl]benzoyl}pyrrolidin-3-ylamine;
N,N-Dimethyl1-{[4-(2-phenyl-1H-indol-1-yl)methyl]benzoyl}pyrrolidin-3-ylamine;
N,N-Dimethyl1-{[4-(5-methoxy-1H-indol-1-yl)methyl]benzoyl}pyrrolidin-3-ylamine;
N,N-Dimethyl1-{[4-(5-methoxy-2-phenyl-1H-indol-1-yl)methyl]benzoyl}pyrrolidin-3-ylamine;
N,N-Dimethyl1-{[4-(7-aza-1H-indol-1-yl)methyl]benzoyl}pyrrolidin-3-ylamine;
N,N-Dimethyl1-{[4-(1H-benzo[d]imidazol-1-yl)methyl]benzoyl}pyrrolidin-3-ylamine;
N,N-Dimethyl1-{[4-(2-methyl-1H-benzo[d]imidazol-1-yl)methyl]benzoyl}pyrrolidin-3-ylamine;
N,N-Dimethyl1-{[4-(5-hydroxy-1H-indol-1-yl)methyl]benzoyl}pyrrolidin-3-ylamine;
N,N-Dimethyl1-{[4-(1,2,3,4-tetrahydroquinolin-1-yl)methyl]benzoyl}pyrrolidin-3-ylamine;
N,N-Dimethyl1-{[4-(5-fluoro-1H-indol-1-yl)methyl]benzoyl}pyrrolidin-3-ylamine;
N,N-Dimethyl1-{[4-(3-cyano-1H-indol-1-yl)methyl]benzoyl}pyrrolidin-3-ylamine;
N,N-Dimethyl1-{[4-(2-phenyl-1H-imidazol-1-yl)methyl]benzoyl}pyrrolidin-3-ylamine;
1'-{4-[(2-Phenyl-1H-benzimidazol-1-yl)methyl]benzoyl}-1,3'-bipyrrolidine;
1'-{4-[(5-Chloro-2-methyl-1H-benzimidazol-1-yl)methyl]benzoyl}-1,3'-bipyrrolidine;
1'-{4-[(6-Chloro-2-methyl-1H-benzimidazol-1-yl)methyl]benzoyl}-1,3'-bipyrrolidine;
1'-{4-[(6-Methyl-1H-benzimidazol-1-yl)methyl]benzoyl}-1,3'-bipyrrolidine;
1'-{4-[(5-Fluoro-1H-benzimidazol-1-yl)methyl]benzoyl}-1,3'-bipyrrolidine;
(2-R)-1'-[4-(1H-Benzimidazol-1-ylmethyl)benzoyl]-2-methyl-1,3'-bipyrrolidine;
(3'-R)-1'-{4-[(2-Methyl-1H-benzimidazol-1-yl)methyl]benzoyl}-1,3'-bipyrrolidine;
(3'-S)-1'-{4-[(2-Methyl-1H-benzimidazol-1-yl)methyl]benzoyl}-1,3'-bipyrrolidine;
(3'S)-[4-(1H-Indol-1-ylmethyl)benzoyl]-1,3'-bipyrrolidine;
(3'S)-[4-(1H-Indazol-1-ylmethyl)benzoyl]-1,3'-bipyrrolidine;
(3'S)-1'-{4-[(5-Chloro-2-methyl-1H-benzimidazol-1-yl)methyl]benzoyl}-1,3'-bipyrrolidine;
(3'S)-1'-{4-[(6-Chloro-2-methyl-1H-benzimidazol-1-yl)methyl]benzoyl}-1,3'-bipyrrolidine;
(3'S)-1'-{4-[(6-Fluoro-1H-benzimidazol-1-yl)methyl]benzoyl}-1,3'-bipyrrolidine;
(3'S)-1'-{4-[(6-Fluoro-1H-benzimidazol-1-yl)methyl]benzyl}-1,3'-bipyrrolidine;
(3'S)-1'-{4-[(5-Fluoro-1H-benzimidazol-1-yl)methyl]benzyl}-1,3'-bipyrrolidine;
(3'S)-1'-{4-[(5-Fluoro-1H-benzimidazol-1-yl)methyl]benzoyl}-1,3'-bipyrrolidine;
(3'S)-1'-{4-[(7-Chloro-1H-indol-1-yl)methyl]benzoyl}-1,3'-bipyrrolidine;
9-{4-[(3'S)-1,3'-Bipyrrolidin-1-ylcarbonyl]benzyl}-9H-carbazole;
(3'-S)-1'-{4-[(1S)-1-(2-Methyl-1H-benzimidazol-1-yl)ethyl]benzoyl}-1,3'-bipyrrolidine;
(3'-S)-1'-{4-[(1R)-1-(2-Methyl-1H-benzimidazol-1-yl)ethyl]benzoyl}-1,3'-bipyrrolidine;
(3'-S)-1'-[4-(1H-Benzimidazol-1-ylmethyl)benzyl]-1,3'-bipyrrolidine;
(3'-S)-1'-[4-(1H-Benzimidazol-1-ylmethyl)benzoyl]-1,3'-bipyrrolidine;
N,N-Dimethyl-1-{4-[(2-phenyl-1H-benzimidazol-1-yl)methyl]-benzoyl}pyrrolidin-3-ylamine;
(3-S)-N,N-Dimethyl-1-{4-[(2-phenyl-1H-benzimidazol-1-yl)methyl]-benzoyl}pyrrolidin-3-ylamine;
(3-R)-N,N-Dimethyl-1-{4-[(2-phenyl-1H-benzimidazol-1-yl)methyl]-benzoyl}pyrrolidin-3-ylamine;
N,N-Dimethyl-1-{4-[(6-fluoro-1H-benzimidazol-1-yl)methyl]-benzoyl}pyrrolidin-3-ylamine;
N,N-Dimethyl-1-{4-[(6-methyl-1H-benzimidazol-1-yl)methyl]-benzoyl}pyrrolidin-3-ylamine;
N,N-Dimethyl-1-{4-[(5-fluoro-1H-benzimidazol-1-yl)methyl]-benzoyl}pyrrolidin-3-ylamine;
N,N-Dimethyl-1-{4-[(4-fluoro-1H-benzimidazol-1-yl)methyl]-benzoyl}pyrrolidin-3-ylamine;
N,N-Dimethyl-1-{[3-(1H-benzimidazol-1-yl)methyl]-benzyl}pyrrolidin-3-ylamine;
N,N-Dimethyl1-[4-(1H-indol-1-ylmethyl)benzyl]pyrrolidin-3-ylamine;
N,N-Dimethyl1-{[4-(2,3,4,9-tetrahydro-1H-carbazole)methyl]benzyl}pyrrolidin-3-ylamine;
(3'S)-1'-[4-(1H-indol-3-ylmethyl)benzoyl]-1,3'-bipyrrolidine;
(3'S)-1'-{4-[(1-methyl-1H-indol-3-yl)methyl]benzoyl}-1,3'-bipyrrolidine;
(3S)-N,N-dimethyl-1-{4-[(1-methyl-1H-indol-3-yl)methyl]benzoyl}pyrrolidin-3-amine;
2-{4-[(3-piperidin-1-ylpyrrolidin-1-yl)carbonyl]benzyl}-1H-benzimidazole;
1'-{4-[(1-ethyl-1H-benzimidazol-2-yl)methyl]benzoyl}-1,3'-bipyrrolidine;

1'-{4-[(1-methyl-1H-benzimidazol-2-yl)methyl]benzoyl}-1,3'-bipyrrolidine;
1-methyl-2-{4-[(3-piperidin-1-ylpyrrolidin-1-yl)carbonyl]benzyl}-1H-benzimidazole;
1'-[4-(1H-benzimidazol-2-ylmethyl)benzoyl]-1,3'-bipyrrolidine;
(3'S)-1'-(4-benzylbenzoyl)-1,3'-bipyrrolidine;
(3'S)-1'-{4-[(1-propyl-1H-benzimidazol-2-yl)methyl]benzoyl}-1,3'-bipyrrolidine;
(3'S)-1'-{4-[(1-isopropyl-1H-benzimidazol-2-yl)methyl]benzoyl}-1,3'-bipyrrolidine;
(3'S)-1'-{4-[(1-isobutyl-1H-benzimidazol-2-yl)methyl]benzoyl}-1,3'-bipyrrolidine;
(3'S)-1'-(4-{[1-(cyclopropylmethyl)-1H-benzimidazol-2-yl]methyl}benzoyl)-1,3'-bipyrrolidine;
(3'S)-1'-(4-{[1-(phenylsulfonyl)-1H-benzimidazol-2-yl]methyl}benzoyl)-1,3'-bipyrrolidine;
(3'S)-1'-(4-{[1-(2-methoxyethyl)-1H-benzimidazol-2-yl]methyl}benzoyl)-1,3'-bipyrrolidine;
2-(2-{4-[(3'S)-1,3'-bipyrrolidin-1'-ylcarbonyl]benzyl}-1H-benzimidazol-1-yl)ethanol;
(3'S)-1'-{4-[(1-ethyl-1H-benzimidazol-2-yl)methyl]benzoyl}-1,3'-bipyrrolidine;
(3'S)-1'-(4-{[1-(2-phenylethyl)-1H-benzimidazol-2-yl]methyl}benzoyl)-1,3'-bipyrrolidine;
(3'S)-1'-{4-[(1-ethyl-1H-benzimidazol-2-yl)methyl]benzyl}-1,3'-bipyrrolidine;
(3'S)-1'-{4-[(1-phenyl-1H-benzimidazol-2-yl)methyl]benzoyl}-1,3'-bipyrrolidine; 1'-{4-[(5-methyl-1H-benzimidazol-1-yl)methyl]benzoyl}-1,3'-bipyrrolidine;
5-methyl-1-{4-[(3-piperidin-1-ylpyrrolidin-1-yl)carbonyl]benzyl}-1H-benzimidazole;
4-fluoro-1-{4-[(3-piperidin-1-ylpyrrolidin-1-yl)methyl]benzyl}-1H-benzimidazole;
1'-[4-(1H-benzimidazol-1-ylmethyl)-3-chlorobenzyl]-1,3'-bipyrrolidine;
1-{4-[(4-fluoro-1H-benzimidazol-1-yl)methyl]benzyl}-N,N-dimethylpyrrolidin-3-amine;
5-methyl-1-(4-{[3-(2-methylpiperidin-1-yl)pyrrolidin-1-yl]carbonyl}benzyl)-1H-benzimidazole;
5-methyl-1-{4-[(3-morpholin-4-ylpyrrolidin-1-yl)carbonyl]benzyl}-1H-benzimidazole;
5-methyl-1-(4-{[3-(4-methylpiperidin-1-yl)pyrrolidin-1-yl]carbonyl}benzyl)-1H-benzimidazole;
5-methyl-1-(4-{[3-(4-methylpiperazin-1-yl)pyrrolidin-1-yl]carbonyl}benzyl)-1H-benzimidazole;
5-methyl-1-(4-{[3-(3-methylpiperidin-1-yl)pyrrolidin-1-yl]carbonyl}benzyl)-1H-benzimidazole;
((2s)-1'-{4-[5-methyl-1H-benzimidazol-1-yl)methyl]benzoyl}-1,3'-bipyrrolidin-2-yl)methanol;
N,N-dimethyl-1-{4-[(5-methyl-1H-benzimidazol-1-yl)methyl]benzoyl}pyrrolidin-3-amine;
N-ethyl-N-methyl-1-{4-[(5-methyl-1H-benzimidazol-1-yl)methyl]benzoyl}pyrrolidin-3-amine;
1-{2-chloro-4-[(3-piperidin-1-ylpyrrolidin-1-yl)methyl]benzyl}-1H-benzimidazole;
1-[4-(1H-benzimidazol-1-ylmethyl)-2-methozybenzoyl]-N,N-dimethylpyrrolidin-3-amine;
1-[4-(1H-benzimidazol-1-ylmethyl)-3-chlorobenzyl]-N-ethyl-Nmethylpyrrolidin-3-amine;
(2R)-1'-[4-(1H-benzimidazol-1-ylmethyl)-2-methozybenzoyl]-2-methyl-1,3'-bipyrrolidine;
2-benzyl-1'-{4-[(5-methyl-1H-benzimidazol-1-yl)methyl]benzoyl}-1,3'-bipyrrolidine;
1'-{4-[(7-methyl-1H-benzimidazol-1-yl)methyl]benzoyl}-1,3'-bipyrrolidine;
(2R)-1'-{4-[(5-fluoro-1H-benzimidazol-1-yl)methyl]benzoyl}-2-methyl-1,3'-bipyrrolidine;
(2R)-2-methyl-1'-{4-[(5-methyl-1H-benzimidazol-1-yl)methyl]benzoyl}-1,3'-bipyrrolidine;
1-[4-(1H-benzimidazol-1-ylmethyl)-3-chlorobenzyl]-N,N-dimethylpyrrolidin-3-amine (WAY361865);
(2S)-1'-{4-[(5-fluoro-1H-benzimidazol-1-yl)methyl]benzoyl}-2-methyl-1,3'-bipyrrolidine;
1-{4-[(3-azepan-1-ylpyrrolidin-1-yl)carbonyl]benzyl}-5-methyl-1H-benzimidazole;
5-methyl-1-(4-{[3-(4-methyl-1,4-diazepan-1-yl)pyrrolidin-1-yl]carbonyl}benzyl)-1H-benzimidazole;
(3'S)-1'-{4-[(5-fluoro-1H-benzimidazol-1-yl)methyl]benzoyl}-1,3'-bipyrrolidine;
(3'S)-1'-{4-[(5-fluoro-1H-benzimidazol-1-yl)methyl]benzyl}-1,3'-bipyrrolidine;
7-methyl-1-{4-[(3-piperidin-1-ylpyrrolidin-1-yl)carbonyl]benzyl}-1H-benzimidazole;
(2R)-1'-{4-[(5-fluoro-1H-benzimidazol-1-yl)methyl]benzyl}-2-methyl-1,3'-bipyrrolidine;
1-{4-[(3-azetidin-1-ylpyrrolidin-1-yl)carbonyl]benzyl}-5-methyl-1H-benzimidazole;
1'-[4-(1H-benzimidazol-1-ylmethyl)-2-fluorobenzoyl]-1,3'-bipyrrolidine;
(3'S)-1'-{4-[(7-fluoro-1H-benzimidazol-1-yl)methyl]benzoyl}-1,3'-bipyrrolidine;
1-(4{[(3S)-3-azepan-1-ylpyrrolidin-1-yl]carbonyl}benzyl)-7-fluoro-1H-benzimidazole;
7-fluoro-1-(4-{[(3S)-3-piperidin-1-ylpyrrolidin-1-yl]carbonyl}benzyl)-1H-benzimidazole;
(3S)-N-ethyl-1-{4-[(7-fluoro-1H-benzimidazol-1-yl)methyl]benzoyl}-N-methylpyrrolidin-3-amine;
7-fluoro-1-(4-{[(3S)-3-(3-methylpiperidin-1-yl)pyrrolidin-1-yl]carbonyl}benzyl)-1H-benzimidazole;
1-(4{[(3S)-3-azetidin-1-ylpyrrolidin-1-yl]carbonyl}benzyl)-7-fluoro-1H-benzimidazole;
(3'S)-1'-(4-{[2-(trifluoromethyl)-1H-benzimidazol-1-yl]methyl}benzoyl)-1,3'-bipyrrolidine;
(3'S)-1'-{4-[1-(7-chloro-1H-indol-1-yl)ethyl]benzoyl}-1,3'-bipyrrolidine;
(3'S)-1'-{4-[1-(5-chloro-2-methyl-1H-benzimidazol-1-yl)ethyl]benzoyl}-1,3'-bipyrrolidine;
(3'S)-1'-{4-[(1S)-1-(1H-benzimidazol-1-yl)ethyl]benzoyl}-1,3'-bipyrrolidine;
(3'S)-1'-{4-[(1R)-1-(1H-benzimidazol-1-yl)ethyl]benzoyl}-1,3'-bipyrrolidine;
(3'S)-1'-{4-[(5-chloro-2-methyl-1H-benzimidazol-1-yl)methyl]benzoyl}-1,3'-bipyrrolidine;
(3'S)-1'-{4-[(6-chloro-2-methyl-1H-benzimidazol-1-yl)methyl]benzoyl}-1,3'-bipyrrolidine;
(3'S)-1'-{4-[(1S)-1-(5-chloro-2-methyl-1H-benzimidazol-1-yl)ethyl]benzoyl}-1,3'-bipyrrolidine;
(3'S)-1'-{4-[(1S)-1-(6-chloro-2-methyl-1H-benzimidazol-1-yl)ethyl]benzoyl}-1,3'-bipyrrolidine;
(3'S)-1'-{4-[(1R)-1-(5-chloro-2-methyl-1H-benzimidazol-1-yl)ethyl]benzoyl}-1,3'-bipyrrolidine;
(3'S)-1'-{4-[(1R)-1-(6-chloro-2-methyl-1H-benzimidazol-1-yl)ethyl]benzoyl}-1,3'-bipyrrolidine;
(3S)-1-{4-[(1R)-1-(6-chloro-2-methyl-1H-benzimidazol-1-yl)ethyl]benzoyl}pyrrolidin-3-amine;
(3S)-1-{4-[(1R)-1-(5-chloro-2-methyl-1H-benzimidazol-1-yl)ethyl]benzoyl}pyrrolidin-3-amine;

(3'S)-1'-{4-[(5-chloro-1H-benzimidazol-1-yl)methyl]benzoyl}-1,3'-bipyrrolidine;
(3'S)-1'-{4-[(6-chloro-1H-benzimidazol-1-yl)methyl]benzoyl}-1,3'-bipyrrolidine;
(3S)-1-{4-[(5-chloro-1H-benzimidazol-1-yl)methyl]benzoyl}pyrrolidin-3-amine;
(3S)-1-{4-[(1S)-1-(6-chloro-2-methyl-1H-benzimidazol-1-yl)ethyl]benzoyl}pyrrolidin-3-amine;
(3S)-1-{4-[(1S)-1-(5-chloro-2-methyl-1H-benzimidazol-1-yl)ethyl]benzoyl}pyrrolidin-3-amine;
(3'S)-1'-{4-[1-(5-chloro-1H-indol-1-yl)ethyl]benzoyl}-1,3'-bipyrrolidine;
1-(1-{4-[(3'S)-1,3'-bipyrrolidin-1'-ylcarbonyl]phenyl}ethyl)-1H-indole-5-carbonitrile;
2-methyl-1-[1-(4-{[1R,4R)-5-methyl-2,5-diazabicyclo[2.2.1]hept-2-yl]carbonyl}phenyl]-1H-benzimidazole;
1-{4-[(3-pyrrolidin-1-ylpiperidin-1-yl)carbonyl]benzyl}-1H-benzimidazole;
1'-[4-(1H-benzimidazol-1-ylmethyl)benzoyl]-1,3'-bipiperidine;
1-(4-{[3-(2-methylpyrrolidin-1-yl)piperidin-1-yl]carbonyl}benzyl)-1H-benzimidazole;
4-(1H-benzimidazol-1-ylmethyl)-N-(2-pyrrolidin-1-ylethyl)benzamide;
4-[(2-methyl-1H-benzimidazol-1-yl)methyl]-N-(2-pyrrolidin-1-ylethyl)benzamide;
1-(4-{[3-(4-methylpiperidin-1-yl)pyrrolidin-1-yl]carbonyl}benzyl)-1H-benzimidazole;
(2R,3'R)-1'-[4-(1H-benzimidazol-1-ylmethyl)benzoyl]-2-methyl-1,3'-bipyrrolidine;
(2S,3'R)-1'-[4-(1H-benzimidazol-1-ylmethyl)benzoyl]-2-methyl-1,3'-bipyrrolidine;

a stereoisomer thereof; or a pharmaceutically acceptable salt thereof.

Compounds of the invention may be prepared using conventional synthetic methods and, if required, standard isolation or separation techniques. For example compounds of formula I wherein X is CO and p is 1 (Ia) may be prepared by reacting a benzoic acid of formula II with 3-hydroxypyrrolidine utilizing standard peptide forming conditions, such as activation of the carboxylic acid with a suitable carbodiimide such as 1-(3-dimethylaminopropyl)-3-ethylcarbodiimide in a solvent such as dichloromethane in the presence of 1-hydroxybenzotriazole (HOBT), to give the amide of formula III; reacting the formula III amide with methanesulfonyl chloride in the presence of a base such as diisopropylethyl amine in a solvent such as dichloromethane to give the corresponding mesylate ester; and displacing said ester with an amine, $HNR_1R_2$, in a solvent such as N,N-dimethylformamide (DMF) under microwave conditions to give the desired compound of formula Ia. Advantageously, the use of a chiral 3-hydroxypyrrolidine in the initial coupling step allows for the stereospecific synthesis of the formula III compound. As the displacement reaction occurs in a stereospecific manner with inversion of configuration, the use of a chiral formula III compound affords the desired compound of formula Ia stereospecifically. Of course it is understood that the use of racemic 3-hydroxypyrrolidine will ultimately afford the desired racemic formula Ia product. The reaction is shown in Scheme I.

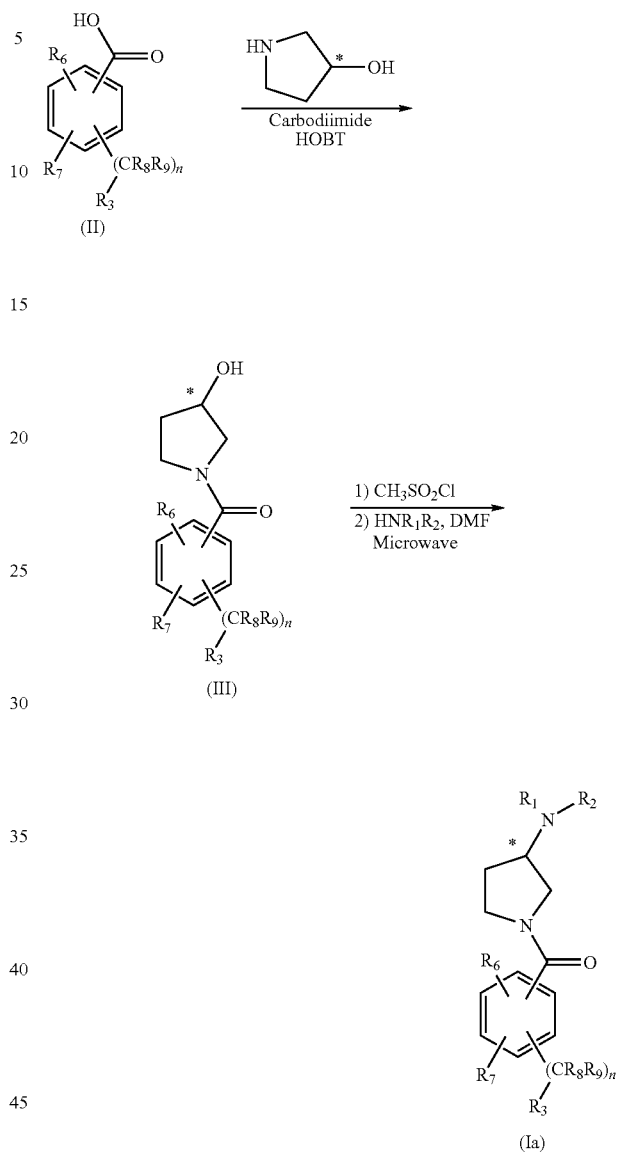

Compounds of formula II wherein $R_3$ is an optionally substituted benzimidazol-2-yl group (IIa) may be prepared by reacting a bromomethyl benzoate of formula IV with sodium cyanide in a solvent such as dimethylsulfoxide (DMSO) to give the corresponding nitrile compound; hydrolyzing said nitrile with methanolic HCl to give the corresponding diester; selectively saponifying said diester to give the carboxylic acid of formula V; coupling the formula V acid with a phenylene diamine of formula VI utilizing standard peptide forming conditions, for example activation of the carboxylic acid with a suitable carbodiimide such as 1-(3-dimethylaminopropyl)-3-ethylcarbodiimide in a solvent such as dichloromethane in the presence of 1-hydroxybenzotriazole (HOBT), to afford the corresponding amide; said amide is cyclized via treatment with acetic acid at 140° C., followed by base hydrolysis to provide the desired benzimidazol-2-yl compound of formula IIa. The reaction is shown in Scheme II wherein R' is $C_1$-$C_4$ alkyl; R is an optional substituent as described hereinabove; and p is 0, 1 or 2.

SCHEME II

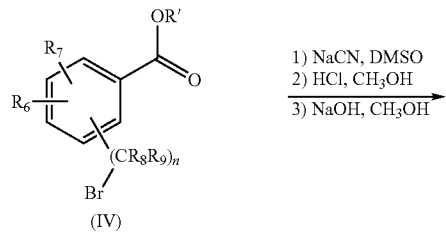

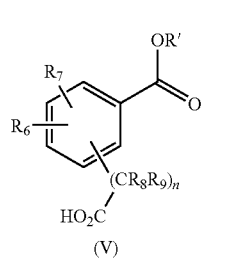

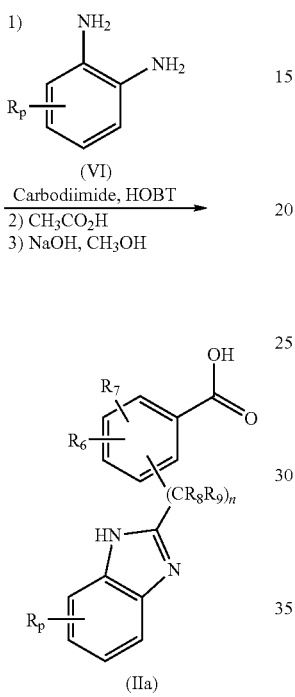

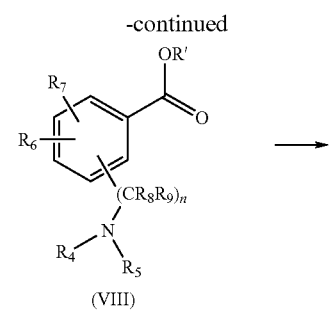

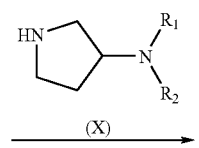

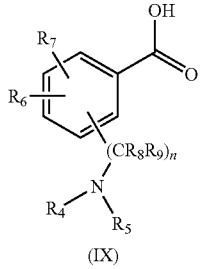

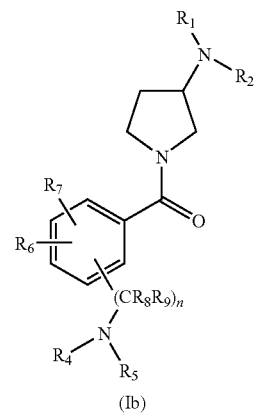

Compounds of formula I wherein X is CO; p is 1; and $R_3$ is $NR_4R_5$ (Ib) may be prepared by reacting the bromomethylbenzoate of formula IV with a cyclic amine of formula VII in the presence of base such as sodium hydride or potassium t-butoxide to give the compound of formula VIII; hydrolyzing the formula VIII ester by either acid or base hydrolysis, for example sulfuric acid or lithium hydroxide in a suitable solvent such as methanol/water, to give the corresponding acid of formula IX; and coupling the formula IX acid with a 3-aminopyrrolidine compound of formula X in the presence of a suitable coupling agent such as diisopropylcarbodiimide to give the desired compound of formula Ib. The reaction is shown in Scheme III wherein R' is $C_1$-$C_4$ alkyl.

SCHEME III

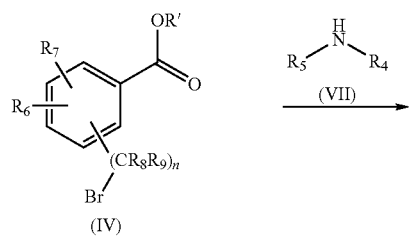

Optionally, the formula IX acid may be converted to an activated moiety such as the corresponding acid chloride by treatment with oxalylchloride, or a mixed anhydride by treatment with pivaloyl chloride and triethylamine; and the activated acid may be coupled with the formula X 3-aminopyrrolidine to give the desired formula Ib compound.

Alternatively, compounds of formula Ib may be prepared by reacting the formula IX benzoic acid with oxalyl chloride to form the corresponding acid chloride; coupling said acid chloride with 3-pyrrolidinol to give the compound of formula XI; reacting the formula XI compound with methane sulfonyl chloride to give the corresponding mesylate of formula XII; and reacting said mesylate with an amine, $HNR_1R_2$, to give the desired compound of formula Ib. The reaction is shown in Scheme IV wherein Ms represents $CH_3SO_2$.

SCHEME IV

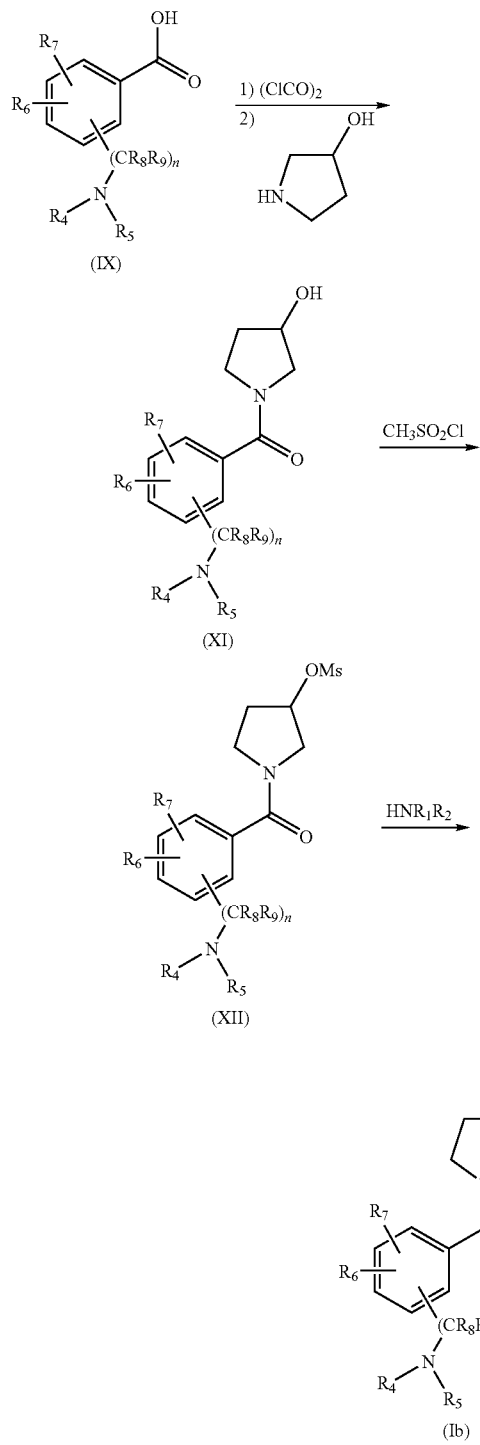

mula VII as described hereinabove in reaction scheme III to give the desired compound of formula Ib. The reaction is shown in Scheme V.

SCHEME V

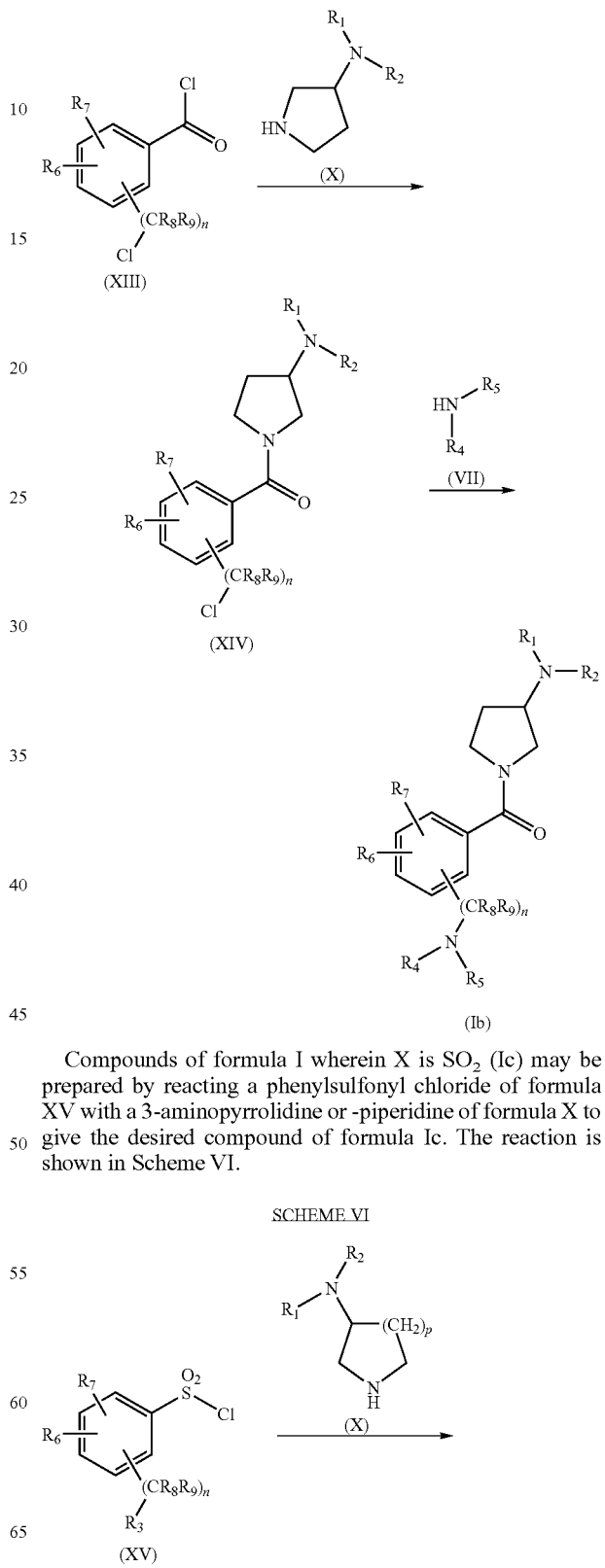

Compounds of formula Ib may also be prepared by reversing the sequence of reactions, for example a chloromethylbenzolychloride of formula XIII may be coupled with the formula X 3-aminopyrrolidine in the presence of a suitable base such as diisopropylethyl amine to give the chloromethylbenzamide of formula XIV and said chloromethyl formula XIV compound may be coupled with a cyclic amine of for- Compounds of formula I wherein X is $SO_2$ (Ic) may be prepared by reacting a phenylsulfonyl chloride of formula XV with a 3-aminopyrrolidine or -piperidine of formula X to give the desired compound of formula Ic. The reaction is shown in Scheme VI.

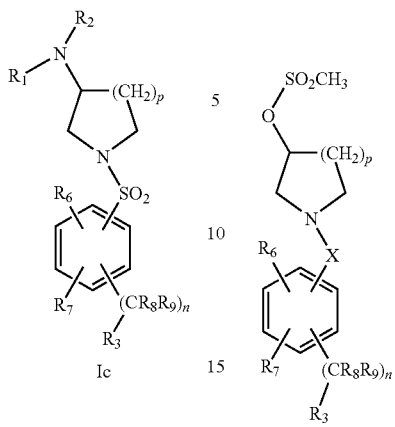

(Ic)

Compounds of formula I wherein X is CH$_2$ and p is 1 (Id) may be readily prepared by reducing the formula Ia compound with a suitable reducing agent such as LiAlH$_4$ or borane to give the desired compound of formula Ib. The reaction is shown in Scheme VII.

SCHEME VII

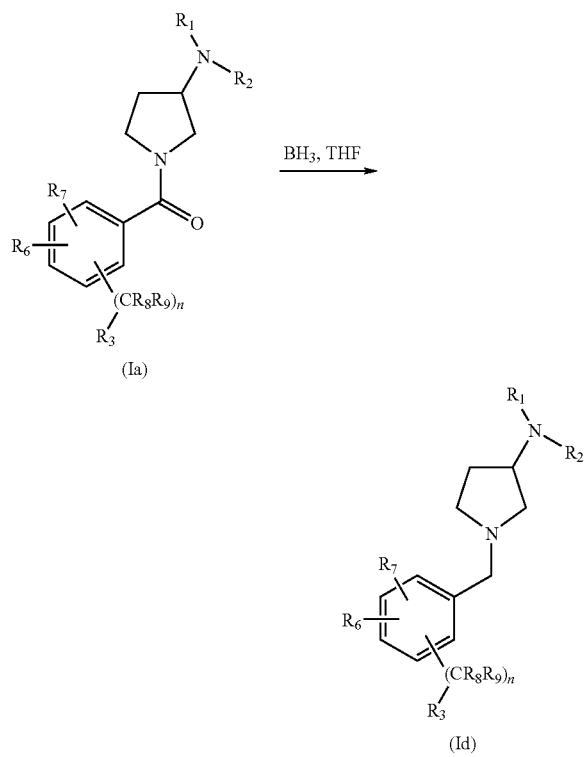

Compounds of formula Ia, Ib and Id wherein p is 2 or 3 may be prepared as shown in Schemes I, III, IV, V and VII and replacing the 3-hydroxypyrrolidine or pyrrolidin-3-ylamine with the corresponding 3-hydroxypiperidine or -homopiperidine or piperidin-3-ylamine or homopiperidin-3-ylamine compounds.

Advantageously, the present invention provides a method for the preparation of a compound of formula I which comprises reacting a compound of formula XVI with an amine, HNR$_1$R$_2$, in the presence of microwave irradiation, optionally in the presence of a solvent. The process is shown in Scheme VIII.

SCHEME VIII

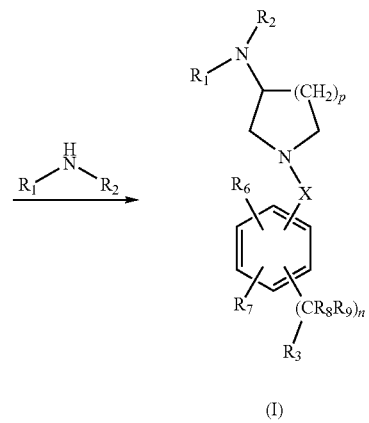

(XVI)      (I)

Solvents suitable for use in the method of invention include dimethyl formamide, acetonitrile, tetrahydrofuran, or the like.

Beneficially, the formula I compounds of the invention are useful for the treatment of CNS disorders related to or affected by the Histamine-3 receptor including cognitive disorders, for example Alzheimer's disease, mild cognitive impairment, attention deficit hyperactivity disorder, schizophrenia, memory loss, sleep disorders, obesity or the like. Accordingly, the present invention provides a method for the treatment of a disorder of the central nervous system related to or affected by the Histamine-3 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The inventive method includes: a method for the treatment of schizophrenia; a method for the treatment of a disease associated with a deficit in memory, cognition or learning or a cognitive disorder such as Alzheimer's disease or attention deficit hyperactivity disorder; a method for the treatment of a mild cognitive disorder, a method for the treatment of a developmental disorder such as schizophrenia; a method for the treatment of a sleep disorder or any other CNS disease or disorder associated with or related to the H3 receptor.

In one embodiment, the present invention provides a method for treating attention deficit hyperactivity disorders (ADHD, also known as Attention Deficit Disorder or ADD) in both children and adults. Accordingly, in this embodiment, the present invention provides a method for treating attention deficit disorders in a pediatric patient.

The present invention therefore provides a method for the treatment of each of the conditions listed above in a patient, preferably in a human, said method comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

In one embodiment, the invention relates to compositions comprising at least one compound of formula I, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I.

In certain embodiments, the invention relates to compositions comprising at least one compound of formula I, or a pharmaceutically acceptable salt thereof, and one or more pharmaceutically acceptable carriers, excipients, or diluents. Such compositions are prepared in accordance with acceptable pharmaceutical procedures. Pharmaceutically acceptable carriers are those carriers that are compatible with the other ingredients in the formulation and are biologically acceptable.

The compounds of formula I may be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

In certain embodiments, a compound of formula I is provided in a disintegrating tablet formulation suitable for pediatric administration.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

In certain embodiments, a liquid pharmaceutical composition is provided wherein said composition is suitable for pediatric administration. In other embodiments, the liquid composition is a syrup or suspension.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula I may be administered rectally or vaginally in the form of a conventional suppository. For administration by intranasal or intrabronchial inhalation or insufflation, the compounds of formula I can be formulated into an aqueous or partially aqueous solution; which can then be utilized in the form of an aerosol. The compounds of formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The therapeutically effective amount of a compound of formula I provided to a patient will vary depending upon what is being administered, the purpose of the administration, such as prophylaxis or therapy, the state of the patient, the manner of administration, or the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. Generally, a starting dose is about 5 mg per day with gradual increase in the daily dose to about 150 mg per day, to provide the desired dosage level in the patient.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs", Textbook of Drug Design and Development, Chapter 5, 113-191 (1991), Bundgaard, et al., Journal of Drug Delivery Reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

For a more clear understanding, and in order to illustrate the invention more clearly, specific examples thereof are set forth hereinbelow. The following examples are merely illustrative and are not to be understood as limiting the scope and underlying principles of the invention in any way. The terms HPLC and $^1$H NMR designate high performance liquid chromatography and proton nuclear magnetic resonance, respectively. The term MS designates mass spectroscopy with (+) referring to the positive mode which generally gives a M+1 (or M+H) absorption where M=the molecular mass. All compounds are analyzed at least by MS and $^1$H NMR. The terms DMF and THF designate dimethyl formamide and tetrahydrofuran, respectively. In the chemical drawings, the term Ph represents phenyl. Unless otherwise noted, all parts are parts by weight.

EXAMPLE 1

Preparation of N,N-Dimethyl-1-{4-[(2-phenyl-1H-benzimidazol-1-yl)methyl]-benzoyl}pyrrolidin-3-ylamine

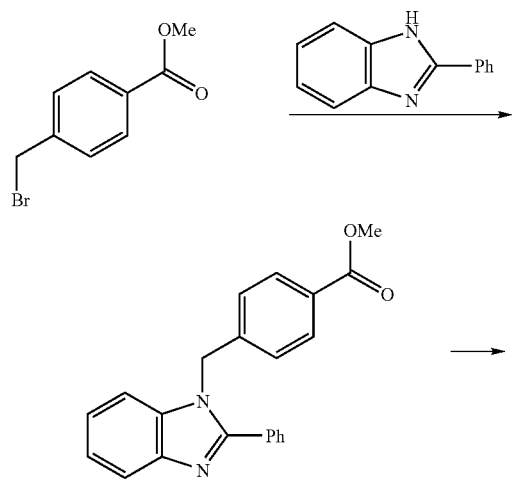

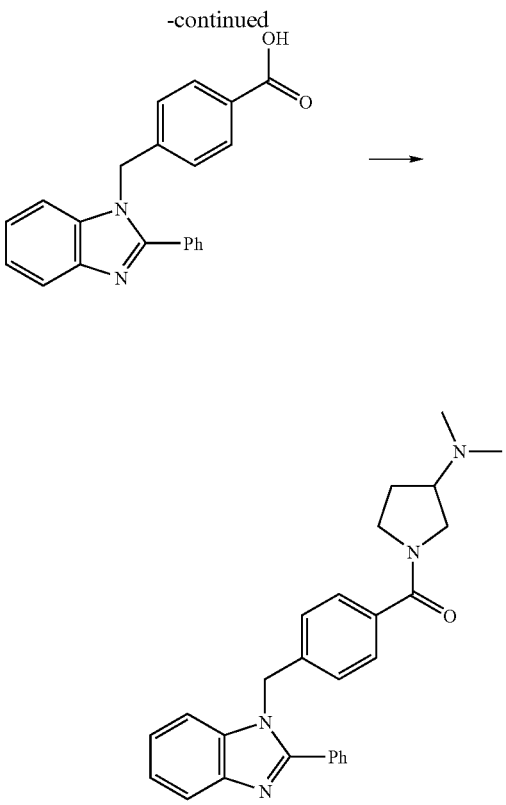

Step 1. 2-Phenylbenzimidazole (5 mmol, 0.97 g) is dissolved in THF/DMF (5:1, 20 mL) and sodium hydride (0.5 g) is added. After stirring for 10 minutes at r.t. methyl 4-(bromomethyl)benzoate (1.4 g, 6 mmol) is added. The reaction is stirred at r.t. overnight, then diluted with EtOAc (100 mL) and washed with satd. NaHCO$_3$, dried over MgSO$_4$ and concentrated. The resultant residue is identified by HPLC* and MS [343.2 m/e (M+H)] and used in the next step.

Step 2. The 4-(2-phenyl-benzoimidazol-1-ylmethyl)-benzoic acid methyl ester obtained in step 1 is dissolved in MeOH/water (2:1, 30 mL), treated with lithium hydroxide (0.42 g, 10 mmol), stirred at room temperature overnight, evaporated to remove the MeOH, diluted with 1 N sodium hydroxide (50 mL), washed with EtOAc, acidified with concentrated HCl and extracted with EtOAc. The extracts were combined, dried over MgSO$_4$ and concentrated. The resultant residue is identified by HPLC* and MS [329.2 m/e (M+H)] and used in the next step.

Step 3. The 4-(2-phenyl-benzoimidazol-1-ylmethyl)-benzoic acid (0.2 mmol) obtained in step 2 is dissolved in DCM (5 mL) and oxalylchloride (0.2 mL, 0.4 mmol, 2 M solution in DCM) and DMF (2 drops) are added. The solution is stirred for 2 hours at room temperature then concentrated in vacuo. The residue is dissolved in THF, treated with diisopropylethylamine (DIEA) (0.09 mL, 0.5 mmol) and 3-(dimethylamino) pyrrolidine (0.22 mmol, 22 uL), stirred at room temperature overnight then concentrated. This residue is dissolved in a mixture of DMSO, MeOH and water (1.5 mL) and purified by reverse-phase semi-preparative HPLC[1] to the title product as a white powder (13 mg), identified by HPLC[2] and MS [425.2 m/e (M+H)].

EXAMPLE 2

Preparation of (3-S)-N,N-Dimethyl-1-{4-[(2-phenyl-1H-benzimidazol-1-yl)methyl]-benzoyl}pyrrolidin-3-ylamine

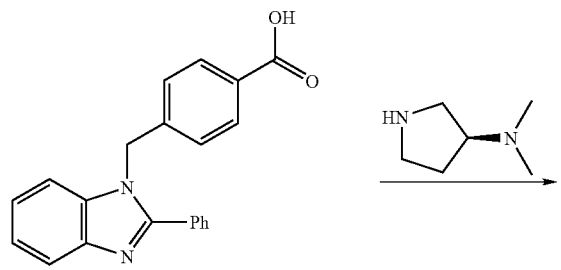

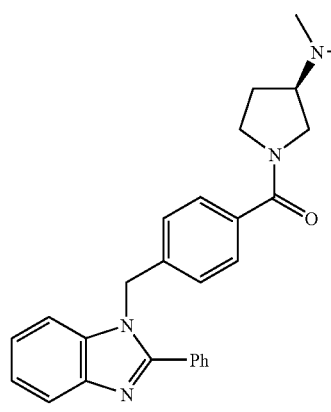

Using essentially the same procedure described in Example 1 and employing (3-S)-dimethylaminopyrrolidine in step 3, the title compound was obtained and identified by HPLC and mass spectral analyses. MS [425.2] m/e (M+H), Retention Time 2.94 min.

EXAMPLE 3

Preparation of (3-R)-N,N-Dimethyl-1-{4-[(2-phenyl-1H-benzimidazol-1-yl)methyl]-benzoyl}pyrrolidin-3-ylamine

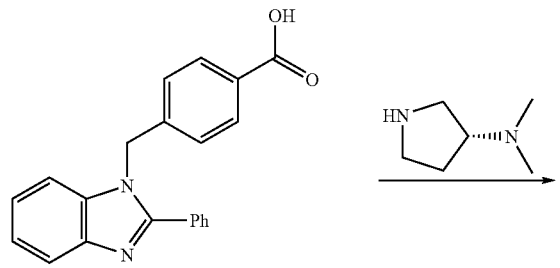

-continued

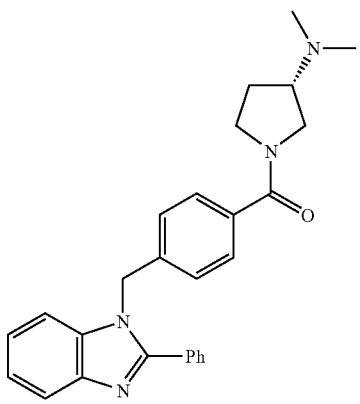

Using essentially the same procedure described in Example 1 and employing (3-R)-dimethylaminopyrrolidine in step 3, the title compound was obtained and identified by HPLC and mass spectral analyses. MS [425.2] m/e (M+H), Retention Time 2.92 min.

EXAMPLES 4-7

Preparation of N,N-Dimethyl-1-{4-[(substituted-1H-benzimidazol-1-yl)methyl]-benzoyl}pyrrolidin-3-ylamine

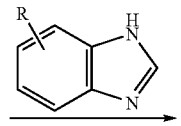

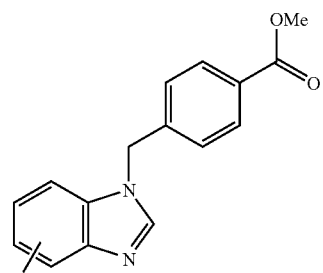

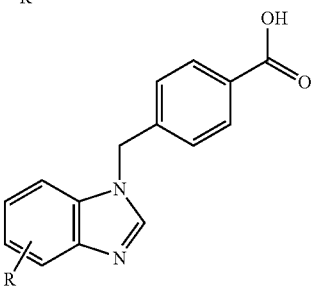

-continued

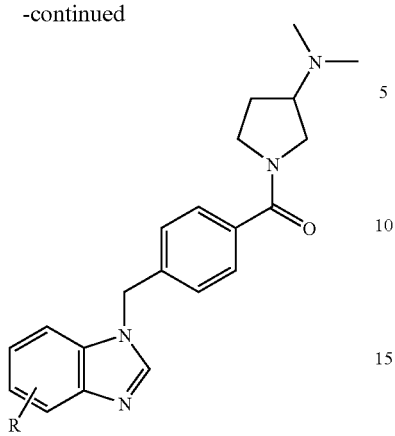

Using essentially the same procedure described in Example 1 and employing the appropriate benzimidazole in step 1, the compounds shown in Table I were obtained and identified by HPLC and mass spectral analyses. HPLC Conditions: A=0.02% TFA in water, B=0.02% TFA in acetonitrile, 10-95% B in 5 min., 1.0 mL/min, 50° C., 215 nm detection, Waters Xterra™ 2×50 mm column.

TABLE I

| Ex. No. | R | [M + H] | Time (Min.) |
|---|---|---|---|
| 4 | 6-F | 367.3 | 3.84 |
| 5 | 6-methyl | 363.3 | 4.02 |
| 6 | 5-F | 367.4 | 4.14 |
| 7 | 4-F | 367.3 | 4.62 |

EXAMPLES 8-11

Preparation of N-Substituted-1-{[3-(1H-benzimidazol-1-yl)methyl]-benzoyl}azacyc-3-ylamine

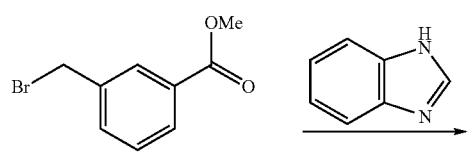

-continued

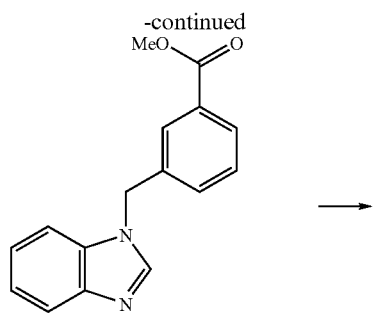

Using essentially the same procedure described in Example 1 and employing methyl 3-bromomethyl)benzoate in step 1 and the appropriate pyrrolidin-3-yl- or piperidin-3-yl-amine in Step 3, the compounds shown on Table II were obtained and identified by HPLC and mass spectral analyses or by $^1$H NMR and mass spectral analyses.

TABLE II

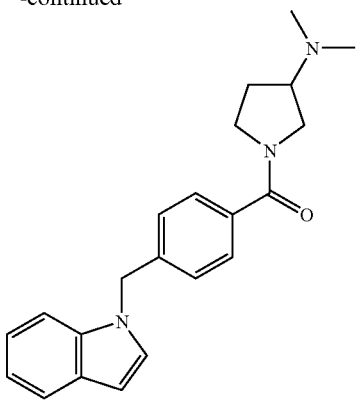

| Ex. No. | p | NR1R2 | [M + H] | Time (Min.) |
|---|---|---|---|---|
| 8 | 1 | dimethylamine | 349.3 | 3.96 |
| 9 | 2 | pyrrolidine | 389.2 | — |
| 10 | 2 | 2-methylpyrrolidine | 403.3 | — |
| 11 | 2 | piperidine | 403.3 | — |

EXAMPLE 12

Preparation of 1-[4-(1H-Indol-1-ylmethyl)benzoyl]-N,N-dimethylpyrrolidin-3-ylamine

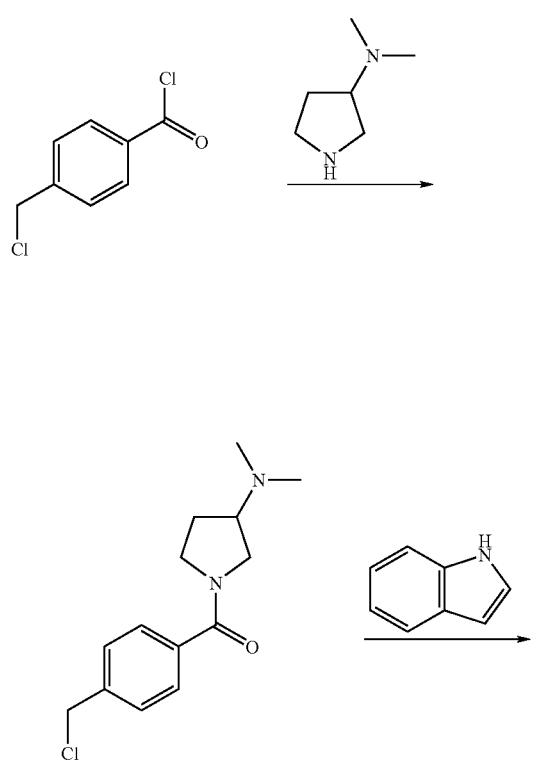

Step 1. A solution of 3-(dimethylamino)pyrrolidine (2.5 g, 22 mmol) in acetonitrile is added to an ice cold solution of 4-(chloromethyl)benzoyl chloride (5.0 g, 26 mmol) in acetonitrile, stirred while warming to room temperature for 2 hours then concentrated in vacuo. The resultant residue is suspended in ether and filtered to give 1-(4-chloromethylbenzoyl)-3-(N,N-dimethylamino)pyrrolidine hydrochloride as a white solid identified by NMR and MS [267 m/e (M+H)].

Step 2. A solution of indole (29 mg, 0.25 mmol) in DMF (5 mL) at room temperature is treated with sodium hydride (30 mg), stirred for 10 minutes, treated with 1-(4-chloromethylbenzoyl)-3-(N,N-dimethylamino)pyrrolidine hydrochloride (113 mg, 0.37 mmol) stirred at room temperature overnight and concentrated in vacuo. The resultant residue is dissolved in a mixture of DMSO, MeOH and water (1.5 mL) and purified by reverse-phase semi-preparative HPLC to give the title product as a white powder (63 mg), identified by HPLC and mass spectral analyses. MS [348.2 m/e (M+H)], retention time 2.58 min.

EXAMPLES 13-39

Preparation of N,N-Dimethyl1-[4-(1H-indol-1-ylmethyl)benzoyl]pyrrolidin-3-ylamine

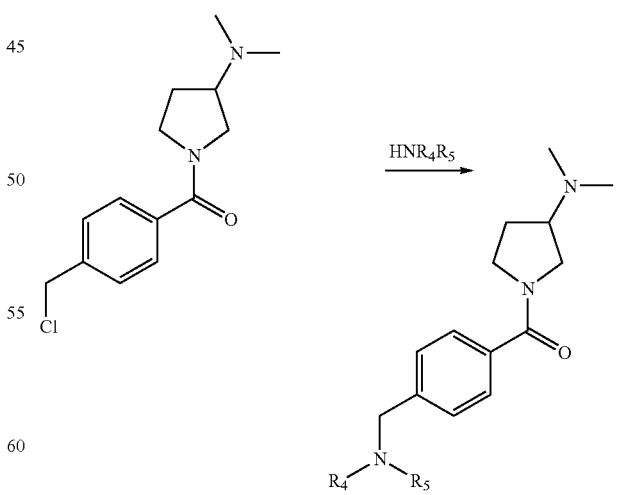

Using essentially the same procedure described in Example 12 and employing the appropriate bicyclic amine, HNR4R5, in step 2, the compounds shown in Table III are obtained and identified by HPLC and mass spectral analyses.

TABLE III

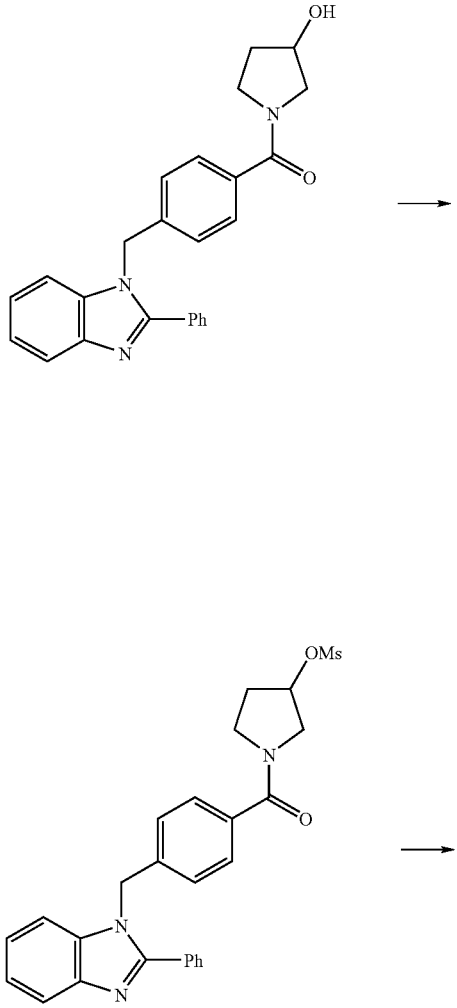

| Ex. No. | NR4R5 | [M + H] | Time (Min.) |
|---|---|---|---|
| 13 | 2,3,4,9-tetrahydro-1H-carbazole | 402.2 | 2.89 |
| 14 | N,N-diethyl-2,3,4,9-tetrahydro-1H-carbazole-3-carboxamide | 501.3 | 2.64 |
| 15 | ethyl 2,3,4,9-tetrahydro-1H-carbazole-3-carboxylate | 474.3 | 2.81 |
| 16 | 2,3,4,9-tetrahydro-1H-carbazole-3-carboxylic acid | 446.2 | 2.64 |
| 17 | 2-methylindole | 362.2 | 2.67 |
| 18 | 2-phenylindole | 424.2 | 2.86 |
| 19 | 5-methoxyindole | 378.2 | 2.53 |
| 20 | 2-methyl-5-methoxyindole | 392.2 | 2.62 |
| 21 | 5-methoxy-2-phenylindole | 454.2 | 2.83 |
| 22 | 11b-methyl-5,6,11,11b-tetrahydro-1H-indolizino[8,7-b]indol-3(2H)-one | 471.3 | 2.37 |
| 23 | 1,1-dimethyl-1,3,4,9-tetrahydropyrano[3,4-b]indole | 432.3 | 2.65 |
| 24 | 7-azaindole | 664 | 2.20 |
| 25 | 1H-Benzo[d]imidazole | 382 | 2.10 |
| 26 | 1H-imidazo[4,5-b]pyridine | 353 | 1.90 |
| 27 | Indoline | 429 | 2.30 |
| 28 | 2-methylbenzo[d]imidazole | 508 | 2.50 |
| 29 | 5-hydroxyindole | 312 | 1.60 |
| 30 | 1,2,3,4-tetrahydroquinoline | 328 | 1.70 |
| 31 | 5-fluoroindole | 341 | 1.70 |
| 32 | 3-cyanoindole | 341 | 1.70 |
| 33 | 2-phenyl-1H-imidazole | 659 | 2.00 |
| 34 | 6-methyl-1,2,3,4-tetrahydroquinoline | 348 | 1.60 |
| 35 | 1-methyl-9H-pyrido[3,4-b]indole | 424 | 2.10 |
| 36 | 2-(2-pyridyl)-benzo[d]imidazole | 503 | 2.30 |
| 37 | 10,11-dihydro-5H-dibenzo[b,f]azepine | 426.2 | 2.08 |
| 38 | 5-bromoindoline | 428.1 | 2.00 |
| 39 | 5-bromoindole | 426.1 | 1.96 |

EXAMPLE 40

Preparation of N-Ethyl-N-methyl-1-{4-[(2-phenyl-1H-benzimidazol-1-yl)methyl]benzoyl}pyrrolidin-3-amine

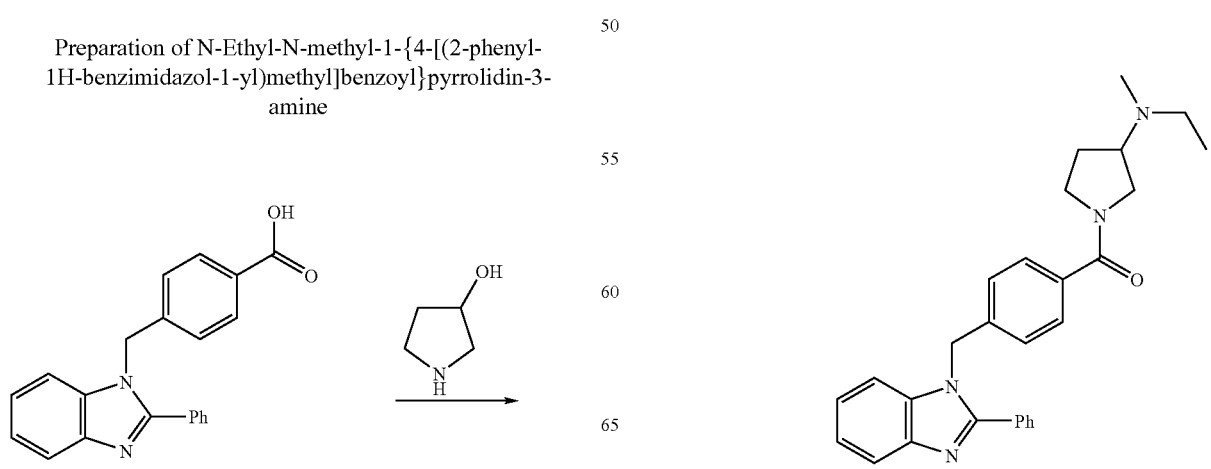

Step 1. A solution of 4-(2-phenyl-benzoimidazol-1-ylmethyl)-benzoic acid (1 g, 3 mmol) in DCM is treated with 2drops of DMF followed by oxalylchloride (3 mL, 6 mmol, 2M solution in DCM), stirred at room temperature for 2 hours and concentrated in vacuo. The resultant residue is dissolved in DCM, treated with 3-pyrrolidinol (0.3 mL, 3.6 mmol), stirred at room temperature for 8 hours then concentrated to give 1-{4-[(2-phenyl-1H-benzimidazol-1-yl)methyl]benzoyl}pyrrolidin-3-ol identified by HPLC and MS [398.4 m/e (M+H)].

Step 2. A solution of 1-{4-[(2-phenyl-1H-benzimidazol-1-yl)methyl]benzoyl}pyrrolidin-3-ol (0.85 g, 3 mmol) in DCM at 0° C. is treated with and triethylamine (0.91 mL, 6.6 mmol) followed by methylsulfonyl chloride (0.25 mL, 3.3 mmol), stirred at room temperature overnight and concentrated togive methanesulfonic acid 1-[4-(2-phenyl-benzoimidazol-1-ylmethyl)-benzoyl]-pyrrolidin-3-yl ester as a white powder (1.4 g) identified by HPLC and MS [476.3 m/e (M+H)].

Step 3. A solution of methanesulfonic acid 1-[4-(2-phenyl-benzoimidazol-1-ylmethyl)-benzoyl]-pyrrolidin-3-yl ester (71 mg, 0.15 mmol) in DMF is treated with N-ethylmethylamine (0.038 mL, 0.45 mmol), stirred at room temperature overnight and concentrated in vacuo. The resultant residue is dissolved in a mixture of DMSO, MeOH and water (1.5 mL) and purified by reverse-phase semi-preparative HPLC[1] to give the title product as a white powder (6.4 mg), identified by HPLC[2] and MS [439.6 m/e (M+H)], retention time 1.48 min.

TABLE IV

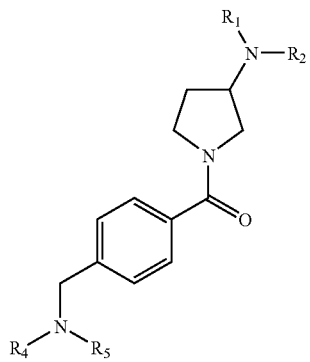

| Ex. No. | NR1R2 | NR4R5 | [M + H] | Time (Min.) |
|---|---|---|---|---|
| 46 | 2-methylpyrroldine | 2-phenyl-1H-benzimidazole | 465.6 | 1.53 |
| 47 | pyrrolidine | 6-chloro-1H-benzimidazole | 423.1 | — |
| 48 | pyrrolidine | 2-(trifluoromethyl)-1H-benzimidazole | 443.1 | — |
| 49 | piperidine | 1H-benzimidazole | 389.2 | — |
| 50 | 3-methylpiperidine | 1H-benzimidazole | 403.2 | — |
| 51 | 2-methylpiperidine | 1H-benzimidazole | 403.2 | — |
| 52 | N-methylpropylamine | 1H-benzimidazole | 377.2 | — |
| 53 | (R)-pyrrolidine | 2-(trifluoromethyl)-1H-benzimidazole | 443.2 | — |
| 54 | pyrrolidine | 6-fluoro-1H-benzimidazole | 393.3 | 4.74 |
| 55 | pyrrolidine | 1H-benzimidazole | 375.1 | — |
| 56 | 3-methylpiperidine | 1H-benzimidazole | 403.2 | — |
| 57 | N-methylpropylamine | 1H-benzimidazole | 377.2 | — |
| 58 | piperidine | 6-fluoro-1H-benzimidazole | 407.1 | 4.8 |
| 59 | pyrrolidine | 6-methyl-1H-benzimidazole | 389.3 | 4.4 |
| 60 | piperidine | 6-methyl-1H-benzimidazole | 403.3 | 4.7 |
| 61 | N,N-diethylamine | 1H-benzimidazole | 377.2 | — |
| 62 | N-methylethylamine | 6-methyl-1H-benzimidazole | 377.3 | 4.38 |
| 63 | N-methylethylamine | 6-fluoro-1H-benzimidazole | 381.3 | 3.35 |
| 64 | N-methylethylamine | 5-fluoro-1H benzimidazole | 381.3 | 4.39 |
| 65 | pyrrolidine | 5-fluoro-1H-benzimidazole | 393.3 | 4.46 |
| 66 | piperidine | 5-fluoro-1H-benzimidazole | 407.3 | 4.565 |
| 67 | N-methylethylamine | 4-fluoro-1H-benzimidazole | 381.3 | 4.75 |
| 68 | pyrrolidine | 4-fluoro-1H-benzimidazole | 393.3 | 4.67 |

EXAMPLES 41-85

Preparation of N-Substituted-1-[(heteroarylmethyl)benzoyl]pyrrolidin-3-ylamine Compounds

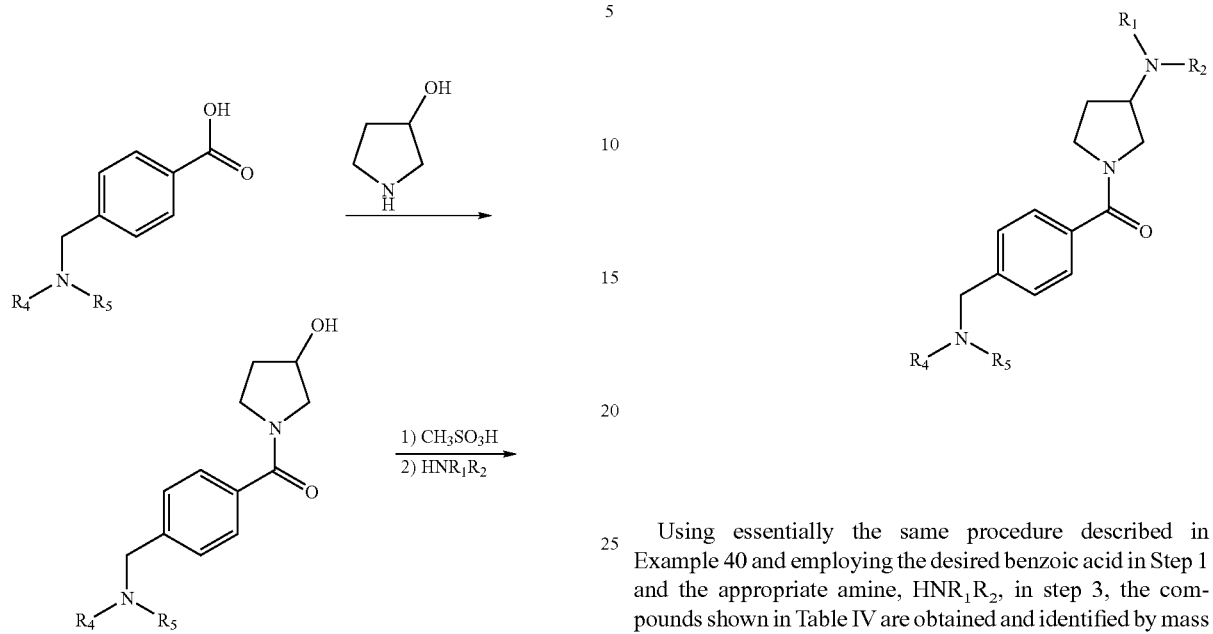

Using essentially the same procedure described in Example 40 and employing the desired benzoic acid in Step 1 and the appropriate amine, $HNR_1R_2$, in step 3, the compounds shown in Table IV are obtained and identified by mass spec and either HPLC or $^1H$ NMR analyses.

TABLE IV

| Ex. No. | NR1R2 | NR4R5 | [M + H] | Time (Min.) |
|---|---|---|---|---|
| 41 | pyrrolidine | 2-phenyl-1H-benzimidazole | 451.6 | 1.50 |
| 42 | N-methylethanolamine | 2-phenyl-1H-benzimidazole | 455.6 | 1.45 |
| 43 | N-methyl1-(furan-2-yl)-N-methyl-methanamine | 2-phenyl-1H-benzimidazole | 491.6 | 1.58 |
| 44 | 3,5-dimethylpipendine | 2-phenyl-1H-benzimidazole | 493.7 | 1.62 |
| 45 | cis-2,6-dimethylmorpholine | 2-phenyl-1H-benzimidazole | 495.6 | 1.55 |
| 69 | piperidine | 4-fluoro-1H benzimidazole | 407.3 | 4.84 |
| 70 | (S)-pyrrolidine | 6-fluoro-1H-benzimidazole | 393.3 | 4.81 |
| 71 | (R)-N-methylethylamine | 1H-benzimidazole | 363.2 | — |
| 72 | (R)-piperidine | 1H-benzimidazole | 389.2 | — |
| 73 | (R)-piperidine | 2-methyl-1H-benzimidazole | 403.2 | — |
| 74 | (S)-piperidine | 1H-benzimidazole | 389.2 | — |
| 75 | (S)-piperidine | 2-methyl-1H-benzimidazole | 403.3 | — |
| 76 | (2R,5R)-2,5-dimethypyrrolidine | 2-methyl-1H-benzimidazole | 417.2 | — |
| 77 | (R)-2-methylpyrrolidine | 2-methyl-1H-benzimidazole | 403.2 | — |
| 78 | 3,5-dimethylpiperidine | 2-methyl-1H-benzimidazole | 431.2 | — |
| 79 | (R)-2-methylpyrrolidine | 1H-benzimidazole | 389.2 | — |
| 80 | (R)-pyrrolidine | 1H-benzimidazole | 375.2 | — |
| 81 | (R)-pyrrolidine | 2-methyl-1H benzimidazole | 389.2 | — |

TABLE IV-continued

| Ex. No. | NR1R2 | NR4R5 | [M + H] | Time (Min.) |
|---|---|---|---|---|
| 82 | (S)-2-methylpyrrolidine | 2-methyl-1H-benzimidazole | 289.2 | — |
| 83 | (S)-2-methylpyrrolidine | 2-methyl-1H-benzimidazole | 403.2 | — |
| 84 | 4-methylpiperidine | 1H-benzimidazole | 403 | |
| 85 | (S)-pyrrolidine | 2-(trifluoromethyl)-1H-benzimidazole | 479.9 | |

EXAMPLES 86-88

Preparation of N-Substituted-1-[3-(1H-benzimidazol-1-yl)methyl)benzoyl]-pyrrolidin-3-ylamine Compounds

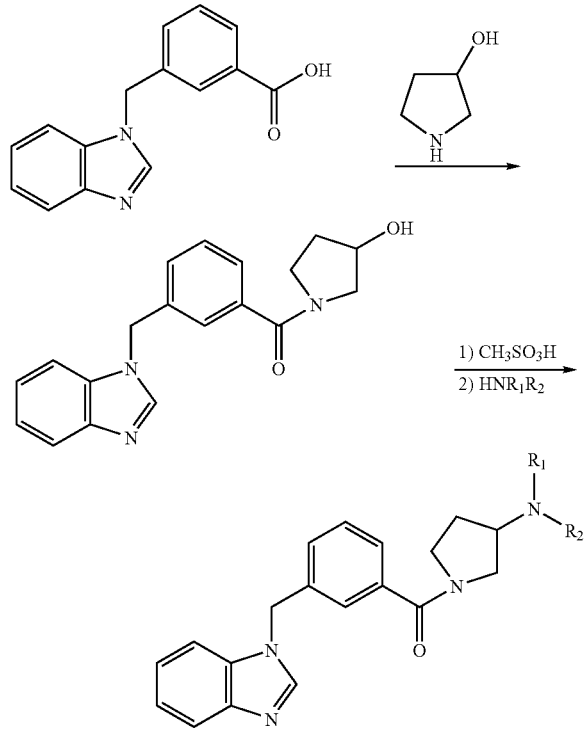

Using essentially the same procedure described in Example 40 and employing 3-(benzimidazol-1-ylmethyl)benzoic acid in Step 1 and the appropriate amine, HNR₁R₂, in step 3, the compounds shown in Table V are obtained and identified by HPLC and mass spectral analyses.

TABLE V

| Ex. No. | NR1R2 | [M + H] | Time (Min.) |
|---|---|---|---|
| 86 | N-methylethylamine | 363.2 | 4.71 |
| 87 | pyrrolidine | 375.2 | 4.73 |
| 88 | piperidine | 389.3 | 4.82 |

EXAMPLES 89 AND 90

Preparation of N-Substituted-1-[2-(1H-benzimidazol-1-yl)methyl)benzoyl]-pyrrolidin-3-ylamine Compounds

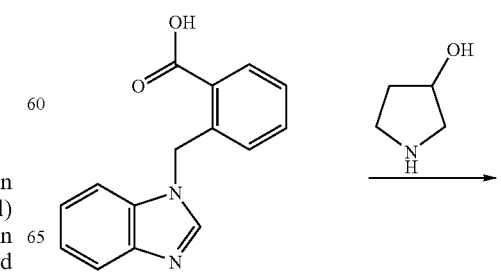

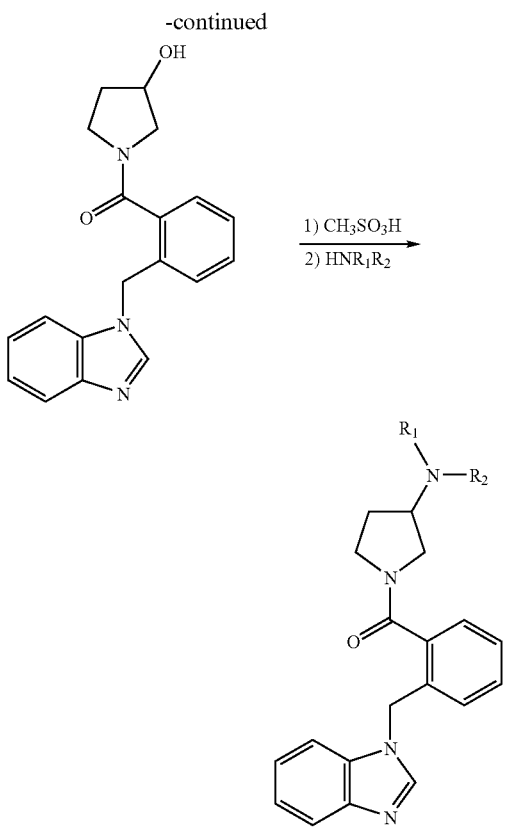

Using essentially the same procedure described in Example 40 and employing 2-(benzimidazol-1-ylmethyl)benzoic acid in Step 1 and the appropriate amine, $HNR_1R_2$, in step 3, the compounds shown in Table VI are obtained and identified by HPLC and mass spectral analyses.

TABLE VI

| Ex. No. | $NR_1R_2$ | [M + H] | Time (Min.) |
|---|---|---|---|
| 89 | piperidine | 389.2 | 4.70 |
| 90 | pyrrolidine | 375.3 | 4.87 |

EXAMPLE 91

Preparation of 1'-{4-[(5-methyl-1H-benzimidazol-1-yl)methyl]benzoyl}-1,3'-bipyrrolidine Hydrochloride

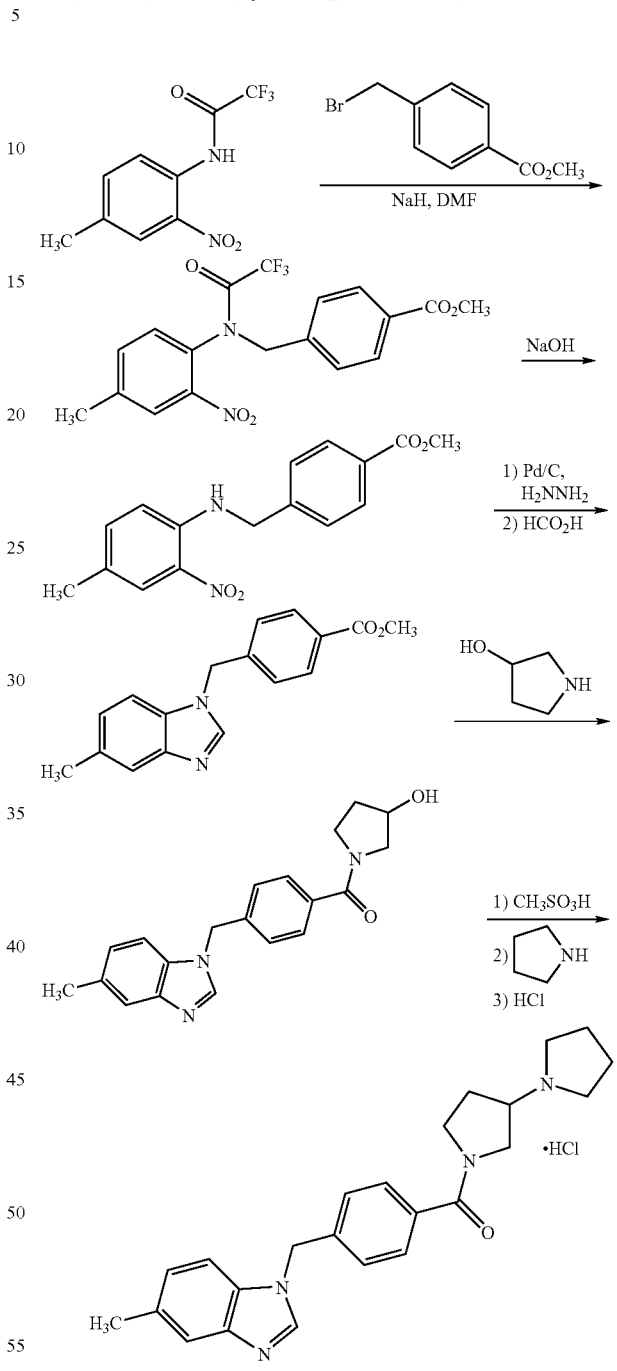

Step 1) 4-{[(4-Methyl-2-nitrophenyl)-(2,2,2-trifluoroacetyl)amino]methyl}-benzoic acid methyl ester A portion of 60% NaH in mineral oil (2.9 g, 71.8 mmol, 1.1 eq) was pre-washed with hexane and suspended in dry DMF under nitrogen. The slurry was cooled in an ice bath and a solution of 2,2,2-trifluoro-N-(4-methyl-2-nitrophenyl)-acetamide (16.2 g, 65.3 mmol, 1.0 eq) in dry DMF was added dropwise over 15 min. The cooling bath was removed and the mixture was stirred for 30 min. The reaction mixture was cooled again and a solution of 4-bromomethylbenzoic acid methyl ester (20 g, 65.3 mmol, 1.0 eq) in dry DMF was added dropwise over 10 min. The reaction mixture was stirred at room temperature for 18 h and evaporated under reduced pressure to give a residue. The residue was partitioned between ethyl acetate and water. The organic layer was washed sequentially with water and brine, dried ($Na_2SO_4$) and concentrated to give a yellow solid. The yellow solid was purified by column chromatography. (Silica gel 230-400 mesh: eluent $CHCl_3$ MeOH:0→5%) to give 4-{[(4-methyl-2-nitrophenyl)-(2,2,2-trifluoroacetyl)amino]methyl}benzoic acid methyl ester, yield: 59%. $^1$H NMR (400 MHz, $CDCl_3$): 7.97 (m, 3H); 7.27 (m, 3H); 6.76 (d, J=8 Hz, 1H); 5.66 & 4.26(2H); 3.92 (s, 3H); 2.46(s, 3H).

Step 2)
4-[(4-Methyl-2-nitrophenylamino)methyl]benzoic acid methyl ester

A stirred solution of 4{[(4-methyl-2-nitrophenyl)(2,2,2-trifluoroacetyl)-amino]methyl}benzoic acid methyl ester (14.0 g, 35 mmol) in $CH_2Cl_2$, was treated with tetrabutylammonium bromide (1.13 g, 3.5 mmol) and 20% aq. KOH (100 mL). The reaction mixture was heated to 38° C. for 3 h and cooled to room temperature. The phases were separated, the aqueous phase was extracted with $CH_2Cl_2$. The combined extracts and organic phase were washed with brine, dried over anhydrous $Na_2SO_4$ and concentrated in vacuo to afford 4-[(4-methyl-2-nitrophenylamino)methyl]-benzoic acid methyl ester as an orange solid. Yield: 90%. $^1$H NMR (400 MHz, $CDCl_3$): 8.37 (bs, 1H); 8.02 (m, 3H); 7.40 (d, J=8 Hz, 2H); 7.19 (d, J=8 Hz, 1H); 6.63(d, J=8 Hz, 1H); 4.60(d, J=8 Hz, 2H); 3.91(s,3H); 2.35 (s, 1H).

Step 3)
4-[(5-Methylbenzimidazol-1-yl)methyl]benzoic acid methyl ester

A stirred solution 4-[(4-methyl-2-nitrophenylamino)methyl]benzoic acid methyl ester (7.0 g, 23 mmol,) in $CH_3OH$ was treated with 5% Pd/C (50% wet, 30% w/w) and hydrazine hydrate (5.8 g, 116 mmol). The reaction mixture was heated to reflux temperature for 2 h, cooled to room temperature and filtered through celite. The filtrate was evaporated to give a residue. The residue was dissolved in $CH_2Cl_2$, washed with water, dried over anhydrous $Na_2SO_4$ and evaporated to afford 4-[(2-amino-4-methylphenylamino)methyl]benzoic acid methyl ester, which was used in the next step without further purification. Yield: 93%. $^1$H NMR (400 MHz, $CDCl_3$) 8.0 (d, J=8 Hz, 2H); 7.70 (d, J=8 Hz, 2H); 6.60 (m, 2H); 6.49 (d, 1H); 4.3 (s, 2H); 3.90 (d, 3H); 2.21 (s, 3H). LCMS (ESI$^+$) 271 (MH+). A stirred solution of crude 4-[(2-amino-4-methylphenylamino)methyl]benzoic acid methyl ester (6 g, 22 mmol) in trimethylorthoformate was treated with formic acid (1.0 g), refluxed for 2 h, cooled to room temperature and evaporated under reduced pressure. The resultant residue was purified by column chromatography using 1% MeOH/$CHCl_3$ to afford 4-[(5-methylbenzimidazol-1-yl)methyl]benzoic acid methyl ester Yield: 61%. $^1$H NMR (400 MHz, $CDCl_3$): 8.0 (d, J=8 Hz, 1H); 7.93 (s, 1H); 7.62 (s, 1H); 7.26 (s, 1H); 7.21 (d, J=8 Hz, 2H); 7.08 (m, 2H); 5.39 (s, 2H); 3.90 (s, 3H); 2.47 (s, 3H). LCMS (ESI$^+$) 281 (MH+).

Step 4) Methanesulfonicacid 1-{[4-(5-methylbenzimidazol-1-yl)methyl]benzoyl}-pyrrolidin-3-yl ester Hydrolyzing 4-[(5-methylbenzimidazol-1-yl)methyl]benzoic acid methyl ester to the corresponding benzoic acid and using essentially the same procedure described in Example 37, steps 1 and 2, methanesulfonicacid 1-{[4-(5-methylbenzimidazol-1-yl)methyl]benzoyl}pyrrolidin-3-yl ester was obtained. $^1$H NMR (400 MHz, $CDCl_3$): 7.93 (s, 1H); 7.62 (s, 1H); 7.46-7.53 (m, 2H); 7.07-7.22 (m, 4H); 5.37 (s, 2H); 5.37 & 5.24 (bs, 1H); 3.55-3.93 (m, 4H); 3.08 & 3.01 (s, 3H); 2.47 (s, 3H); 2.17-2.34 (m, 2H). LCMS (ESI$^+$) 414 (MH+).

Step 5) 1'-{4-[(5-methyl-1H-benzimidazol-1-yl)methyl]benzoyl}-1,3'-bipyrrolidine Hydrochloride Using essentially the same procedure described in Example 37, step 3 and employing methanesulfonicacid 1-{[4-(5-methylbenzimidazol-1-yl)methyl]benzoyl}-pyrrolidin-3-yl ester and pyrrolidine as starting materials, the title product was obtained and identified by NMR and mass spectral analyses. $^1$H NMR (300 MHz, 353K, DMSO-$d_6$): 11.81 (s br, 1H); 9.64(s, 1H); 7.72(d, 1H); 7.68(m, 1H); 7.57(d, 2H); 7.50(d, 2H); 7.39(dd, 1H); 5.78(s, 2H); 3.97-3.67(m, 4H); 3.52-2.95(m br, 5H); 2.50(s, 3H); 2.29(m, 2H); 2.05-1.91 (m, 4H). LCMS (ESI$^+$) 389.3 (MH+).

EXAMPLES 92-117

Preparation of 1'-{4-[(Substituted-1H-benzimidazol-1-yl)methyl]benzoyl}-pyrrolidin-3-yl amines

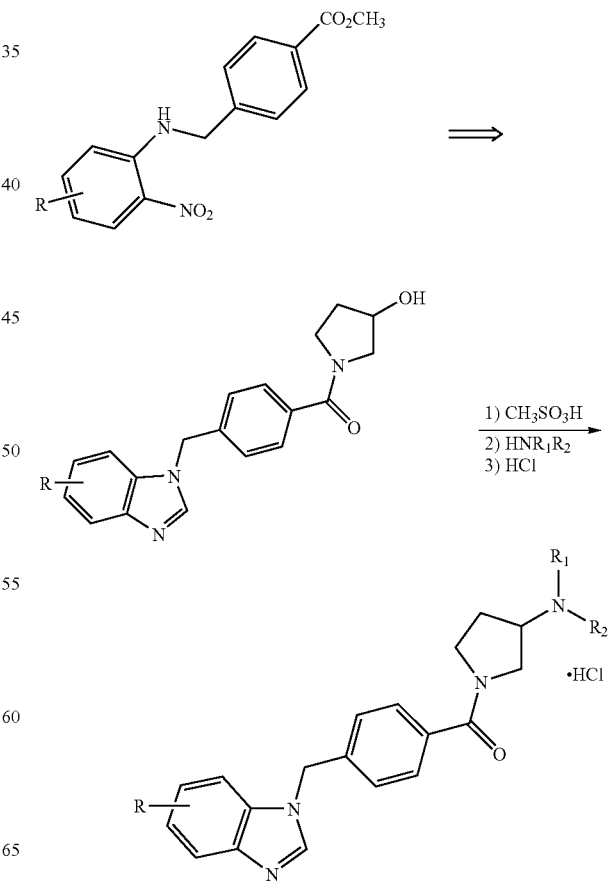

Using essentially the same procedure described in Example 91 and employing the appropriately substituted ortho-nitrobenzamide in Step 1 and the desired amine, $HNR_1R_2$ in Step 5, the compounds shown on Table VII were obtained and identified by $^1H$ NMR and mass spectral analyses.

TABLE VII

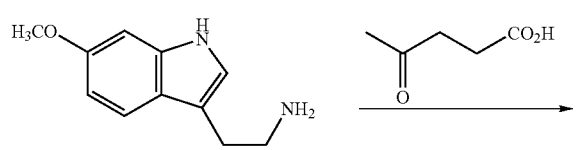

| Ex. No. | R | NR1R2 | [M + H] |
|---|---|---|---|
| 92 | 5-CH₃ | piperidine | 403.4 |
| 93 | 4-F | piperidine | 393.4 |
| 94 | 5-CH₃ | 2-methylpiperidine | 417.4 |
| 95 | 5-CH₃ | morpholine | 405.3 |
| 96 | 5-CH₃ | 4-methylpiperidine | 417.4 |
| 97 | 5-CH₃ | 4-methylpiperazine | 418.3 |
| 98 | 5-CH₃ | 3-methylpiperazine | 417.3 |
| 99 | 5-CH₃ | (2S)-2-(hydroxymethyl)pyrrolidinemethyl | 419.3 |
| 100 | 5-CH₃ | dimethylamine | 363.3 |
| 101 | 5-CH₃ | ethylmethylamine | 377.3 |
| 102 | 5-CH₃ | 2-benzylpyrrolidine | 479.4 |
| 103 | 7-CH₃ | pyrrolidine | 389.3 |
| 104 | 5-F | (2R)-2-methylpyrrolidine | 407.4 |
| 105 | 5-CH₃ | (2R)-2-methylpyrroiidine | 403.4 |
| 106 | 5-F | (2S)-2-methylpyrrolidine | 407.3 |
| 107 | 5-CH₃ | azapane | 417.3 |
| 108 | 5-CH₃ | 4-methyl-1,4-diazapane | 432.2 |
| 109 | 5-F | (3'S)-pyrrolidine | 393.2 |
| 110 | 7-CH₃ | piperidine | 403.3 |
| 111 | 5-CH₃ | azetidine | 355.3 |
| 112 | 7-F | (3'S)-pyrrolidine | 393.2 |
| 113 | 7-F | azapane | 421.2 |
| 114 | 7-F | (3S)-piperidine | 407.2 |
| 115 | 7-F | (3S)-ethylmethylamine | 381.2 |
| 116 | 7-F | (3S)3-methyl-piperidine | 421.2 |
| 117 | 7-F | (3S)-azetidine | 379.2 |

EXAMPLE 118

Preparation of 11-(4-{[3-(Dimethylamino)pyrrolidin-1-yl]carbonyl}benzyl)-9-methoxy-11b-methyl-1,2,5,6,11,11b-hexahydro-3H-indolizino[8,7-b]indol-3-one

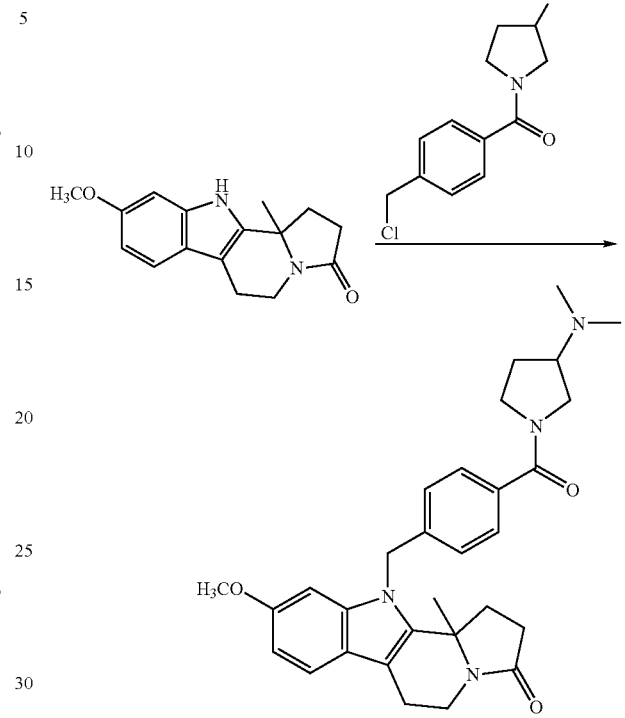

Step 1. A mixture of 6-methoxytryptamine (0.95 g, 5 mmol) and levulinic acid (0.7 g, 6 mmol) in ethoxyethanol is heated at ruflux temperature for 16 hours, cooled to room temperature and concentrated in vacuo to give 9-methoxy-11b-methyl-1,2,5,6,11,11b-hexahydro-indolizino[8,7-b]indol-3-one (0.97 g) identified by NMR, HPLC and MS [271.2 m/e (M+H)].

Step 2. A solution of 9-methoxy-11b-methyl-1,2,5,6,11,11b-hexahydro-indolizino[8,7-b]indol-3-one (54 mg, 0.2 mmol) in DMF is treated with sodium hydride (50 mg), stirred at room temperature for 10 minutes, treated with (4-chloromethyl-benzoyl)-N,N-dimethylaminopyrrolidin-3-amine hydrochloride (72 mg, 0.24 mmol), stirred at room temperature overnight and concentrated in vacuo. The resultant residue is dissolved in a mixture of DMSO, MeOH and water (1.5 mL) and purified by reverse-phase semi-preparative HPLC¹ to give the title product as a white powder (49 mg), identified by HPLC and MS [501.7 m/e (M+H)].

EXAMPLES 119-126

Preparation of 11-(4-{[3-(Dimethylamino)pyrrolidin-1-yl]carbonyl}benzyl)-9,11b-disubstituted-1,2,5,6,11,11b-hexahydro-3H-indolizino[8,7-b]indol-3-one Compounds

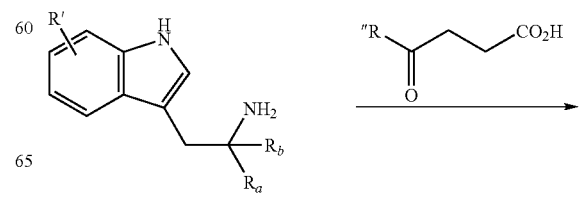

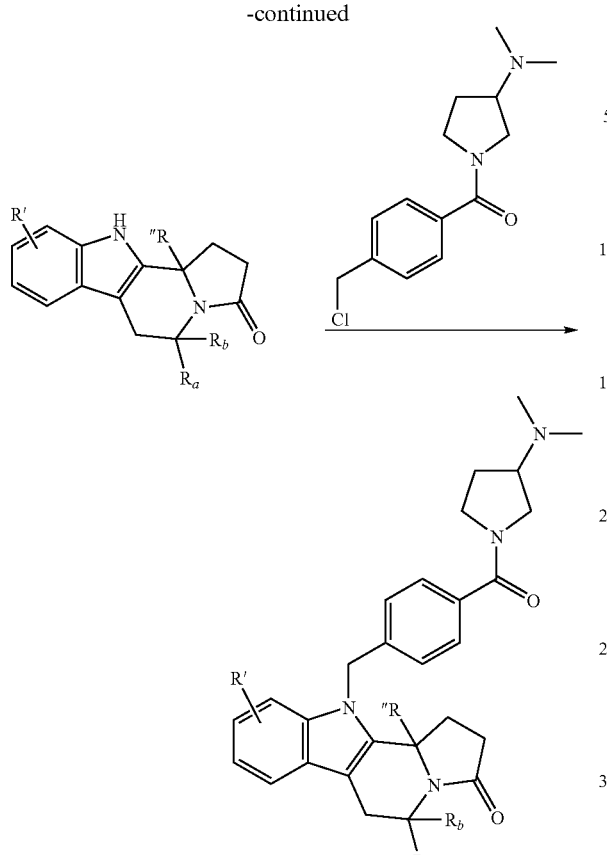

Using essentially the same procedure described in Example 118 and employing the appropriately substituted tryptamine and levulinic acid in Step 1, the compounds shown in Table VIII are obtained and identified by mass spectral and HPLC analyses.

TABLE VIII

| Ex. No. | R' | Ra | Rb | R'' | [M + H] | Time (Min.) |
|---|---|---|---|---|---|---|
| 119 | H | H | H | methyl | 501.3 | 1.80 |
| 120 | 5,5-dimethyl | H | H | methyl | 485.3 | 1.86 |

TABLE VIII-continued

| Ex. No. | R' | Ra | Rb | R'' | [M + H] | Time (Min.) |
|---|---|---|---|---|---|---|
| 121 | H | CH₃ | CH₃ | methyl | 499.3 | 1.98 |
| 122 | 5-methyl | H | H | ethyl | 485.3 | 1.85 |
| 123 | 8-benzyloxy | H | H | methyl | 485.7 | 1.88 |
| 124 | 9-methoxy | H | H | methyl | 577.8 | 2.06 |
| 125 | 9-fluoro | H | H | methyl | 489.6 | 1.86 |
| 126 | 10-methyl | H | H | methyl | 485.7 | 1.73 |

EXAMPLE 127

Preparation of (3'S)-1'-[4-(1H-indol-1-ylmethyl) benzoyl]-1,3'-bipyrrolidine

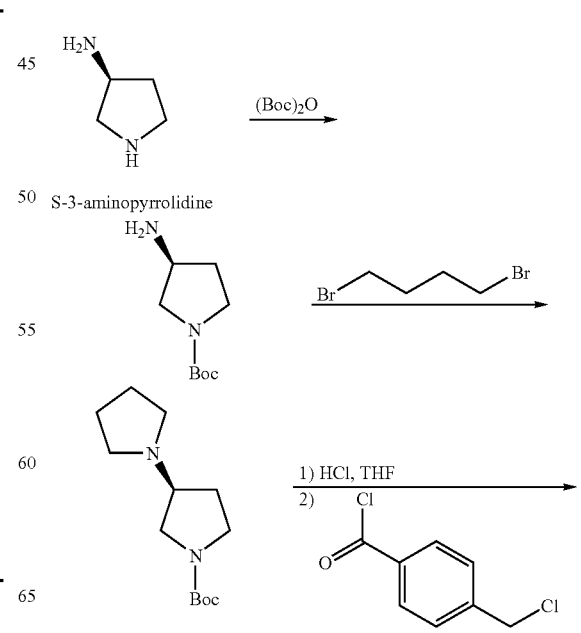

-continued

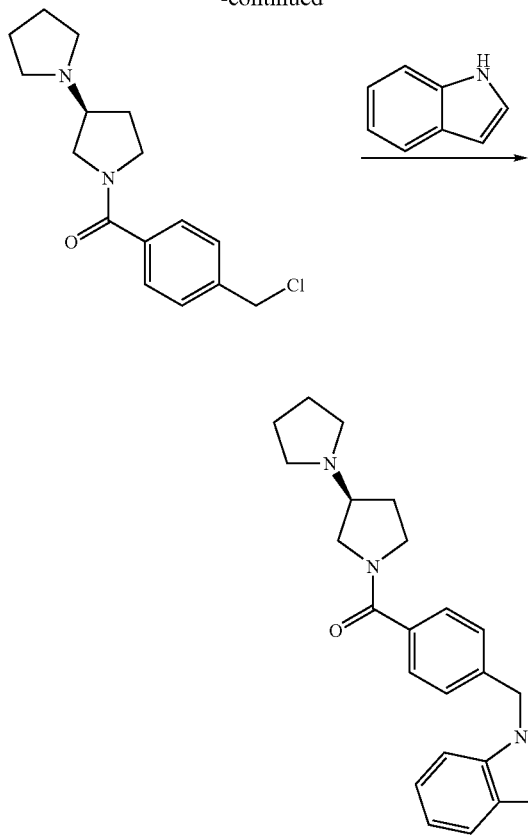

Step 1. A solution of (S)-3-aminopyrrolidine (1 mL, 11.6 mmol) in MeOH at 0° C. is treated with di-tert-butyl dicarbonate [(Boc)$_2$O] (2.5 g, 1 eq), stirred at room temperature overnight and concentrated in vacuo to give a residue.

Step 2. A solution of the residue from Step 1 toluene is treated with 1,4-dibromobutane (13.9 mmol, 1.7 mL) and K$_2$CO$_3$ (3.2 g, 23.2 mmol), stirred at 110° C. overnight, cooled to room temperature, diluted with EtOAc, washed with water, dried over MgSO$_4$, and concentrated in vacuo to give Boc-pyrrolidino-pyrrolidine.

Step 3. A mixture of Boc-pyrrolidino-pyrrolidine (1 g, crude, 4.2 mmol) from step 2 and 2 N HCl in dioxane is stirred at room temperature for 3 h and concentrated to a thick oil. The oil is dissolved in DCM, cooled to 0° C., treated with diisopropylethylamine (5 eq) and 4-(chloromethyl)benzoyl chloride (0.8 g, 4.2 mmol), stirred while warming to room temperature for 2 h, diluted with EtOAc, washed with saturated. NaHCO$_3$, dried over MgSO$_4$ and concentrated in vacuo to give [1,3']bipyrrolidinyl-1'-yl-(4-chloromethyl-phenyl)-methanone as a brown oil (1.3 g), identified by HPLC and MS [293 m/e (M+H)].

Step 4. A solution of indole (0.15 mmol, 19 mg) in a mixture of DMF/THF (1:4, 2 mL) is treated with sodium hydride (50 mg) followed by [1,3']bipyrrolidinyl-1'-yl-(4-chloromethyl-phenyl)-methanone (0.15 mmol, 43 mg), stirred at room temperature overnight and concentrated in vacuo. The resultant residue is dissolved in a mixture of DMSO, MeOH and water (1.5 mL) and purified by reverse-phase semi-preparative HPLC[1] to give the title product as a white powder (8 mg), identified by HPLC and mass spectral analyses. Retention time 1.86 min., MS [374.2 m/e (M+H)].

EXAMPLES 128-144

Preparation of (3'S)-1'-[4-(Heteroarylalkyl)benzoyl]-1,3'-bipyrrolidine

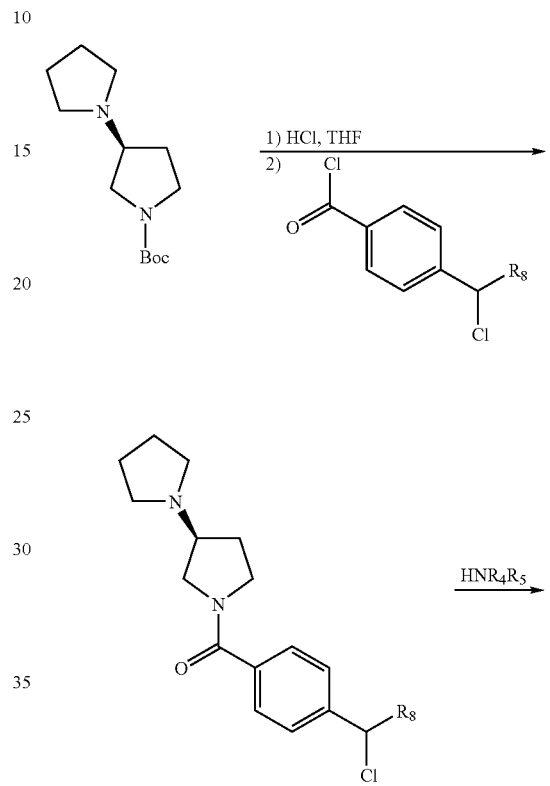

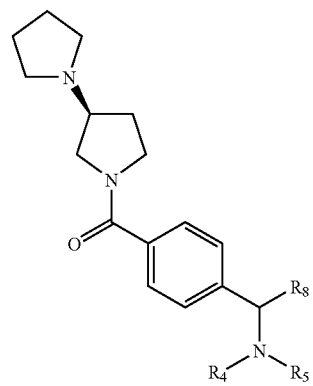

Using essentially the same procedure described in Example 127 and employing the appropriately substituted 4-chloromethylbenzoyl chloride in Step 3 and the desired cyclic amine, HNR$_4$R$_5$, in Step 4, the compounds shown in Table IX are obtained and identified by mass spec and either $^1$H NMR or HPLC analyses. Those compounds on Table IX wherein R$_8$ is an (R) or (S) enantiomer were obtained by chiral separation of the corresponding racemic compound using standard chiral HPLC techniques.

TABLE IX

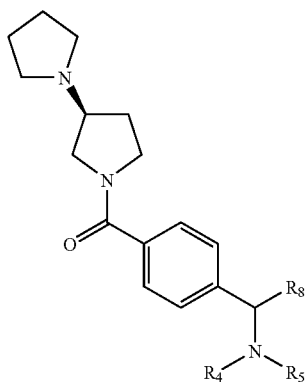

| Ex. No. | NR4R5 | R8 | [M + H] | Time (Min.) |
|---|---|---|---|---|
| 128 | indazole | H | 375.2 | 1.74 |
| 129 | 1H-benzimidazole | H | 375.2 | 1.29 |
| 130 | 4-aza-1H-benzimidazole | H | 376.2 | 1.88 |
| 131 | indoline | H | 376.2 | 1.86 |
| 132 | 7-azaindole | H | 375.2 | 1.68 |
| 133 | 2-methyl-1H-benzimidazole | H | 389.2 | 1.28 |
| 134 | 6-chloroindole | H | 408.2 | 1.98 |
| 135 | 5-chloroindole | H | 408.2 | 1.99 |
| 136 | 7-chloroindole | H | 408.2 | 1.97 |
| 137 | 9H-carbazole | H | 424.2 | 2.06 |
| 138 | 2,3,4,9-tetrahydro-1H-carbazole | H | 428.3 | 2.12 |
| 139 | 2-phenylindole | H | 450.2 | 2.15 |
| 140 | 2-methyl-1H-benzimidazole | CH$_3$ | 403.2 | — |
| 141 | 2-methyl-1H-benzimidazole | (S)-CH$_3$ | 403.3 | — |
| 142 | 2-methyl-1H-benzimidazole | (R)-CH$_3$ | 403.2 | — |
| 143 | 1H-benzimidazole | CH$_3$ | 389.2 | — |
| 144 | 1H-benzimidazoie | (S)-CH$_3$ | 389.2 | — |
| 145 | 1H-benzimidazole | (R)-CH$_3$ | 389.2 | — |
| 146 | 7-chloro-1H-benzimidazole | CH$_3$ | 422.2 | — |
| 147 | 5-chloro-2-methyl-1H-benzimidazole | H | 460.4 | |
| 148 | 6-chloro-2-methyl-1H-benzimidazole | H | 460.4 | |
| 149 | 5-chloro-1H-benzimidazole | H | 446.4 | |
| 150 | 6-chloro-1H-benzimidazole | H | 446.4 | |
| 151 | 1:1 mixture of 5-chloro-2-methyl-1H-benzimidazole and 6-chloro-2-methyl-1H-benzimidazole | CH$_3$ | 474.4 | |

TABLE IX-continued

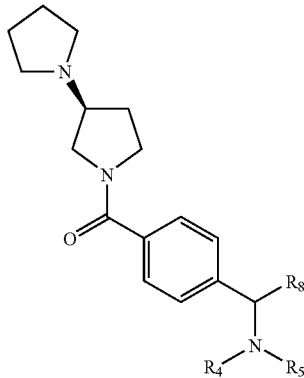

| Ex. No. | NR4R5 | R8 | [M + H] | Time (Min.) |
|---|---|---|---|---|
| 152 | 5-chloro-2-methyl-1H-benzimidazole | (S)-CH$_3$ | 474.4 | |
| 153 | 5-chloro-2-methyl-1H-benzimidazole | (R)-CH$_3$ | 474.4 | |
| 154 | 6-chloro-2-methyl-1H-benzimidazole | (S)-CH$_3$ | 474.4 | |
| 155 | 6-chloro-2-methyl-1H-benzimidazole | (R)-CH$_3$ | 474.4 | |
| 156 | 7-chloro-1H-indole | CH$_3$ | 459.4 | |
| 157 | 5-chloro-1H-indole | CH$_3$ | 459.4 | |
| 158 | 5-cyano-1H-indole | CH$_3$ | 450.0 | |

EXAMPLES 159-163

Preparation of (3S)-1-[4-(Heteroarylalkyl)benzoyl]-pyrrolidin-3-amine

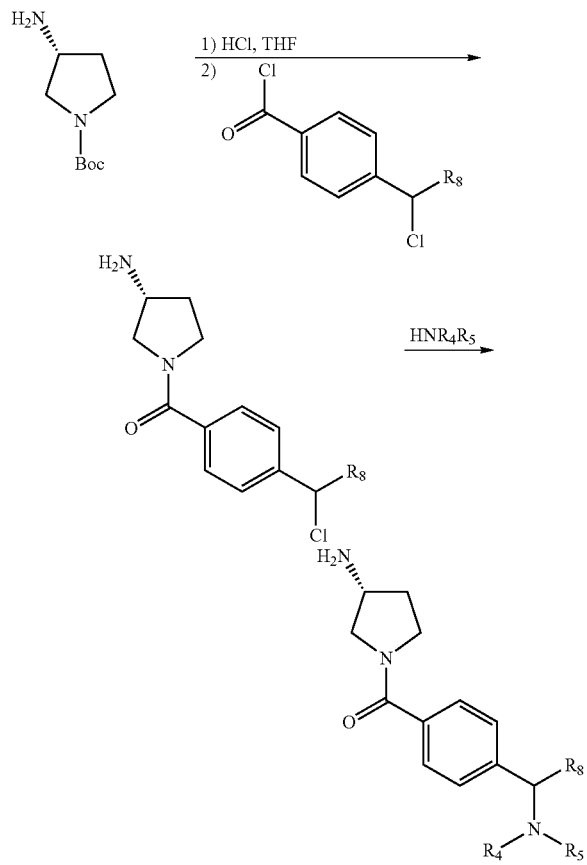

Using essentially the same procedure described in Example 127 and employing (S)-3-aminopyrrolidine as starting material and the appropriately substituted 4-chloromethylbenzoyl chloride in Step 3 and the desired bicyclic amine, HNR$_4$R$_5$, in Step 4, the compounds shown in Table X are obtained and identified by mass spec and $^1$H NMR analyses. Those compounds on Table X wherein R$_8$ is an (R) or (S) enantiomer were obtained by chiral separation of the corresponding racemic compound using standard chiral HPLC techniques.

TABLE X

| Ex. No. | NR4R5 | R8 | [M + H] |
|---|---|---|---|
| 159 | 5-chloro-2-methyl-1H-benzimidazole | (S)-CH$_3$ | 420.4 |
| 160 | 5-chloro-2-methyl-1H-benzimidazole | (R)-CH$_3$ | 420.4 |
| 161 | 6-chloro-2-methyl-1H-benzimidazole | (S)-CH$_3$ | 420.4 |
| 162 | 6-chloro-2-methyl-1H-benzimidazole | (R)-CH$_3$ | 420.4 |
| 163 | 5-chloro-1H-benzimidazole | CH$_3$ | 392.3 |

EXAMPLE 164

Preparation of 1'-[4-(1H-Benzimidazol-1-ylmethyl)benzyl]-1,3'-bipyrrolidine Hydrochloride

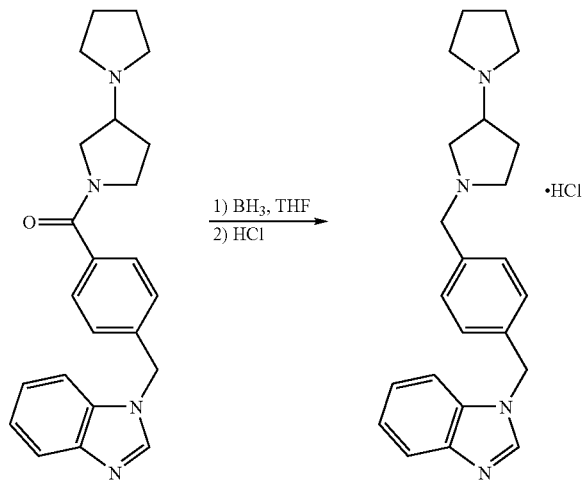

A solution of 1'-[4-(1H-benzimidazol-1-ylmethyl)benzoyl]-1,3'-bipyrrolidine (0.16 mmol) in anhydrous tetrahydrofuran, under nitrogen, is treated with borane (1.0 M in tetrahydrofuran, 0.8 mL), heated at reflux temperature for 1.5 h, treated with additional borane (1.0 M in tetrahydrofuran, 0.8 mL, 0.8 mmol), heated at reflux temperature for 6 h, cooled to room temperature, treated with methanol (5 mL) and concentrated in vacuo. The resultant residue is treated with methanolic hydrogen chloride (5 mL), heated at reflux temperature for 1 h and concentrated in vacuo. This residue is dispersed in aqueous sodium hydroxide (2.5 M, 5 mL) and extracted with dichloromethane. The extracts are combined, dried (sodium sulfate) and evaporated. Purification of the resultant residue by flash column chromatography (silica, dichloromethane:methanol 9:1) followed by formation of the hydrochloride salt affords the title product as a fluffy solid, identified by NMR and mass spectral analyses, [M+H] 361.2.

EXAMPLES 165-172

Preparation of 1-[4-(Heteroarylmethyl)benzyl]pyrrolidin-3-ylamine Hydrochloride Compounds

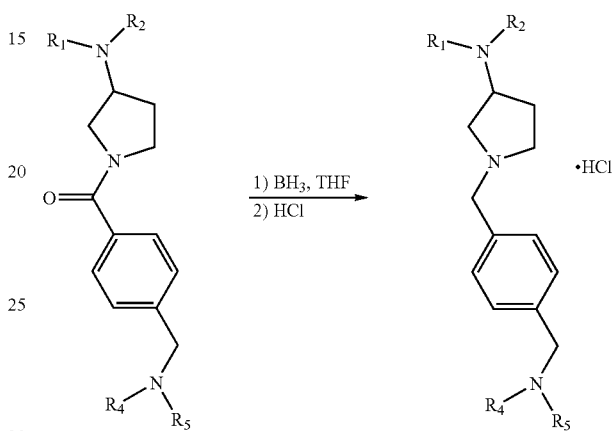

Using essentially the same procedure described in Example 164 and employing the appropriate 1-[4-(heteroarylmethyl)benzoyl]pyrrolidin-3-ylamine starting material, the compounds shown in Table XI are obtained and identified by mass spec and either $^1$H NMR or HPLC analyses.

TABLE XI

| Ex. No. | NR1R2 | NR4R5 | [M + H] | Time (Min.) |
|---|---|---|---|---|
| 165 | pyrrolidine | 6-methyl-1H-benzimidazole | 375.3 | 5.06 |
| 166 | pyrrolidine | 5-fluoro-1H-benzimidazole | 379.4 | 5.42 |
| 167 | piperidine | 5-fluoro-1H-benzimidazole | 393.4 | 5.69 |
| 168 | (S)-pyrrolidine | 1H-benzimidazole | 361.2 | — |
| 169 | (S)-pyrrolidine | 2-methyl-1H-benzimidazole | 375.2 | — |
| 170 | pyrrolidine | 4-fluoro-1H-benzimidazole | 379.3 | 5.85 |
| 171 | N-methylethylamine | 4-fluoro-1H-benzimidazole | 367.4 | 5.71 |
| 172 | (S)-pyrrolidine | 6-fluoro-1H-benzimidazole | 379.3 | 5.89 |

EXAMPLES 173-179

Preparation of 1-[3-(Heteroarylmethyl)benzyl]pyrrolidin-3-ylamine Hydrochloride Compounds

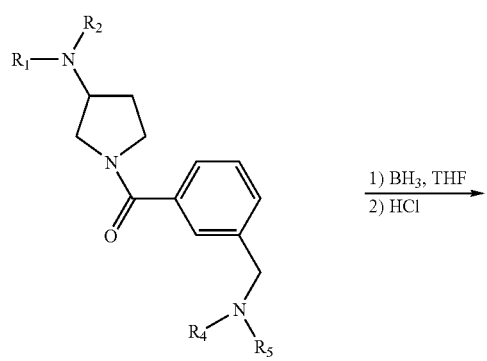

1) BH₃, THF
2) HCl

-continued

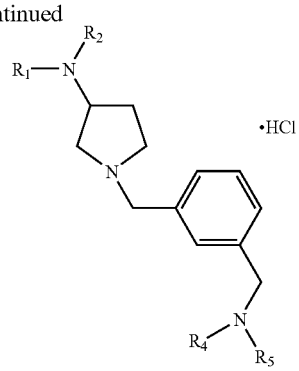

Using essentially the same procedure described in Example 164 and employing the appropriate 1-[3-(heteroarylmethyl)benzoyl]pyrrolidin-3-ylamine starting material, the compounds shown in Table XII are obtained and identified by ¹H NMR, HPLC and mass spectral analyses.

TABLE XII

| Ex. No. | NR1R2 | NR4R5 | [M + H] | Time (Min.) |
|---|---|---|---|---|
| 173 | pyrrolidine | 1H-benzimidazole | 361.3 | 4.9 |
| 174 | methylethylamine | 1H-benzimidazole | 349.3 | 4.64 |
| 175 | dimethylamine | 1H-benzimidazole | 335.3 | 4.39 |
| 176 | piperidine | 1H-benzimidazole | 375.3 | 4.86 |
| 177 | dimethylamine | 4-fluoro-1H-benzimidazole | 353.5 | — |
| 178 | (3'S)-pyrrolidine | 4-fluoro-1H-benzimidazole | 379.3 | — |
| 179 | (2R)-2-methylpyrrolodine | 5-fluoro-1H-benzimidazole | 393.3 | — |

EXAMPLE 180

Preparation of 1-[2-(1H-Benzimidazol-1-ylmethyl)benzyl]pyrrolidin-3-ylpiperidine Hydrochloride

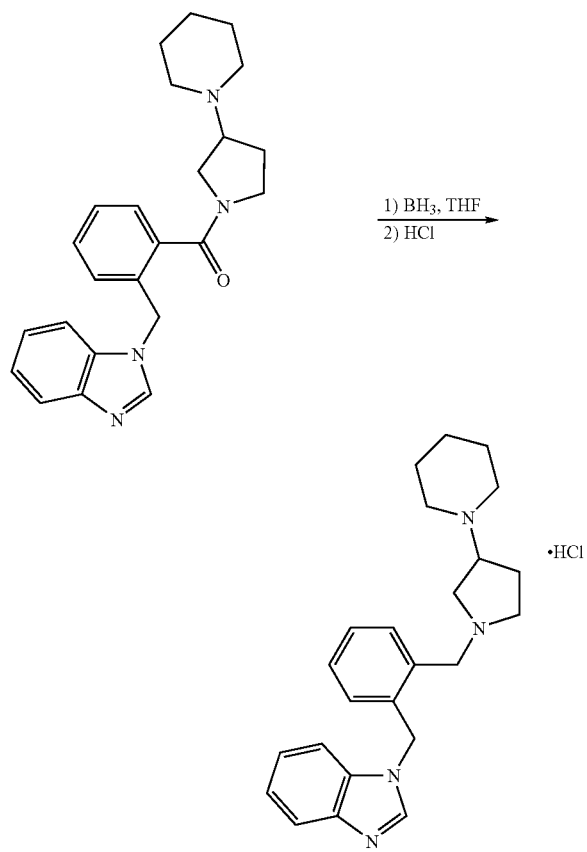

Using essentially the same procedure described in Example 113 and employing 1-[2-(1H-benzimidazol-1-ylmethyl)benzoyl]pyrrolidin-3-ylpiperidine as starting material, the title compound is obtained and identified by ¹H NMR, HPLC and mass spectral analyses, [M+H] 375.3.

EXAMPLES 181-201

Preparation of Substituted-1-[2-(1H-benzimidazol-1-yl)methyl)benzoyl]-pyrrolidin-3-ylamine Compounds

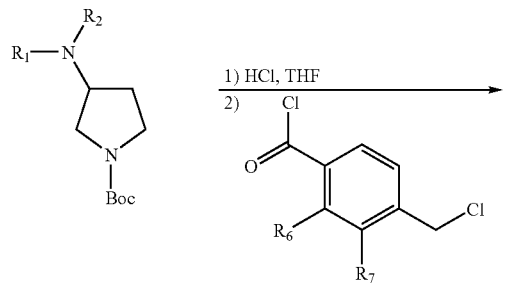

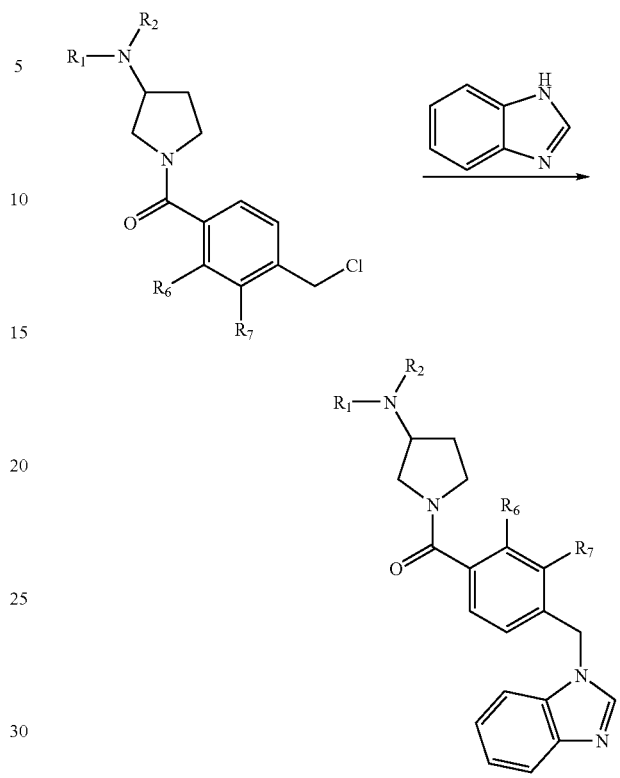

Using essentially the same procedure described in Example 127 and employing the appropriate Boc-protected pyrrolidine and desired 4-chloromethyl-benzoyl chloride in Step 3, the compounds shown on Table XIII are obtained and identified by ¹H NMR, HPLC and mass spectral analyses.

TABLE XIII

| Ex. No. | NR1R2 | R6 | R7 | [M + H] | Time (Min.) |
|---|---|---|---|---|---|
| 181 | pyrrolidine | H | OCH₃ | 405.3 | 4.72 |
| 182 | piperidine | H | OCH₃ | 419.3 | 4.92 |
| 183 | dimethylamine | H | OCH₃ | 379.3 | 4.46 |
| 184 | pyrrolidine | H | F | 393.4 | 4.69 |

TABLE XIII-continued

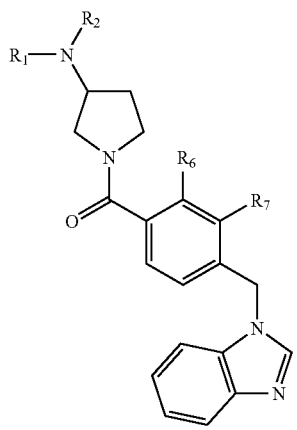

| Ex. No. | NR1R2 | R6 | R7 | [M + H] | Time (Min.) |
|---|---|---|---|---|---|
| 185 | methylethylamine | H | OCH₃ | 393.3 | 4.88 |
| 186 | dimethylamine | H | Cl | 383.3 | 4.94 |
| 187 | pyrrolidine | H | Cl | 409.3 | 5.02 |
| 188 | piperidine | H | Cl | 423.3 | 5.74 |
| 189 | pyrrolidine | OCH₃ | H | 405.3 | 5.26 |
| 190 | piperidine | OCH₃ | H | 419.4 | 5.39 |
| 191 | (2R)-2-methylpyrrolidine | H | F | 407.3 | 5.72 |
| 192 | piperidine | H | F | 393.4 | 5.87 |
| 193 | methylethylamine | H | F | 381.3 | 5.23 |
| 194 | dimethylamine | H | F | 367.3 | 5.03 |
| 195 | methylethylamine | H | Cl | 397.2 | 5.40 |
| 196 | pyrrolidine | H | F | 379.3 | 5.87 |
| 197 | methylethylamine | OCH₃ | H | 393.3 | 5.07 |
| 198 | dimethylamine | OCH₃ | H | 379.3 | — |
| 199 | (2R)-2-methylpyrrolidine | OCH₃ | H | 419.3 | — |
| 200 | pyrrolidine | F | H | 392.2 | — |
| 201 | piperidine | H | F | 407.4 | 4.88 |

EXAMPLES 202-205

Preparation of 1-[4-(1H-Benzimidazol-1-ylmethyl)benzyl]pyrrolidin-3-ylamine Hydrochloride Compounds

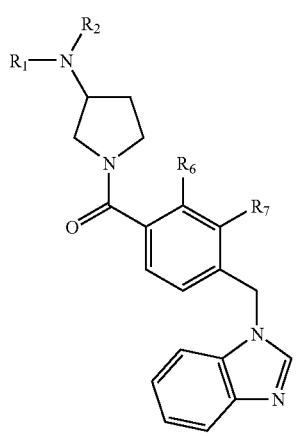 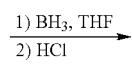

1) BH₃, THF
2) HCl

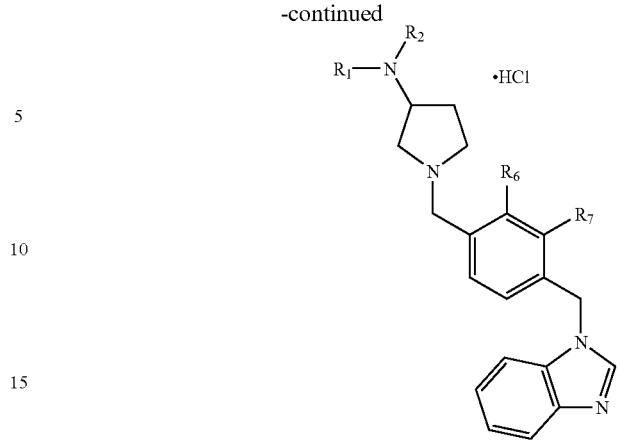

Using essentially the same procedure described in Example 164 and employing the appropriately substituted 1-[4-(1H-benzimidazol-1-ylmethyl)benzoyl]-pyrrolidin-3-ylamine as starting material, the compounds shown on Table XIV were obtained and identified by ¹H NMR and mass spectral analyses.

TABLE XIV

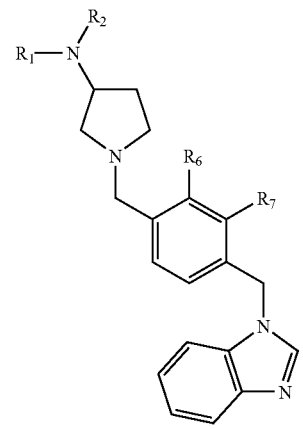

| Ex. No. | NR1R2 | R6 | R7 | [M + H] |
|---|---|---|---|---|
| 202 | pyrrolidine | H | Cl | 395.3 |
| 203 | piperidine | H | Cl | 409.3 |
| 204 | ethylmethylamine | H | Cl | 383.3 |
| 205 | dimethylamine | H | Cl | 369.3 |

EXAMPLES 206 AND 207

Preparation of N-Substituted-1-[(heteroarylmethyl)benzoyl]pyrrolidin-3-ylamine Compounds

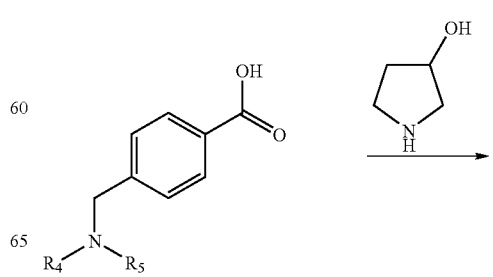

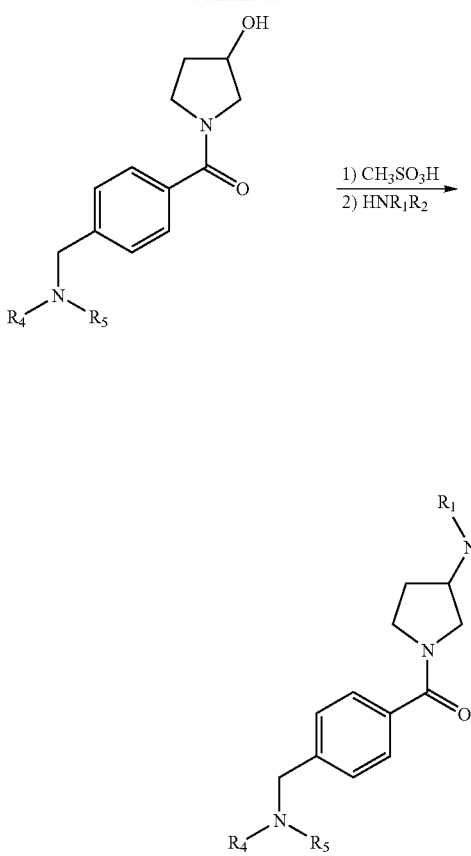

Using essentially the same procedure described in Example 40 and employing the desired benzoic acid in Step 1 and the appropriate amine, HNR$_1$R$_2$, in step 3, the compounds shown in Table XV are obtained and identified by $^1$H NMR and mass spectral analyses.

TABLE XV

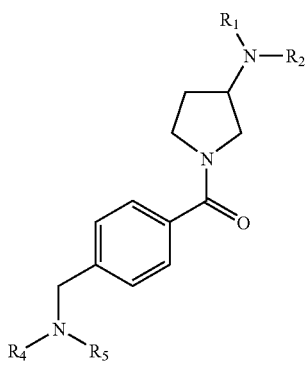

| Ex. No. | NR1R2 | NR4R5 | [M + H] |
|---|---|---|---|
| 206 | pyrrolidine | 5-chloro-2-methyl-1H-benzo[d]imidazole | 424.9 |
| 207 | pyrrolidine | 6-chloro-2-methyl-1H-benzo[d]imidazole | 424.9 |

EXAMPLE 208

Preparation of Methyl 4-((1H-Benzo[d]imidazol-2-yl)methyl)benzoate

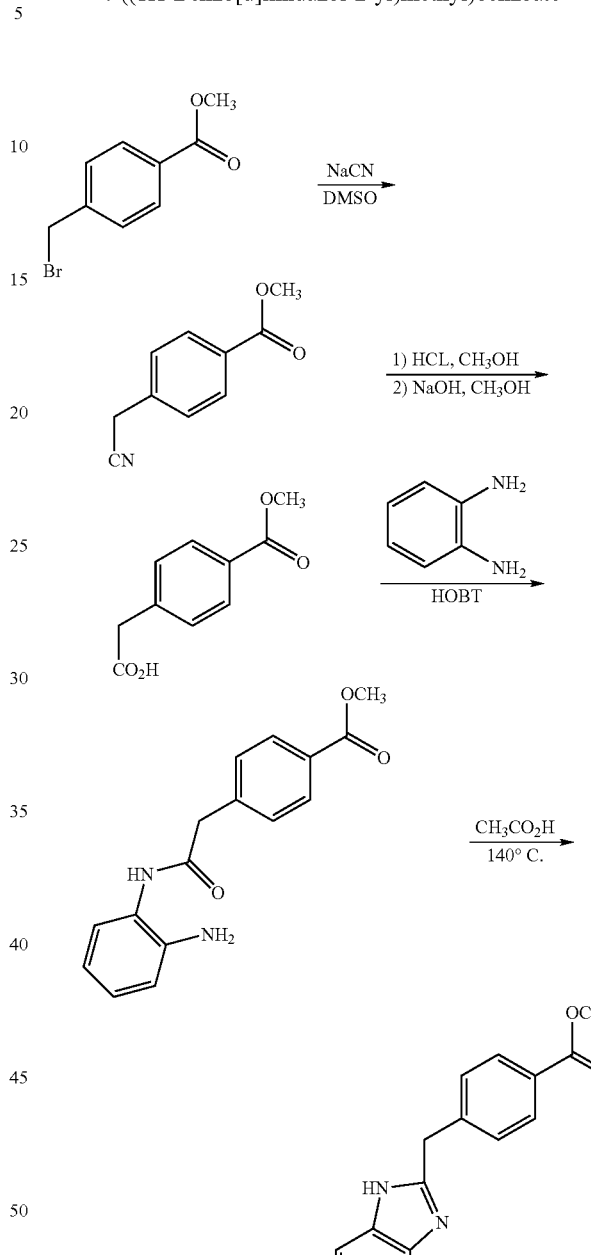

Step 1: Methyl 4-(Cyanomethyl)benzoate

A solution of sodium cyanide (20 g, 0.41 mol) in dimethylsulfoxide at 40° C. was treated dropwise with a solution of methyl 4-(bromomethyl)benzoate (52 g, 0.227 mol) in dimethylsulfoxide, stirred for 90 min., cooled to room temperature, quenched with saturated aqueous sodium chloride and extracted with ethyl acetate. The combined extracts were washed with saturated aqueous sodium chloride, dried over sodium sulfate and concentrated under reduced pressure.

Purification of the concentrate via column chromatography (silica, hexane:ethyl acetate 0→5%) provided methyl 4-(cyanomethyl)benzoate (55%). $^1$H NMR (400 MHz, CDCl$_3$): 8.05 (d, J=8 Hz, 2H); 7.42 (d, J=8 Hz, 2H); 3.93 (s, 3H); 3.81 (s, 2H). [M+H] 176

Step 2: 2-(4-(Methoxycarbonyl)phenyl)acetic Acid

A stirred solution of methyl 4-(cyanomethyl)benzoate (22.0 g, 0.125 mol) in methanol (550 mL) was bubbled through with hydrogen chloride gas for 8 h under reflux conditions. The reaction mixture was cooled to 20° C., stirred for an additional 24 h and filtered. The filtrate was evaporated under reduced pressure. The resultant residue was dissolved in diethyl ether, washed sequentially with water and saturated aqueous sodium hydrogen carbonate, dried over sodium sulfate and evaporated to afford the methyl ester as a solid residue. $^1$H NMR (400 MHz, CDCl$_3$): 8.00 (d, J=8 Hz, 2H); 7.35 (d, J=8.4 Hz, 2H); 3.91 (s 3H); 3.70 (s, 3H); 3.68 (s, 2H). GCMS: 209 (M+H). The methyl ester (8.21 g, 0.039 mmol) was dissolved in methanol, treated with sodium hydroxide (1.58 g, 0.039 mol), heated to 50° C., stirred for 4 h, cooled to room temperature, stirred for an additional 24 h and concentrated in vacuo. The resultant residue was partitioned between diethyl ether and water. The aqueous layer was acidified with concentrated HCl. The resultant precipitate was removed by filtration and dried overnight, under vacuum, to afford 2-(4-(methoxycarbonyl)phenyl)-acetic acid (80%) as an off-white solid. $^1$H NMR (400 MHz, DSMO-d$_6$): 7.90 (d, J=8 Hz, 2H); 7.422 (d, J=8 Hz, 2H); 3.85 (s 3H) 3.68 (s, 2H). [M+H] 195

Steps 3 and 4: Methyl 4-((1H-Benzo[d]imidazol-2-yl)methyl)benzoate

A suspension of 2-(4-(methoxycarbonyl)phenyl)acetic acid (0.2 g, 1.03 mmol) in dichloromethane at 0° C. was treated with 1-(3-dimethylaminopropyl)-3-ethylcarbodiimide hydrochloride (0.236 g, 1.237 mmol) and 1-hydroxybenzotriazole (HOBT) (0.153 g, 1.13 mmol), stirred for 30 min, treated with phenylenediamine (0.12 g, 1.12 mmol), stirred at room temperature for 24 h and quenched with water. The organic phase was separated, washed sequentially with saturated aqueous sodium hydrogen carbonate and saturated aqueous sodium chloride, dried over sodium sulfate and concentrated to dryness under reduced pressure to obtain the desired amide (68%) as an off-white solid. [M+H] 285. A solution of the amide (12.0 g, 0.04 mol) in acetic acid was heated to 140° C. for 1 h, cooled to room temperature and concentrated under reduced pressure. The resultant residue was neutralized with aqueous sodium hydroxide (1.0 N, 100 mL) and extracted with ethyl acetate. The extracts were combined, dried over sodium sulfate and concentrated under reduced pressure. Purification of the concentrate by column chromatography (silica,chloroform:methanol 0→5%) afforded the title product (47%) as a white solid. $^1$H NMR (400 MHz, DMSO-d$_6$): 7.95 (d, J=8 Hz, 2H); 7.52 (s, 2H); 7.325 (d, J=8 Hz, 2H); 7.23 (m, 2H); 4.30 (s, 2H); 3.89 (s, 3H). [M+H] 267

EXAMPLE 209

Preparation of 1-(4-((1H-Benzo[d]imidazol-2-yl)methyl)benzoyl)pyrrolidin-3-yl Methanesulfonate

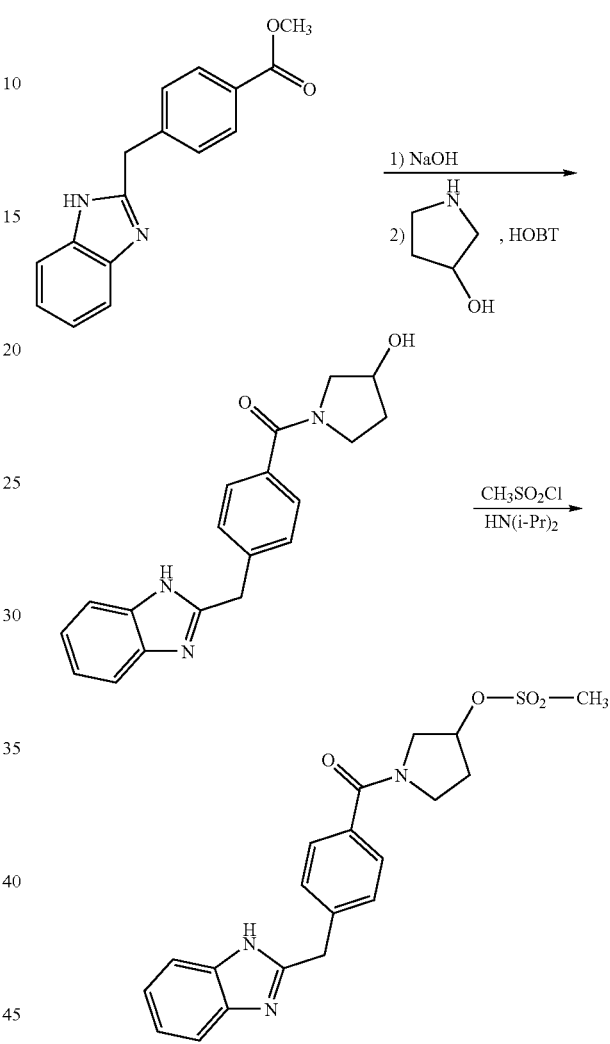

Step 1: [4-(1H-Benzoimidazol-2-ylmethyl)-phenyl]-(3-hydroxy-pyrrolidin-1-yl)-methanone A solution of methyl 4-((1H-benzo[d]imidazol-2-yl)methyl)benzoate (5 g, 0.019 mol) in methanol was treated with sodium hydroxide (1.50 g, 0.037 mol) and water, heated to 65° C., stirred for 3 h and concentrated under reduced pressure. The resultant residue was dissolved in water and acidified with concentrated HCl. The resultant precipitate was removed by filtration and dried under vacuum overnight to provide 4-((1H-benzo[d]imidazol-2-yl)methyl)benzoic acid (82.0%). $^1$H NMR-(400 MHz, DSMO-d$_6$): 7.96 (d, J=8 Hz, 2H), 7.91 (m, J=9 Hz, 2H), 7.60 (d, J=8 Hz, 2H), 7.52 (m, J=6 Hz, 2H), 4.65 (s, 2H). LCMS (ESI$^+$) 253 (M+H). A portion of 4-((1H-benzo[d]imidazol-2-yl)methyl)benzoic acid (5.0 g, 0.020 mol) was dissolved in dichloromethane, cooled to 0° C., treated with 1-(3-dimethylaminopropyl)-3-ethylcarbodiimide hydrochloride (4.50 g, 0.023 mol), 1-hydroxybenzotriazole (HOBT) (3.21 g, 0.024 mol), and diisopropylethylamine (6.41 g, 0.049 mol), stirred at room temperature for 30 min, cooled to 0° C., treated with a solution of 3-pyrrolidinol (1.89 g, 0.021 mol) in dichloromethane, stirred at room temperature for 24 h and diluted with water. The phases were separated and the organic phase was washed sequentially with saturated aqueous NaHCO₃, saturated aqueous NaCl, dried over sodium sulfate and concentrated to dryness under reduced pressure to provide [4-(1H-benzoimidazol-2-ylmethyl)-phenyl]-(3-hydroxy-pyrrolidin-1-yl)-methanone (34%) as a yellow solid. $^1$H NMR (400 MHz, DMSO-d₆): 7.47 (s, 4H), 7.38 (d, J=7.6 Hz, 2H), 4.87 (s, J=4.2 Hz, 1H), 4.21 (d, 2H), 3.48 (m, 4 H), 1.85 (m, 2H). LCMS (ESI⁺) 322 (M+H).

Step 2: 1-(4-((1H-Benzo[d]imidazol-2-yl)methyl) benzoyl)pyrrolidin-3-yl Methanesulfonate A portion of [4-(1H-benzoimidazol-2-ylmethyl)-phenyl]-(3-hydroxy-pyrrolidin-1-yl)-methanone (1.00 g, 3.1 mmol) was dissolved in dichloromethane, treated with diisopropylethylamine (0.60 g, 4.6 mmol), cooled to 0° C., treated dropwise with a solution of methanesulfonyl chloride (0.49 g, 4.3 mmol) in dichloromethane, stirred at 0° C. for 10 min. and concentrated under vacuum to provide a solid residue. Purification of this residue by column chromatography (silica, chloroform:methanol 0→5%) gave the title product as a yellow solid (62%). $^1$H NMR (400 MHz, CDCl₃): 7.58 (m, 2H), 7.56 (m, 4H), 7.22 (m, 2H), 5.27 (d, J=5.4 Hz 1H), 4.35 (s, 2H), 3.93 (s, 1H), 3.80 (s, 1H), 3.63 (m, 4H), 3.09 (m, 3H), 2.31 (m, 2H). [M+H] 400.

EXAMPLE 210

Preparation of Methyl 4-((1-Methyl-1H-benzo[d]imidazol-2-yl)methyl)benzoate

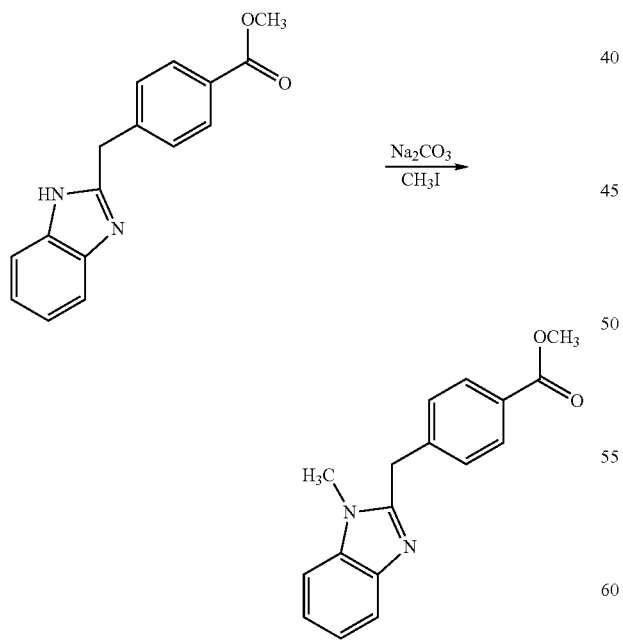

A solution of methyl 4-((1H-benzo[d]imidazol-2-yl)methyl)benzoate (0.2 g, 0.75 mmol) in acetone was treated with potassium carbonate (0.31 g, 2.2 mmol), cooled to 0° C., treated dropwise with and methyl iodide (0.070 mL, 1.1 mmol), heated at 40° C. for 12 h, cooled to room temperature, and filtered. The filtrate was evaporated under reduced pressure. Purification of the resultant residue by column chromatography (silica, chloroform) afforded the title product (28%). $^1$H NMR (400 MHz, CDCl₃): 7.98 (d, J=8.4 Hz, 2H), 7.7 (m, 1H), 7.37 (m,5H), 4.38 (s, 2H), 3.9 (s, 3H), 3.5 (s, 3H). [M+H] 281.

EXAMPLE 211

Preparation of 1-(4-((1-Methyl-1H-benzo[d]imidazol-2-yl)methyl)benzoyl)pyrrolidin-3-yl Methanesulfonate

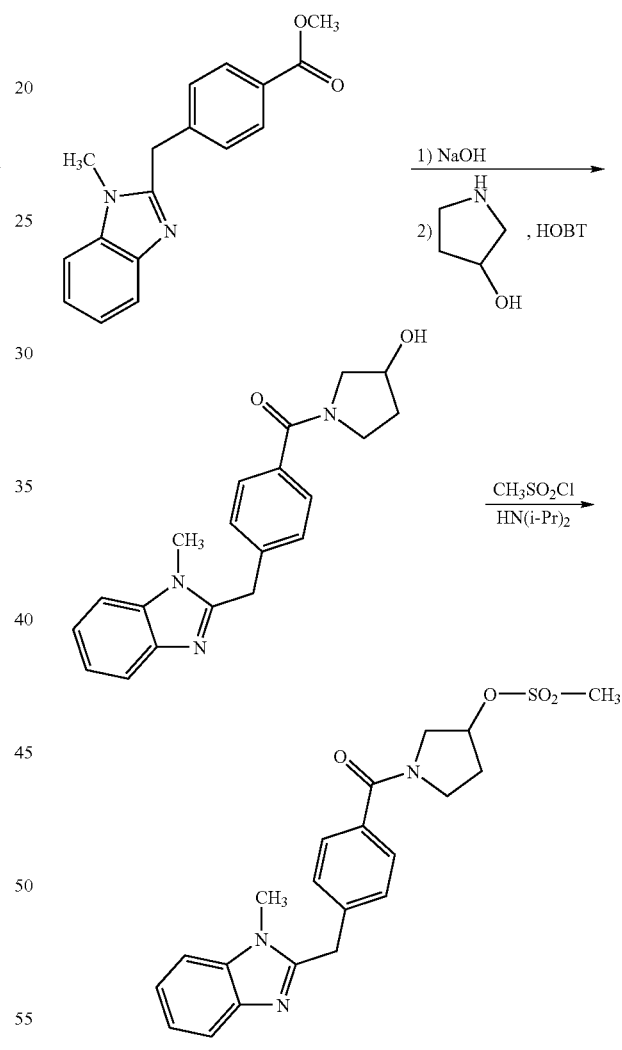

Using essentially the same procedure described in Example 209 and employing methyl 4-((1-methyl-1H-benzo[d]imidazol-2-yl)methyl)benzoate in step 1, the title product was obtained as a yellow solid, $^1$H NMR (400 MHz, CDCl₃) 7.77 (m, 1H), 7.44-7.50 (m, 2H), 7.21-7.30 (m, 5H), 5.23 & 5.37 (bs, 1H), 4.37 (s, 2H), 3.93 (s, 1H), 3.75-3.82 (bs, 1H) 3.70-3.80 (m, 2H), 3.58-3.65 (m, 1H), 3.61 (s, 3H), 3.08 & 2.98 (s, 3H), 2.33-2.35 (m, 1H). [M+H] 414.

EXAMPLE 212
Preparation of 1,3'-Bipyrrolidin-1'-yl{4-[(1H-benzo[d]imidazol-2-yl)methyl]-phenyl}methanone Fumarate

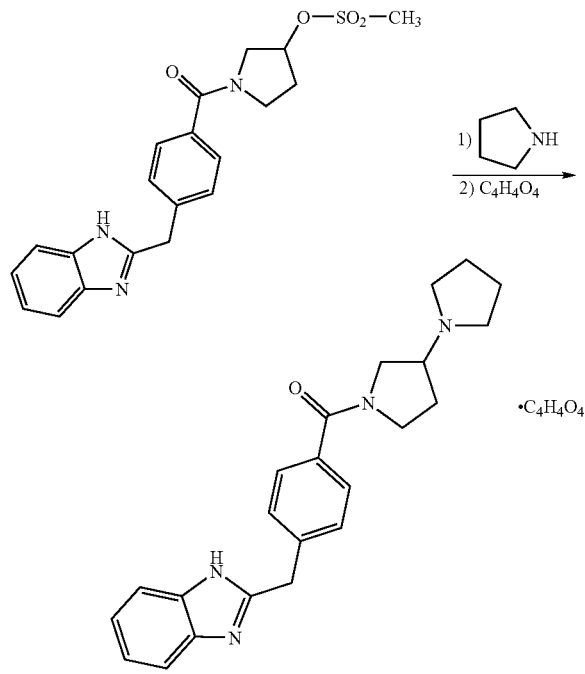

A mixture of 1-(4-((1H-benzo[d]imidazol-2-yl)methyl)benzoyl)pyrrolidin-3-yl methanesulfonate (0.8 g, 2.0 mmol) and pyrrolidine (1.14 g, 16 mmol) was placed in a sealed tube and heated to 110° C. for 3 h. The tube was cooled, carefully opened and the excess pyrrolidine was evaporated under reduced pressure. The resultant residue was purified by column chromatography (neutral alumina, chloroform:methanol 0→5%). The purified material was treated with fumaric acid in methanol/dichloromethane to give the title product as a white solid. $^1$H NMR (300 MHz, DMSO-$d_6$): 7.48 (m, 2H); 7.45 (d, 2H); 7.39 (d, 2H); 7.12 (m, 2H); 6.64 (s, 2H); 4.23 (s, 2H); 3.75-3.22 (m, 6H); 2.89 (m, 1H); 2.59-2.49 (m, 2H); 2.08-1.79 (m, 2H); 1.70 (m, 4H). [M+H] 375.2.

EXAMPLES 213-215
Preparation of {4-[(1H-benzo[d]imidazol-2-yl)methyl]phenyl}[(3-azacyclyl)pyrrolidin-1-yl]methanone

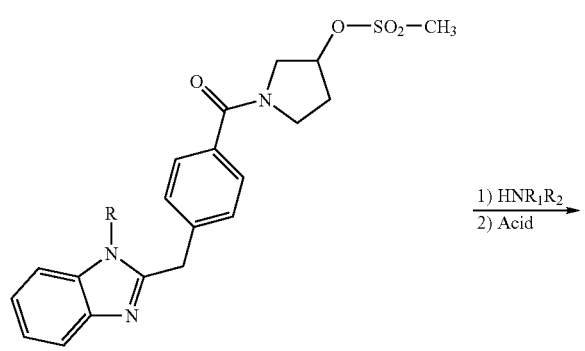

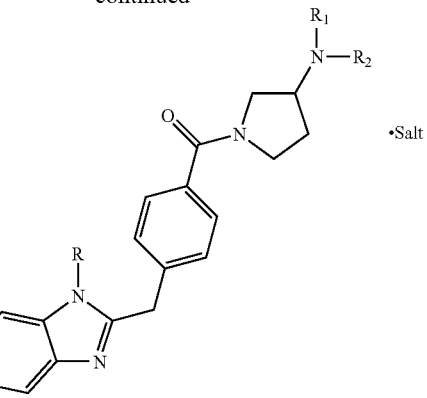

Using essentially the same procedure described in Example 212 and employing the appropriate 1-(4-((1H-benzo[d]imidazol-2-yl)methyl)benzoyl)pyrrolidin-3-yl methanesulfonate and desired amine, the compounds shown on Table XVI were obtained and identified by $^1$H NMR and mass spectral analyses.

TABLE XVI

| Ex. No. | R | NR1R2 | Salt | [M + H] |
|---|---|---|---|---|
| 213 | H | piperidin-1-yl | HCl | 389.3 |
| 214 | CH$_3$ | pyrrolidin-1-yl | C$_4$H$_4$O$_4$ | 389.2 |
| 215 | CH$_3$ | piperidin-1-yl | C$_4$H$_4$O$_4$ | 403.2 |

EXAMPLE 216
Preparation of (1,3'-Bipyrrolidin-1'-yl{4-[(1-ethyl-1H-benzo[d]imidazol-2-yl)methyl]phenyl}methanone Hydrochloride

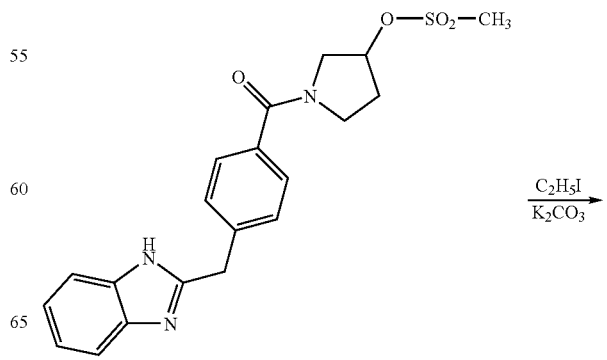

-continued

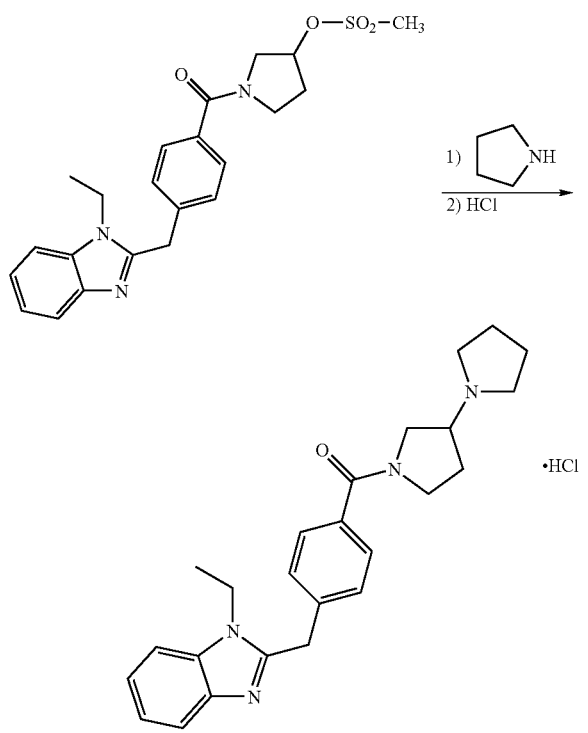

Step 1: 1-{4-[(1-Ethyl-1H-benzo[d]imidazol-2-yl)methyl]benzoyl}pyrrolidin-3-yl Methanesulfonate A stirred solution of 1-{4-[(1H-benzo[d]imidazol-2-yl)methyl]benzoyl}-pyrrolidin-3-yl methanesulfonate (0.250 g, 0.6 mmol) in DMF was treated with potassium carbonate (0.260 g, 1.9 mmol), cooled to −5° C., treated dropwise with ethyl iodide (0.24 g, 1.5 mmol) at 0° C. over 20 min, warmed to room temperature, heated at 50° C. for 3 h, cooled to room temperature and filtered. The filtrate was concentrated in vacuo. The resultant residue was dissolved in ethyl acetate, washed with water, dried over sodium sulfate and concentrated in vacuo. Purification of this residue by column chromatography (neutral alumina, chloroform:methanol 100:0→98:2) afforded 1-{4-[(1-ethyl-1H-benzo[d]imidazol-2-yl)methyl]benzoyl}pyrrolidin-3-yl methanesulfonate (19%). $^1$H NMR (400 MHz, CDCl$_3$): 7.79-7.77 (m, 1H), 7.44-7.51 (m, 3H), 7.32-7.25 (m, 4H), 5.37 & 5.23 (bs, 1H), 4.36 (s, 2H), 4.05-4.10 (q, J=8 Hz, 2H), 3.93 (bs, 1H), 3.82 (m, 1H), 3.57-3.71 (bs, 2H), 3.08 & 3.00 (s, 3H), 2.33-2.36 (m, 1H), 2.17-2.21 (m, 1H), 1.18-1.22 (t, J=8 Hz, 3H). [M+H] 428.

Step 2: {1,3'-Bipyrrolidin-1'-yl{4-[(1-ethyl-1H-benzo[d]imidazol-2-yl)methyl]phenyl}}methanone Hydrochloride A mixture of 1-{4-[(1-ethyl-1H-benzo[d]imidazol-2-yl)methyl]benzoyl}pyrrolidin-3-yl methanesulfonate (0.06 g, 0.14 mmol) and pyrrolidine (0.08 g, 1.12 mmol) was placed in a microwave test tube and heated with microwave irradiation at 110° C. for 15 min. The excess pyrrolidine was evaporated under reduced pressure and the resultant residue was purified by column chromatography (neutral alumina, chloroform:methanol 100:0→95:5). The purified material was treated with ethereal HCl to give the title product. $^1$H NMR (300 MHz, DMSO-d$_6$): 7.83-7.73 (m, 2H); 7.56 (d, 2H); 7.48 (d, 2H); 7.48-7.43 (m, 2H); 4.63 (s, 2H); 4.44 (q, 2H); 4.03-3.25 (m, 7H); 3.07 (m, 2H); 2.30 (m, 2H); 2.14-1.84 (m, 4H); 1.27 (t, 3H). [M+H] 403.2.

EXAMPLES 217-222

Preparation of (3'S)-1'-{4-[(1-alkyl-1H-benzimidazol-2-yl)methyl]benzoyl}-1,3'-bipyrrolidine Fumarate

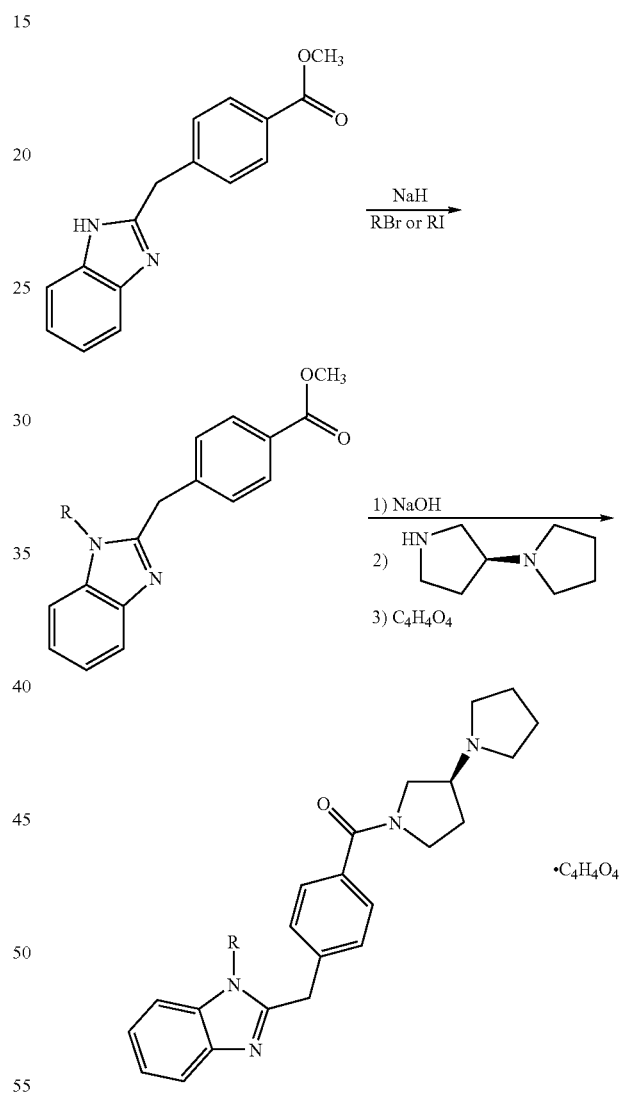

Step 1: Methyl 4-[(1-Alkyl-1H-benzo[d]imidazol-2-yl)methyl]benzoate

Sodium hydride (60% disp. in mineral oil, 48 mg, 1.24 mmol) was washed with petroleum ether, suspended in N,N-dimethylformamide, cooled to 0° C., treated with a solution of methyl 4-[(1H-benzo[d]imidazol-2-yl)methyl]benzoate (300 mg, 1.13 mmol) in DMF, stirred at 0° C. for 10 min, stirred at room temperature for 15 min, cooled to 0° C., treated dropwise with a solution of the selected alkyl bromide or iodide (1.24 mmol) in DMF over 10 min, stirred at room temperature for 5 h and concentrated under reduced pressure. The resultant residue was partitioned between water and dichloromethane. The organic phase was separated, dried over sodium sulfate and evaporated to dryness under reduced pressure. This residue was purified by flash column chromatography (silica, petroleum ether:ethyl acetate 8:2 to 1:1) to give methyl 4-[(1-alkyl-1H-benzo[d]imidazol-2-yl)methyl]benzoate.

Step 2: (3'S)-1'-{4-[(1-Alkyl-1H-benzimidazol-2-yl)methyl]benzoyl}-1,3'-bipyrrolidine Fumarate The benzoate (0.8 mmol) was dissolved in methanol, treated with aqueous sodium hydroxide (2.5 M, 2.0 mmol), heated at reflux temperature for 4 h and concentrated in vacuo. The residue was dispersed in water and acidified with excess formic acid. The resultant precipitate was removed by filtration, washed with water and dried under vacuum overnight to give the corresponding benzoic acid. The benzoic acid (0.381 mmol) was dissolved in DMF, treated with 1-(3-dimethyl-aminopropyl)-3-ethylcarbodiimide hydrochloride (87.7 mg, 0.457 mmol) and 1-hydroxybenzotriazole (56.6 mg, 0.419 mmol), stirred at room temperature for 30 min, treated with a solution of (3'S)-1,3'-bipyrrolidine (79.8 mg, 0.57 mmol) in DMF, stirred at room temperature for 6 h and concentrated in vacuo. This residue was partitioned between aqueous potassium carbonate (1.0 M) and dichloromethane. The organic was separated, washed with water, dried over sodium sulfate and concentrated under reduced pressure. Purification of this concentrate by flash column chromatography (silica, dichloromethane:methanol 20:1 to 10:1) followed by treatment with fumaric acid in dichloromethane/methanol afforded the compounds shown in Table XVII. The compounds shown in Table XVII were identified by $^1$H NMR and mass spectral analyses.

TABLE XVII

| Ex. No. | R | [M + H] |
|---|---|---|
| 217 | propyl | 417.4 |
| 218 | isopropyl | 417.3 |
| 219 | isobutyl | 431.2 |
| 220 | cyctopropylmethyl | 429.3 |
| 221 | 2-methoxyethyl | 433.17 |
| 222 | ethyl | 403.13 |

EXAMPLE 223

Preparation of 2-(2-{4-[(3'S)-1,3'-Bipyrrolidin-1'-ylcarbonyl]benzyl}-1H-benzimidazol-1-yl)ethanol Fumarate

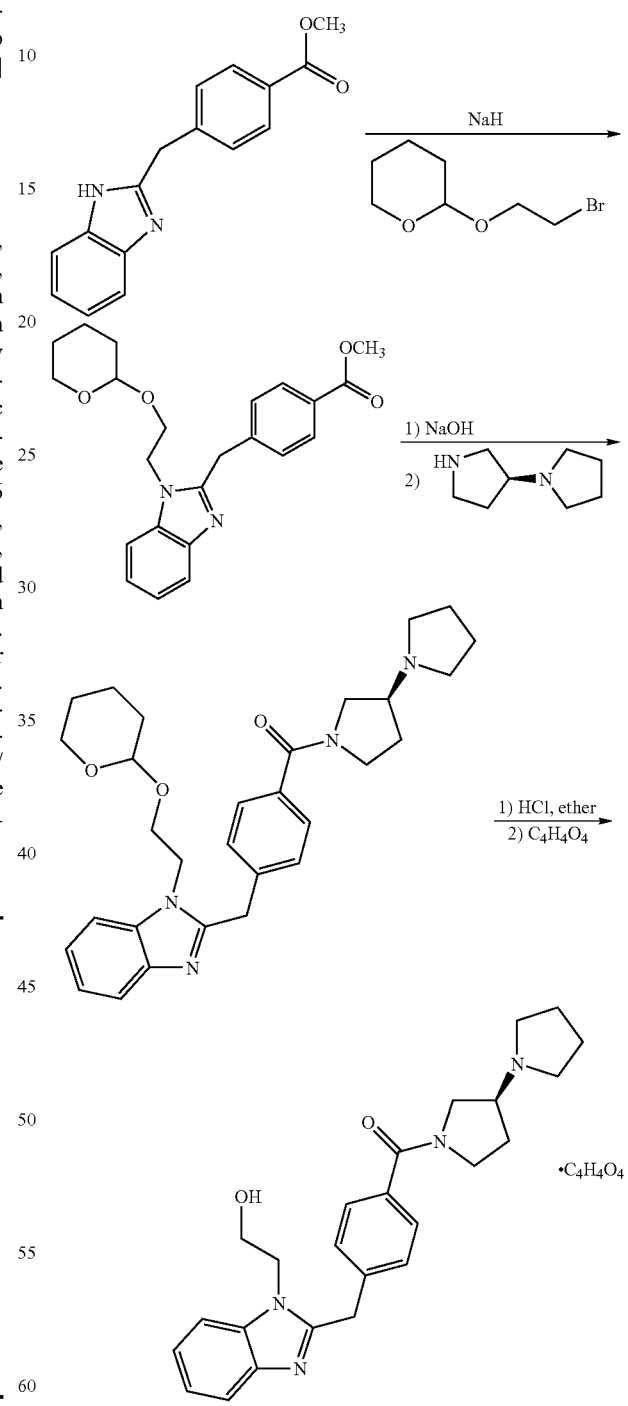

Using essentially the same procedure described for Examples 217-222 and employing methyl 4-((1H-benzo[d]imidazol-2-yl)methyl)benzoate and 2-(2-bromoethoxy)tetrahydro-2H-pyran as starting materials, (3'S)-1'-{4-[(1-(2-(tetrahydro-pyran-2-yloxy)-ethyl)-1H-benzimidazol-2-yl)

methyl]benzoyl}-1,3'-bipyrrolidine was obtained, [M+H] 503.2. A portion of (3'S)-1'-{4-[(1-(2-(tetrahydro-pyran-2-yloxy)-ethyl)-1H-benzimidazol-2-yl)methyl]benzoyl}-1,3'-bipyrrolidine was treated with hydrogen chloride in diethyl ether/ethanol, stirred at room temperature and concentrated in vacuo. The resultant residue was partitioned between aqueous potassium carbonate (1.0 M) and dichloromethane. The organic phase was separated, washed with water, dried over sodium sulfate and concentrated under reduced pressure. This residue was treated with fumaric acid in dichloromethane/methanol to give the title product. $^1$H NMR (300 MHz, DMSO-d$_6$+TFA): 7.94 (m, 1 H), 7.79 (m, 1 H), 7.57 (d, 2 H), 7.57 (m, 2 H), 7.49 (d, 2 H), 6.65 (s, 2 H), 4.74 (s, 2 H), 4.58 (t, 2 H), 3.92 (m, 2 H), 3.80 (t, 2 H), 3.74 (m, 2 H), 3.51 (m, 2 H), 3.44-3.06 (br. s, 3 H), 2.33 (m, 1 H), 2.21 (m, 1 H), 1.99 (m, 4 H). [M+H] 419.17.

EXAMPLE 224

Preparation of (3'S)-1'-{4-[(1-Phenethyl-1H-benzimidazol-2-yl)methyl]benzoyl}-1,3'-bipyrrolidine Fumarate

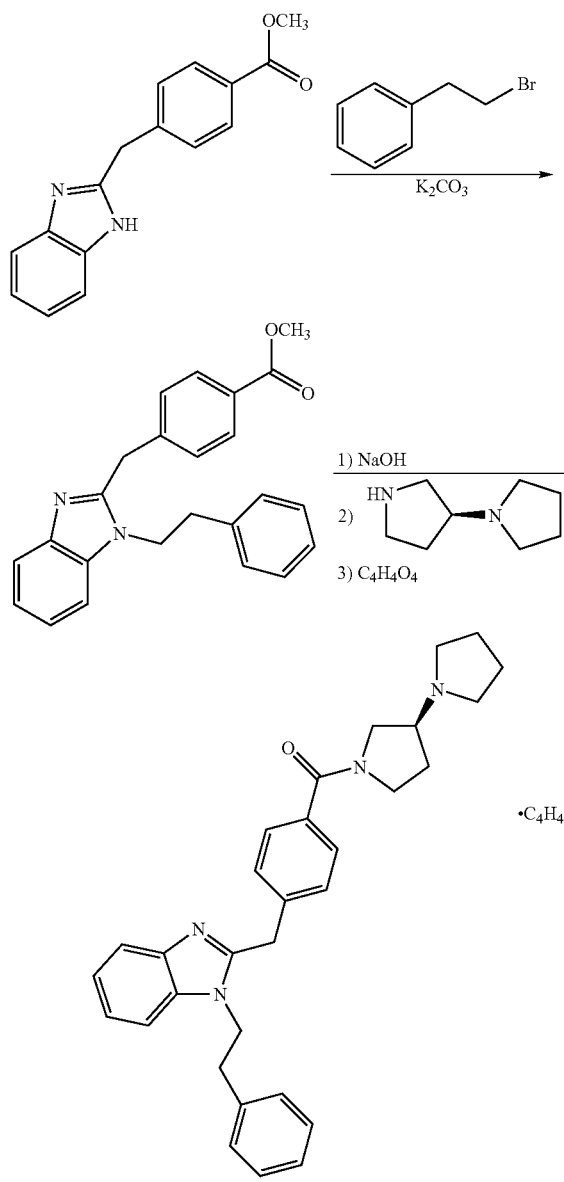

Step 1: Methyl 4-(1-Phenethyl-1H-benzoimidazol-2-ylmethyl)benzoate

A solution of methyl 4-((1H-benzo[d]imidazol-2-yl)methyl)benzoate (200 mg, 0.75 mmol) in acetonitrile was treated with (2-bromoethyl)benzene (209 mg, 1.13 mmol) and potassium carbonate (143 mg, 0.90 mmol). The reaction mixture was heated with microwave irradiation at 100° C. for 2 h. The solvent was removed under reduced pressure and the residue was partitioned between water and dichloromethane. The organic phase was separated, dried over sodium sulfate and concentrated in vacuo. Purification of the resultant residue by flash column chromatography (silica, petroleum ether:ethyl acetate 8:2 to 1:1) afforded 4-(1-phenethyl-1H-benzoimidazol-2-ylmethyl)-benzoic acid methyl ester (30%). [M+H] 371.2.

Step 2: (3'S)-1'-{4-[(1-Phenethyl-1H-benzimidazol-2-yl)methyl]benzoyl}-1,3'-bipyrrolidine Fumarate Using essentially the same procedure described in Examples 217-222, step 2, and employing methyl 4-(1-phenethyl-1H-benzoimidazol-2-ylmethyl)-benzoate as starting material, the title product was obtained. $^1$H NMR (300 MHz, DMSO-d$_6$): 7.54-7.61 (m, 1 H), 7.41-7.49 (m, 3 H), 7.16-7.32 (m, 7 H), 7.08 (dd, 2 H), 6.64 (s, 2 H), 4.34-4.43 (m, 2 H), 4.06-4.20 (m, 2 H), 3.38-3.62 (m, 5 H), 3.32 (dd, 1 H), 2.80-2.94 (m, 3 H), 2.42-2.58 (m, 2 H), 1.93-2.08 (m, 1 H), 1.76-1.90 (m, 1 H), 1.63-1.74 (m, 4 H), [M+H] 379.22.

EXAMPLE 225

Preparation of (3'S)-1'-[4-(1H-Benzimidazol-2-ylmethyl)benzoyl]-1,3'-bipyrrolidine

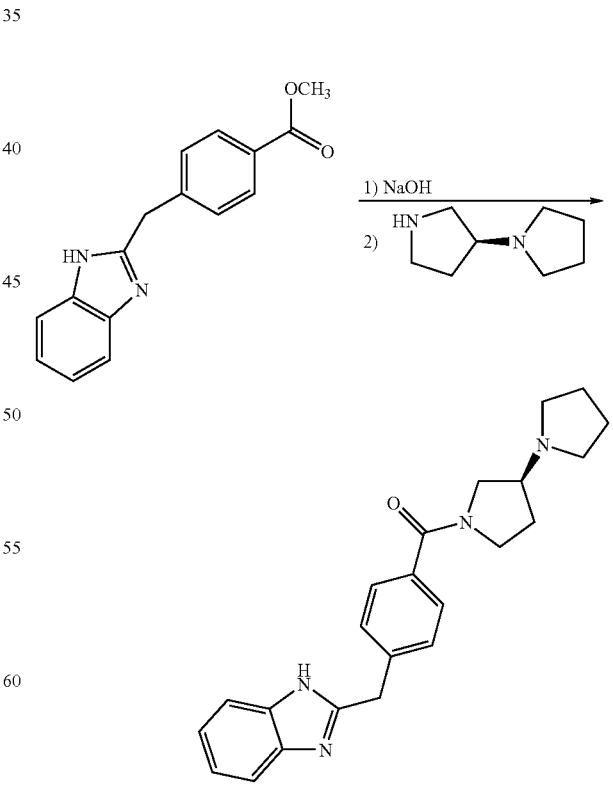

A solution of methyl 4-((1H-benzo[d]imidazol-2-yl)methyl)benzoate (400 mg, 1.5 mmol) in methanol was treated with aqueous sodium hydroxide (2.5 M, 3.75 mmol), heated at reflux temperature for 3 h and concentrated in vacuo. The resultant residue was dispersed in water and acidified with excess formic acid. The resultant precipitate was removed by filtration, washed with water and dried under vacuum overnight to provide 4-((1H-benzo[d]imidazol-2-yl)methyl)benzoic acid (92%) as a white solid, [M+H] 253.2. A solution of 4-((1H-benzo[d]imidazol-2-yl)methyl)benzoic acid (200 mg, 0.79 mmol) in DMF was treated with 1-(3-dimethylaminopropyl)-3-ethylcarbodiimide hydrochloride (183 mg, 0.952 mmol) and 1-hydroxybenzotriazole (134 mg, 0.873 mmol), stirred at room temperature for 3 h, treated with a solution of (3'S)-1,3'-bipyrrolidine (166.6 mg, 1.19 mmol) in DMF, stirred at room temperature for 6 h and concenrated in vacuo. This residue was partitioned between aqueous potassium carbonate (1.0 M) and dichloromethane. The organic phase was washed with water, dried over sodium sulfate and concentrated under reduced pressure. Purification of the concentrate by flash column chromatography (silica, dichloromethane:methanol 20:1 to 10:1) afforded the title compound (73%), identified by mass spectral analysis. [M+H] 253.2.

EXAMPLE 226

Preparation of (3'S)-1'-{4-[(1-Phenyl-1H-benzimidazol-2-yl)methyl]benzoyl}-1,3'-bipyrrolidine Fumarate

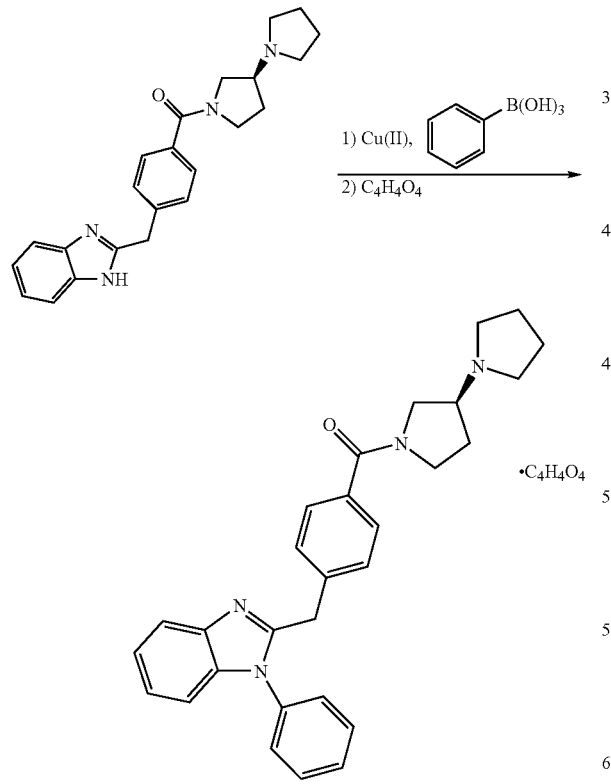

EXAMPLE 227

Preparation of (3'S)-1'-(4-{[1-(Phenylsulfonyl)-1H-benzimidazol-2-yl]methyl}-benzoyl)-1,3'-bipyrrolidine Fumarate

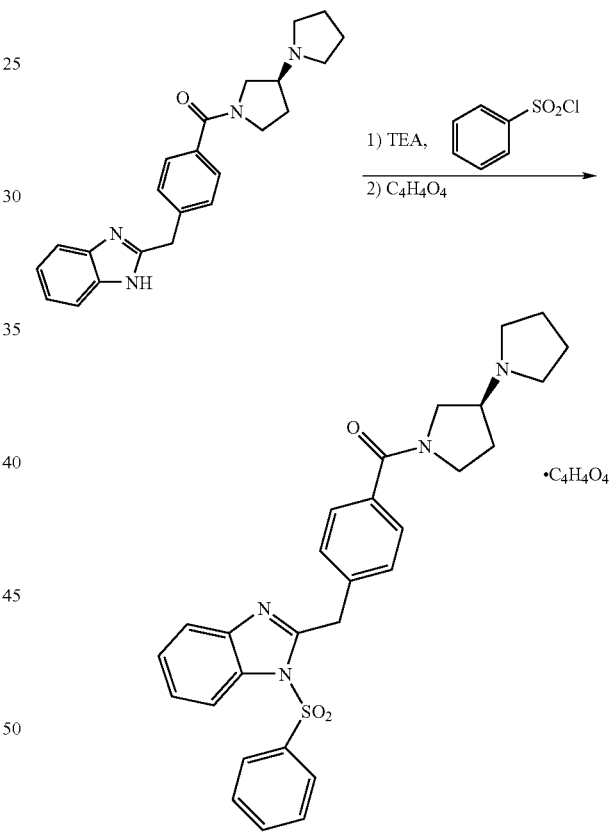

A solution of (3'S)-1'-[4-(1H-benzimidazol-2-ylmethyl)benzoyl]-1,3'-bipyrrolidine (78 mg, 0.21 mmol) in dichloromethane was treated with pyridine (34 µL, 0.42 mmol) followed by phenylboronic acid (50.7 mg, 0.42 mmol), copper (II) acetate (56 mg, 0.31 mmol) and 4 Å molecular sieves, stirred at room temperature for 24 h and filtered. The filtrate was evaporated under reduced pressure and the resultant residue was partitioned between aqueous potassium carbonate (1.0 M) and dichloromethane. The organic phase was separated, washed with water, dried over sodium sulfate and concentrated under reduced pressure. The resultant residue was purified by flash column chromatography (silica, dichloromethane:methanol 98:2 to 90:10). The purified material was treated with fumaric acid in dichloromethane/methanol to give the title product, $^1$H NMR (300 MHz, DMSO-$d_6$): 7.65-7.73 (m, 1 H), 7.49-7.62 (m, 3 H), 7.39-7.48 (m, 2 H), 7.35 (d, 2 H), 7.16-7.29 (m, 2 H), 7.05-7.15 (m, 3 H), 6.61 (s, 2 H), 4.22 (s, 2 H), 3.00-3.78 (m, 7 H), 2.54-2.66 (m, 2 H), 1.97-2.11 (m, 1 H), 1.63-1.89 (m, 5 H). [M+H] 451.33

A solution of (3'S)-1'-[4-(1H-benzimidazol-2-ylmethyl)benzoyl]-1,3'-bipyrrolidine (100 mg, 0.267 mmol) in anhydrous dichloromethane was cooled to 0° C. under an inert atmosphere, treated with triethylamine (TEA) (32 mg, 0.32 mmol) followed by dropwise addition of a solution of benzenesulfonyl chloride (51.7 mg, 0.293 mmol) in anhydrous dichloromethane, stirred at 0° C. for 1 h, warmed to room temperature for 1 h and concentrated under reduced pressure. The resultant residue was partitioned between dichloromethane and 5% aqueous NaHCO$_3$. The organic phase was separated, washed with water, dried over sodium sulfate and concentrated under reduced pressure to give a residue. This residue was treated with fumaric acid in dichloromethane/methanol to afford the title compound, $^1$H NMR (300 MHz, DMSO-d$_6$, +TFA): 7.96 (d, 1 H), 7.90 (d, 2 H), 7.78-7.66 (m, 2 H), 7.59 (m, 2 H), 7.49 (d, 2 H), 7.45-7.29 (m, 4 H), 6.63 (s, 2 H), 4.67 (s, 2 H), 3.58-3.41 (m, 4 H), 3.10-2.76 (m, 5 H), 2.19 (m, 1 H), 2.00 (m, 1 H), 1.91-1.73 (m, 4 H). [M+H] 515.1

EXAMPLE 228

Preparation of (3'S)-1'-[4-(1H-indol-1-ylmethyl)benzoyl]-1,3'-bipyrrolidine

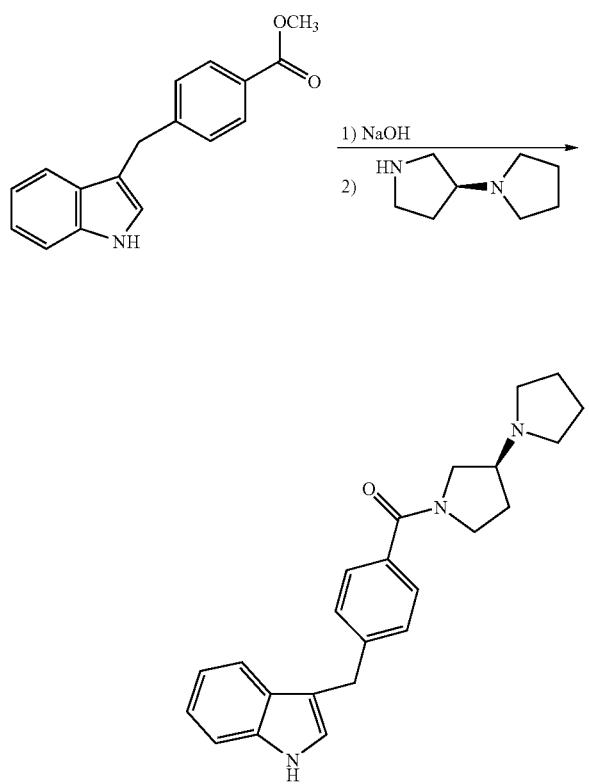

A solution of methyl 4-((1H-indol-3-yl)methyl)benzoate (Tet. Lett. 44 (2003) 4589-4591) (0.50 g, 1.88-mmol) in methanol is treated with an aqueous solution of NaOH (4.15 mL, 1N, 4.15 mmol), heated to reflux temperature for 3 h and concentrated in vacuo. The resultant solid residue is dissolved in H$_2$O and acidified with HCl. The resultant precipitate is removed by filtration and dried to yield 4-((1H-indol-3-yl)methyl)benzoic acid as a white solid, 0.468 g (99%). A microwave vial is charged with PS-Carbodiimide (0.275 g, 1.2 mmol/g, 0.33 mmol). To the vial is added a solution of 4-((1H-indol-3-yl)methyl)-benzoic acid (0.070 g, 0.28 mmol) in CH$_3$CN, a solution of HOBT (0.045 g, 0.33 mmol) in CH$_3$CN, a solution of (S)-1,3'-bipyrrolidine (0.065 g, 0.31 mmol) in CH$_3$CN and 0.11 mL of triethylamine. The reaction mixture is irradiated in the Emry's Optimizer at 110° C. for 6 minutes and then concentrated under reduced pressure. The resultant residue is purified by flash chromatography to yield the title product as a white solid, 0.064 g, (68%), mp 141-153° C., identified by H$^1$ NMR and mass spectral analyses. MS (ES) m/z 372.2.

EXAMPLE 229

Preparation of (3'S)-1-{4-[(1-methyl-1H-indol-3-yl)methyl]benzoyl}-1,3'-bipyrrolidine

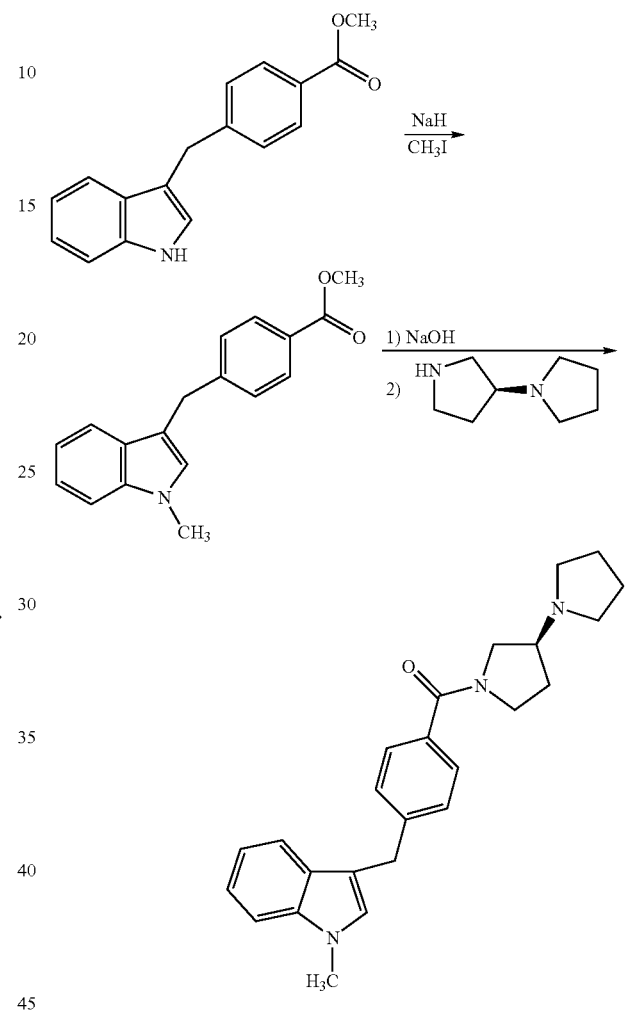

Step 1: Methyl 4-((1-Methyl-1H-indol-3-yl)methyl)benzoate

A solution of methyl 4-((1H-indol-3-yl)methyl)benzoate (0.250 g, 0.94 mmol) in THF is added dropwise to a suspension of NaH (0.048 g, 1.19 mmol) in THF. The mixture is stirred for 15 minutes, treated with methyl iodide (0.154 g, 1.08 mmol), stirred for 30 minutes and concentrated in vacuo. The resultant solid residue is partioned between CH$_2$Cl$_2$ and H$_2$O. The organic phase is separated, dried over Na$_2$SO$_4$ and concentrated to dryness to yield methyl 4-((1-methyl-1H-indol-3-yl)methyl)benzoate.

Step 2: (3'S)-1'-{4-[(1-methyl-1H-indol-3-yl)methyl]benzoyl}-1,3'-bipyrrolidine

Using essentially the same procedure described in Example 167 and employing methyl 4-((1-methyl-1H-indol-3-yl)methyl)benzoate as starting material, the title product is obtained as a white solid, mp 73-78° C., identified by H[1] NMR and mass spectral analyses. MS (ES) m/z 388.2; MS (ES) m/z 410.2.

EXAMPLE 230

Preparation of (3S)-N,N-dimethyl-1-{4-[(1-methyl-1H-indol-3-yl)methyl]benzoyl}pyrrolidin-3-amine

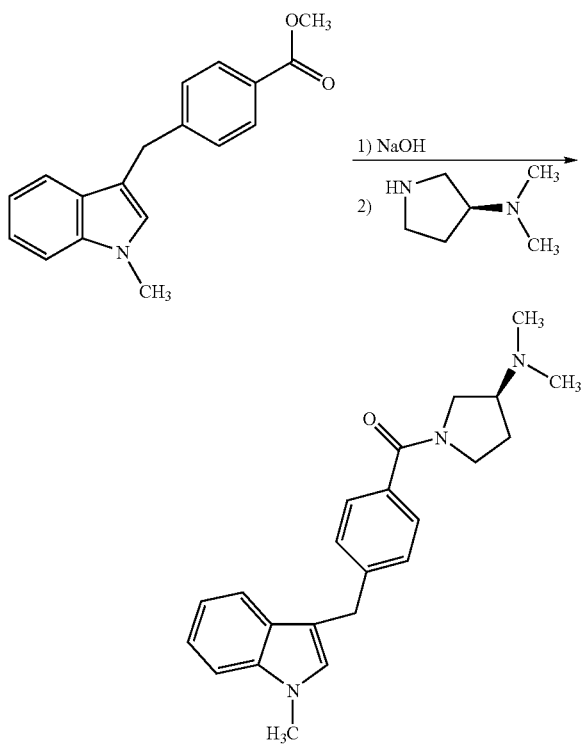

Using essentially the same procedure described in Example 228 and employing methyl 4-((1-methyl-1H-indol-3-yl)methyl)benzoate and (S)—N,N-dimethylpyrrolidin-3-amine as starting materials, the title compound is obtained as a white solid, mp 101-105° C., identified by H[1] NMR and mass spectral analyses. MS (ES) m/z 362.2; MS (ES) m/z 723.4.

EXAMPLE 231

Preparation of (3'S)-1'-(4-benzylbenzoyl)-1,3'-bipyrrolidine Hydrochloride

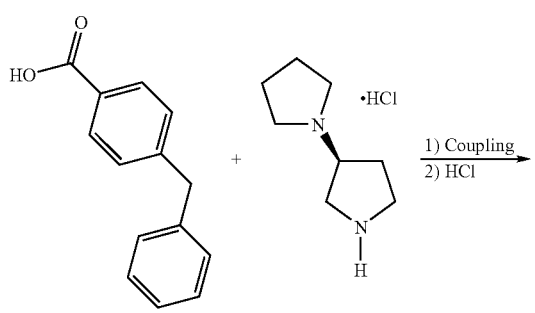

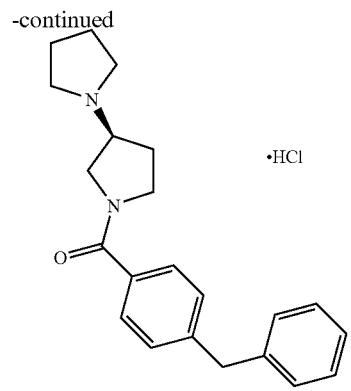

A mixture of the HCl salt of 3-(pyrrolidino)pyrrolidine (0.44 g, 2.1 mmol) and 4-benzyl benzoic acid (0.34 g, 1.6 mmol) $CH_2Cl_2$ is treated sequentially at room temperature with 0.85 mL of triethylamine and solid benzotriazol-1-yl-oxytripyrrolidinophosphonium hexafluorophosphate (1.2 g, 2.4 mmol), stirred for 16 h under nitrogen, diluted with $CH_2Cl_2$, washed sequentially with water and brine, dried over $MgSO_4$ and concentrated in vacuo. The concentrate is chromatographically purified. The purified material is treated with ethereal HCl to afford the title compound, identified by H[1] NMR and mass spectral analyses.

EXAMPLE 232

Preparation of (3'S)-1'-{4-[(1-Ethyl-1H-benzimidazol-2-yl)methyl]benzyl}-1,3'-bipyrrolidine

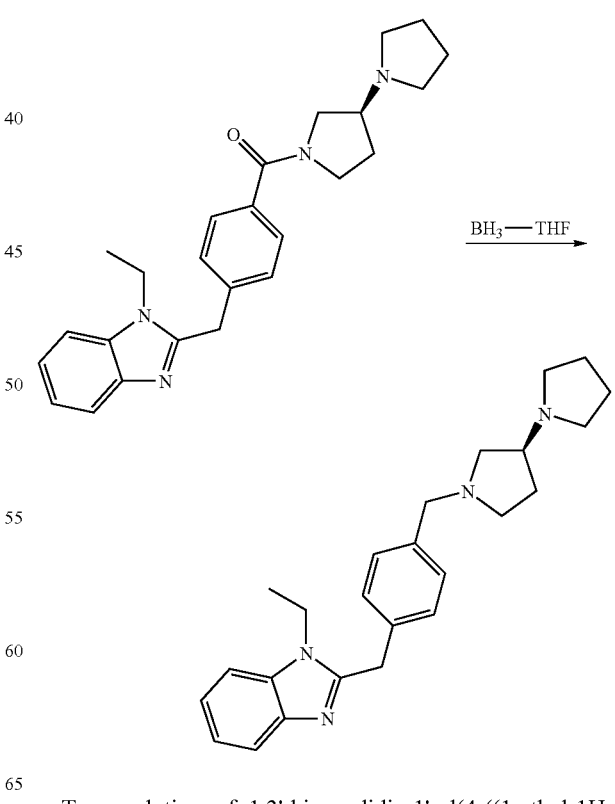

To a solution of 1,3'-bipyrrolidin-1'-yl(4-((1-ethyl-1H-benzo[d]imidazol-2-yl)methyl)phenyl)methanone (69 mg, 0.172 mmol, 1 eq) in anhydrous tetrahydrofuran (3 mL) was added borane-tetrahydrofuran complex (860 μL, 0.860 mmol, 1 M in tetrahydrofuran) and the reaction mixture has heated to reflux and allowed to stir for 3 h. The reaction mixture was cooled to room temperature, quenched by dropwise addition of methanol, and the solvent was evaporated under reduced pressure. The residue was treated with hydrogen chloride in methanol (5 mL) and heated at reflux for 1 h. The solvent was evaporated under reduced pressure and the residue was partitioned between dichloromethane and 1.0 N aqueous sodium hydroxide. The organic layer was separated and dried (sodium sulfate) and the solvent removed in vacuo. The residue was purified by flash column chromatography to afford the title product (65%). $^1$H NMR (300 MHz, DMSO-$d_6$): 7.74-7.86 (m, 2 H), 7.43-7.56 (m, 6 H), 6.64 (s, 2 H), 4.62 (s, 2 H), 4.46 (q, 2 H), 4.22 (s, 2 H), 4.00-4.10 (m, 1 H), 3.44-3.55 (m, 1 H), 3.24-3.40 (m, 6 H), 3.09-3.18 (m, 1 H), 2.35-2.45 (m, 1 H), 2.12-2.24 (m, 1 H), 1.91-2.02 (m, 4 H), 1.27 (t, 3 H). 389.22 (M+H).

EXAMPLE 233

Preparation of (2R,3'R)-1'-[4-(1H-Benzimidazol-1-ylmethyl)benzoyl]-2-methyl-1,3'-bipyrrolidine Hydrochloride Using essentially the same procedure described in Example 40 and employing 4-(1H-benzimidazol-1-ylmethyl)benzoic acid in Step 1 and (2R)-2-methylpyrrolidine in step 3, the title product was obtained as a yellow solid and identified by mass spec and $^1$H NMR analyses. MS [389.2 m/e (M+H]

EXAMPLE 234

Preparation of (2S,3'R)-1'-[4-(1H-Benzimidazol-1-ylmethyl)benzoyl]-2-methyl-1,3'-bipyrrolidine Hydrochloride

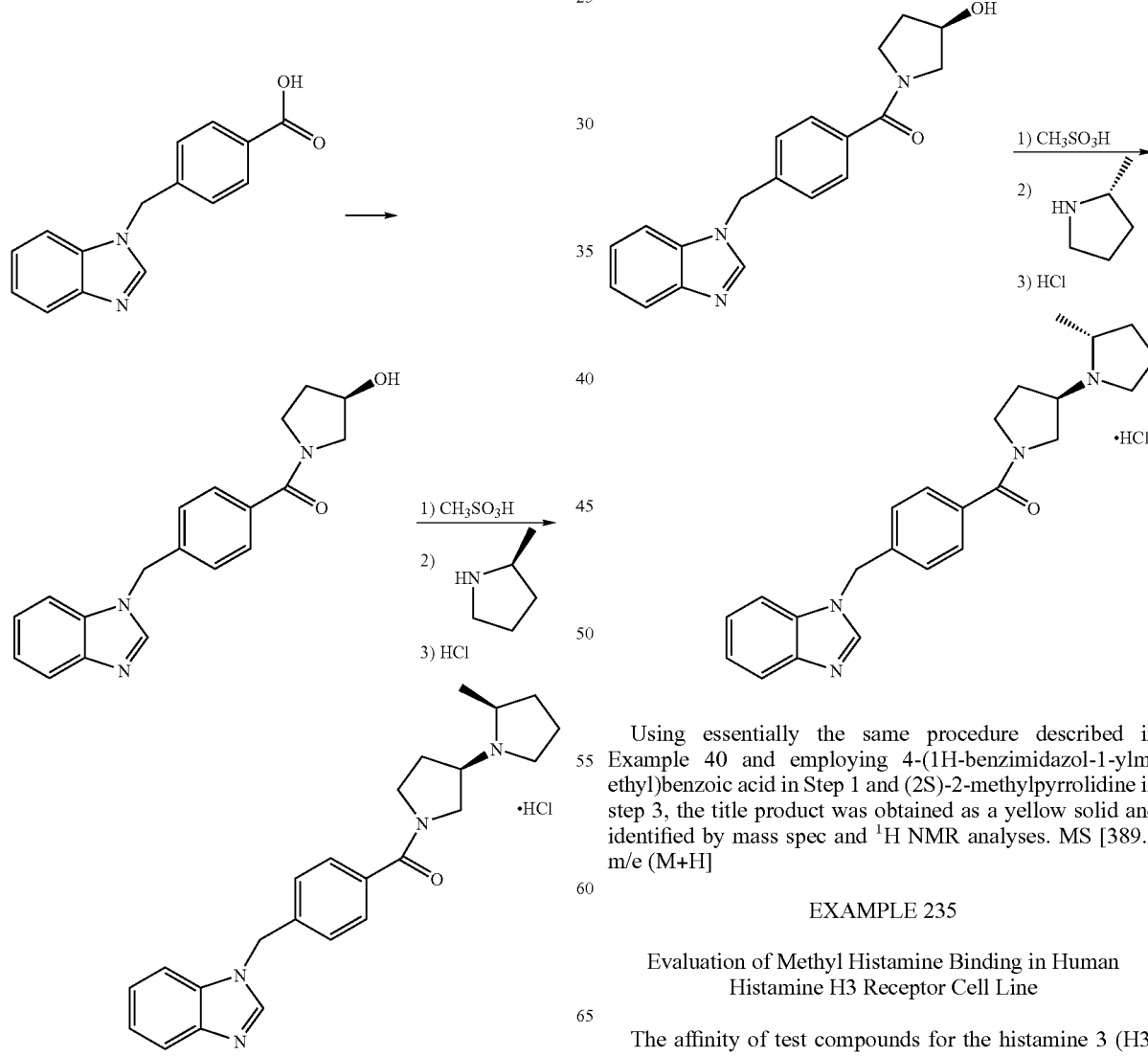

Using essentially the same procedure described in Example 40 and employing 4-(1H-benzimidazol-1-ylmethyl)benzoic acid in Step 1 and (2S)-2-methylpyrrolidine in step 3, the title product was obtained as a yellow solid and identified by mass spec and $^1$H NMR analyses. MS [389.2 m/e (M+H]

EXAMPLE 235

Evaluation of Methyl Histamine Binding in Human Histamine H3 Receptor Cell Line

The affinity of test compounds for the histamine 3 (H3) receptor is evaluated in the following manner. Stably transfected HEK293T cells are grown in DMEM containing 10% heat inactivated FBS and G-418 (500 ug/ml). Cells are scraped from the plate, transferred to centrifuge tubes, washed one time in PBS by centrifugation in a Sorvall RT7 Plus centrifuge (2000 rpm 10 minutes, 4° C.). The resulting pellets are stored at −80° C. until ready for use. Cells are re-suspended in buffer (50 mM Tris pH=7.5) and placed in a Dounce homogenizer, douncing ten times to homogenize cells. The homogenate is spun down by centrifugation (Sorvall RT7 Plus, 1800 rpm 10 minutes, 4° C.). The supernatant is placed in a Corex tube and spun down by centrifugation (Sorvall RC 5c Plus, 17,000 rpm 20 minutes, 4° C.). The pellet is resuspended in buffer (50 mM Tris, pH 7.5). Protein concentration (ug/ul) is determined using the Micro-BCA Protein Determination. The binding assay is set up in a 96 well microtiter plate in a total volume of 250 uL. Non-specific binding is determined in the presence of 10 uM clobenpropit. The final radioligand concentration is 1 nM. The test compound is serially diluted using the Beckman Biomek2000 to a final approximate range of 100 uM to 100 pM. Membranes are suspended in buffer, homogenized in 2 bursts of ten seconds using a Vitris mechanical homogenizer set at power setting 5. Ten μg of membranes are added to each well. Following a one hour incubation at 30° C., the reaction is terminated by the addition of ice cold buffer and rapid filtration with a Packard Filtermate Harvester through a GF/B filter pre-soaked with 1% PEI for one hour. The plate is dried for one hour at 37° C. and 60 μL Microscint Scintillant is added to each well. The CPM per well is measured on a Packard Top Count NXT. Ki values are determined in nM. The Ki is calculated from the $IC_{50}$ (i.e. the concentration of competing ligand which displaces 50% of the specific binding of the radioligand). CPM values are expressed as % specific binding and plotted vs compound concentration. A curve is fitted using a four-parameter logistic fit and the $IC_{50}$ value is determined. The Ki is calculated from this using the Cheng-Prusoff equation: $pKi=IC_{50}/1+(L/Kd)$ where L=concentration of free radioligand used in the assay, and Kd is the dissociation constant of the radioligand for the receptor. L is determined for each experiment by counting an aliquot of the diluted radioligand (corresponding to that added to each well) and the Kd has previously been determined under identical conditions for this cell line/radioligand.

Cyclic AMP Assay for Histamine Receptor H3 Antagonism Activity.

Stable H3 cells are maintained in tissue culture flask in DMEM with high glucose, 10% FBS, 1×pen/strep, 500 ug/ml GY18, until experiment. Culture media is removed and cells are washed twice with PBS w/ Ca++ and Mg++ plus 500 μM IBMX. Cells are then detached by tapping on the side of the flask and resuspend in the same buffer. Two thousand cells/well are incubated with 1 μM histamine plus 10 μM forskolin plus various concentrations of compounds in a total volume of 30 μL in 96 well plates for 30 min at 30° C. Final test compound concentrations range from 10-4M to 10-9.5M at full log dilutions. Cyclic AMP levels are measured using HitHunter cAMP kit from Discoverx, cat# 900041 according to manufacturer's instruction. Chemiluminescence signals are detected using Top Count (Packard). Cyclic AMP levels in control cells receiving 10 μM forskolin plus 100 nM histamine are considered 0%, and in cells receiving 10 uM forskolin plus 100 nM histamine plus 1 μM clobenpropit are considered 100%. Data are expressed as % control and analyzed using Prizm software. The Kb values are calculated using the following equation, $KB=EC_{50}$ or $IC_{50}/[1+(ligand/Kd)]$. The data are shown in Table XVIII, below.

TABLE XVIII

| Example Number | H3 Binding Ki (nM) | cAMP Kb (nM) |
| --- | --- | --- |
| 1 | D | B |
| 2 | D | B |
| 3 | E | E |
| 4 | E | — |
| 5 | E | — |
| 6 | D | — |
| 7 | C | — |
| 8 | E | — |
| 9 | B | B |
| 10 | C | — |
| 11 | D | — |
| 12 | D | A |
| 13 | E | B |
| 14 | E | — |
| 15 | E | — |
| 16 | E | — |
| 17 | E | B |
| 18 | E | — |
| 19 | E | — |
| 20 | E | — |
| 21 | E | — |
| 22 | E | A |
| 23 | E | B |
| 24 | E | — |
| 25 | E | A |
| 26 | E | — |
| 27 | E | — |
| 28 | B | — |
| 29 | E | — |
| 30 | — | — |
| 31 | E | — |
| 32 | E | — |
| 33 | E | — |
| 34 | E | — |
| 35 | — | — |
| 36 | E | — |
| 37 | D | — |
| 38 | E | — |
| 39 | E | — |
| 40 | D | — |
| 41 | A | A |
| 42 | E | — |
| 43 | E | — |
| 44 | E | C |
| 45 | E | — |
| 46 | B | A |
| 47 | A | A |
| 48 | B | A |
| 49 | D | A |
| 50 | C | B |
| 51 | E | E |
| 52 | D | A |
| 53 | B | A |
| 54 | B | A |
| 55 | B | — |
| 56 | B | A |
| 57 | C | B |
| 58 | B | A |
| 59 | A | A |
| 60 | C | B |
| 61 | C | A |
| 62 | C | B |
| 63 | B | A |
| 64 | C | B |
| 65 | A | A |
| 66 | B | A |
| 67 | A | — |
| 68 | A | — |
| 69 | C | — |
| 70 | A | B |
| 71 | D | — |
| 72 | C | — |
| 73 | C | — |
| 74 | — | — |
| 75 | A | A |
| 76 | B | — |

TABLE XVIII-continued

| Example Number | H3 Binding Ki (nM) | cAMP Kb (nM) |
|---|---|---|
| 77 | A | A |
| 78 | B | B |
| 79 | A | A |
| 80 | C | — |
| 81 | A | A |
| 82 | A | — |
| 83 | A | — |
| 84 | A | — |
| 85 | A | A |
| 86 | E | — |
| 87 | E | — |
| 88 | E | — |
| 89 | E | — |
| 90 | E | — |
| 91 | A | — |
| 92 | B | — |
| 93 | A | — |
| 94 | E | — |
| 95 | D | — |
| 96 | E | — |
| 97 | E | — |
| 98 | B | — |
| 99 | C | — |
| 100 | D | — |
| 101 | E | — |
| 102 | E | — |
| 103 | A | A |
| 104 | A | — |
| 105 | A | — |
| 106 | A | — |
| 107 | A | — |
| 108 | E | — |
| 109 | A | — |
| 110 | A | — |
| 111 | B | — |
| 112 | A | — |
| 113 | A | — |
| 114 | A | — |
| 115 | A | — |
| 116 | A | — |
| 117 | A | — |
| 118 | E | — |
| 119 | E | — |
| 120 | C | — |
| 121 | D | — |
| 122 | E | — |
| 123 | C | — |
| 124 | E | — |
| 125 | C | B |
| 126 | E | C |
| 127 | B | A |
| 128 | C | A |
| 129 | C | A |
| 130 | D | A |
| 131 | B | A |
| 132 | E | A |
| 133 | B | A |
| 134 | E | A |
| 135 | E | A |
| 136 | A | A |
| 137 | A | A |
| 138 | E | B |
| 139 | — | — |
| 140 | A | A |
| 141 | A | A |
| 142 | A | A |
| 143 | A | — |
| 144 | A | — |
| 145 | A | — |
| 146 | A | — |
| 147 | A | — |
| 148 | A | — |
| 149 | A | — |
| 150 | A | — |
| 151 | A | — |
| 152 | A | — |
| 153 | A | A |
| 154 | A | — |
| 155 | A | A |
| 156 | A | — |
| 157 | A | — |
| 158 | A | — |
| 159 | B | — |
| 160 | E | — |
| 161 | D | — |
| 162 | E | — |
| 163 | E | — |
| 164 | A | A |
| 165 | A | — |
| 166 | A | A |
| 167 | B | — |
| 168 | A | A |
| 169 | B | — |
| 170 | A | — |
| 171 | — | — |
| 172 | A | — |
| 173 | E | — |
| 174 | E | — |
| 175 | E | — |
| 176 | E | — |
| 177 | B | — |
| 178 | A | A |
| 179 | A | — |
| 180 | E | — |
| 181 | B | — |
| 182 | C | — |
| 183 | B | — |
| 184 | A | A |
| 185 | C | — |
| 186 | C | — |
| 187 | A | — |
| 188 | B | — |
| 189 | A | — |
| 190 | A | — |
| 191 | A | — |
| 192 | B | — |
| 193 | B | — |
| 194 | C | — |
| 195 | B | — |
| 196 | B | — |
| 197 | B | — |
| 198 | C | — |
| 199 | A | — |
| 200 | A | — |
| 201 | B | — |
| 202 | A | A |
| 203 | B | — |
| 204 | A | — |
| 205 | B | — |
| 206 | A | — |
| 207 | A | — |
| 212 | B | — |
| 213 | C | — |
| 214 | A | — |
| 215 | C | — |
| 216 | A | — |
| 217 | A | — |
| 218 | A | — |
| 219 | B | — |
| 220 | B | — |
| 221 | C | — |
| 222 | B | — |
| 223 | D | — |
| 224 | A | — |
| 225 | — | — |
| 226 | B | — |
| 227 | E | — |
| 228 | A | — |
| 229 | B | — |
| 230 | E | — |
| 231 | A | — |
| 232 | C | — |

TABLE XVIII-continued

| Example Number | H3 Binding Ki (nM) | cAMP Kb (nM) |
|---|---|---|
| 233 | C | |
| 234 | B | |

What is claimed is:

1. A compound of formula I

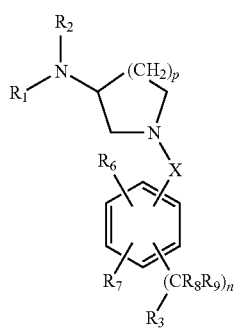

(I)

wherein
X is CO, $CH_2$ or $SO_m$;
p and n are each independently an integer of 1, 2 or 3;
m is 2;
$R_1$ and $R_2$ are each independently H or an optionally substituted alkyl group or $R_1$ and $R_2$ may be taken together with the atom to which they are attached to form an optionally substituted 4- to 7-membered ring optionally containing one or two additional heteroatoms selected from N, O or S;
$R_3$ is a benzimidazolyl, imidazolyl, indazolyl or indolyl group, each group being optionally substituted;
$R_6$ and $R_7$ are each independently H, halogen, $OR_{10}$ or an alkyl, alkenyl, alkynyl, cycloalkyl, cycloheteroalkyl, aryl or heteroaryl group each group being optionally substituted;
$R_8$ and $R_9$ are each independently H, or an alkyl, cycloalkyl, or aryl group each group being optionally substituted; and
$R_{10}$ is H or an optionally substituted alkyl group; or
a stereoisomer thereof or a pharmaceutically acceptable salt thereof.

2. The compound according to claim 1 wherein X is CO or $CH_2$.

3. The compound according to claim 1 wherein n is 1 and p is 1 or 2.

4. The compound according to claim 1 wherein $R_8$ and $R_9$ are each independently H or methyl.

5. The compound according to claim 2 wherein $R_1$ and $R_2$ are taken together with the atom to which they are attached to form a 5-membered ring.

6. The compound according to claim 2 wherein $R_3$ is benzimidazolyl.

7. The compound according to claim 3 wherein X is CO or $CH_2$ and $R_1$ and $R_2$ are taken together with the atom to which they are attached to form a 5-membered ring.

8. The compound according to claim 7 wherein $R_3$ is an optionally substituted benzimidazole ring attached at the 2-position of said benzimidazole ring.

9. The compound according to claim 1 selected from:
N,N-Dimethyl-1-{4-[(2-phenyl-1H-benzimidazol-1-yl)methyl]-benzoyl}pyrrolidin-3-ylamine;
(3-S)—N,N-Dimethyl-1-{4-[(2-phenyl-1H-benzimidazol-1-yl)methyl]-benzoyl}pyrrolidin-3-ylamine;
(3-R)—N,N-Dimethyl-1-{4-[(2-phenyl-1H-benzimidazol-1-yl)methyl]-benzoyl}pyrrolidin-3-ylamine;
N,N-Dimethyl-1-{4-[(6-fluoro-1H-benzimidazol-1-yl)methyl]-benzoyl}pyrrolidin-3-ylamine;
N,N-Dimethyl-1-{4-[(6-methyl-1H-benzimidazol-1-yl)methyl]-benzoyl}pyrrolidin-3-ylamine;
N,N-Dimethyl-1-{4-[(5-fluoro-1H-benzimidazol-1-yl)methyl]-benzoyl}pyrrolidin-3-ylamine;
N,N-Dimethyl-1-{4-[(4-fluoro-1H-benzimidazol-1-yl)methyl]-benzoyl}pyrrolidin-3-ylamine;
N,N-Dimethyl-1-[3-(1H-benzimidazol-1-yl)methyl]-benzoyl}pyrrolidin-3-ylamine;
N,N-Dimethyl1-[4-(1H-indol-1-ylmethyl)benzoyl]pyrrolidin-3-ylamine;
N,N-Dimethyl1-{[4-(2-methyl-1H-indol-1-yl)methyl]benzoyl}pyrrolidin-3-ylamine;
N,N-Dimethyl1-{[4-(2-phenyl-1H-indol-1-yl)methyl]benzoyl}pyrrolidin-3-ylamine;
N,N-Dimethyl1-{[4-(5-methoxy-1H-indol-1-yl)methyl]benzoyl}pyrrolidin-3-ylamine;
N,N-Dimethyl1-{[4-(5-methoxy-2-phenyl-1H-indol-1-yl)methyl]benzoyl}pyrrolidin-3-ylamine;
N,N-Dimethyl1-{[4-(7-aza-1H-indol-1-yl)methyl]benzoyl}pyrrolidin-3-ylamine;
N,N-Dimethyl1-{[4-(1H-benzo[d]imidazol-1-yl)methyl]benzoyl}pyrrolidin-3-ylamine;
N,N-Dimethyl1-{[4-(2-methyl-1H-benzo[d]imidazol-1-yl)methyl]benzoyl}pyrrolidin-3-ylamine;
N,N-Dimethyl1-{[4-(5-hydroxy-1H-indol-1-yl)methyl]benzoyl}pyrrolidin-3-ylamine;
N,N-Dimethyl1-{[4-(5-fluoro-1H-indol-1-yl)methyl]benzoyl}pyrrolidin-3-ylamine;
N,N-Dimethyl1-{[4-(3-cyano-1H-indol-1-yl)methyl]benzoyl}pyrrolidin-3-ylamine;
N,N-Dimethyl1-{[4-(2-phenyl-1H-imidazol-1-yl)methyl]benzoyl}pyrrolidin-3-ylamine;
1'-{4-[(2-Phenyl-1H-benzimidazol-1-yl)methyl]benzoyl}-1,3'-bipyrrolidine;
1'-{4-[(5-Chloro-2-methyl-1H-benzimidazol-1-yl)methyl]benzoyl}-1,3'-bipyrrolidine;
1'-{4-[(6-Chloro-2-methyl-1H-benzimidazol-1-yl)methyl]benzoyl}-1,3'-bipyrrolidine;
1'-{4-[(6-Methyl-1H-benzimidazol-1-yl)methyl]benzoyl}-1,3'-bipyrrolidine;
1'-{4-[(5-Fluoro-1H-benzimidazol-1-yl)methyl]benzoyl}-1,3'-bipyrrolidine;
(2-R)-1'-[4-(1H-Benzimidazol-1-ylmethyl)benzoyl]-2-methyl-1,3'-bipyrrolidine;
(3'-R)-1'-{4-[(2-Methyl-1H-benzimidazol-1-yl)methyl]benzoyl}-1,3'-bipyrrolidine;
(3'-S)-1'-{4-[(2-Methyl-1H-benzimidazol-1-yl)methyl]benzoyl}-1,3'-bipyrrolidine;
(3'S)-[4-(1H-Indol-1-ylmethyl)benzoyl]-1,3'-bipyrrolidine;
(3'S)-[4-(1H-Indazol-1-ylmethyl)benzoyl]-1,3'-bipyrrolidine;

(3'S)-1'-{4-[(5-Chloro-2-methyl-1H-benzimidazol-1-yl)methyl]benzoyl}-1,3'-bipyrrolidine;
(3'S)-1'-{4-[(6-Chloro-2-methyl-1H-benzimidazol-1-yl)methyl]benzoyl}-1,3'-bipyrrolidine;
(3'S)-1'-{4-[(6-Fluoro-1H-benzimidazol-1-yl)methyl]benzoyl}-1,3'-bipyrrolidine;
(3'S)-1'-{4-[(6-Fluoro-1H-benzimidazol-1-yl)methyl]benzyl}-1,3'-bipyrrolidine;
(3'S)-1'-{4-[(5-Fluoro-1H-benzimidazol-1-yl)methyl]benzyl}-1,3'-bipyrrolidine;
(3'S)-1'-{4-[(5-Fluoro-1H-benzimidazol-1-yl)methyl]benzoyl}-1,3'-bipyrrolidine;
(3'S)-1'-{4-[(7-Chloro-1H-indol-1-yl)methyl]benzoyl}-1,3'-bipyrrolidine;
(3'-S)-1'-{4-[(1S)-1-(2-Methyl-1H-benzimidazol-1-yl)ethyl]benzoyl}-1,3'-bipyrrolidine;
(3'-S)-1'-{4-[(1R)-1-(2-Methyl-1H-benzimidazol-1-yl)ethyl]benzoyl}-1,3'-bipyrrolidine;
(3'-S)-1'-[4-(1H-Benzimidazol-1-ylmethyl)benzyl]-1,3'-bipyrrolidine;
(3'-S)-1'-[4-(1H-Benzimidazol-1-ylmethyl)benzoyl]-1,3'-bipyrrolidine;
N,N-Dimethyl-1-{4-[(2-phenyl-1H-benzimidazol-1-yl)methyl]-benzyl}pyrrolidin-3-ylamine;
(3-S)-N,N-Dimethyl-1-{4-[(2-phenyl-1H-benzimidazol-1-yl)methyl]-benzyl}pyrrolidin-3-ylamine;
(3-R)-N,N-Dimethyl-1-{4-[(2-phenyl-1H-benzimidazol-1-yl)methyl]-benzyl}pyrrolidin-3-ylamine;
N,N-Dimethyl-1-{4-[(6-fluoro-1H-benzimidazol-1-yl)methyl]-benzyl}pyrrolidin-3-ylamine;
N,N-Dimethyl-1-{4-[(6-methyl-1H-benzimidazol-1-yl)methyl]-benzyl}pyrrolidin-3-ylamine;
N,N-Dimethyl-1-{4-[(5-fluoro-1H-benzimidazol-1-yl)methyl]-benzyl}pyrrolidin-3-ylamine;
N,N-Dimethyl-1-{4-[(4-fluoro-1H-benzimidazol-1-yl)methyl]-benzyl}pyrrolidin-3-ylamine;
N,N-Dimethyl-1-[3-(1H-benzimidazol-1-yl)methyl]-benzyl}pyrrolidin-3-ylamine;
N,N-Dimethyl1-[4-(1H-indol-1-ylmethyl)benzyl]pyrrolidin-3-ylamine;
(3'S)-1'-[4-(1H-indol-3-ylmethyl)benzoyl]-1,3'-bipyrrolidine;
(3'S)-1'-{4-[(1-methyl-1H-indol-3-yl)methyl]benzoyl}-1,3'-bipyrrolidine;
(3S)-N,N-dimethyl-1-{4-[(1-methyl-1H-indol-3-yl)methyl]benzoyl}pyrrolidin-3-amine;
2-{4-[(3-piperidin-1-ylpyrrolidin-1-yl)carbonyl]benzyl}-1H-benzimidazole;
1'-{4-[(1-ethyl-1H-benzimidazol-2-yl)methyl]benzoyl}-1,3'-bipyrrolidine;
1'-{4-[(1-methyl-1H-benzimidazol-2-yl)methyl]benzoyl}-1,3'-bipyrrolidine;
1-methyl-2-{4-[(3-piperidin-1-ylpyrrolidin-1-yl)carbonyl]benzyl}-1H-benzimidazole;
1'-[4-(1H-benzimidazol-2-ylmethyl)benzoyl]-1,3'-bipyrrolidine;
(3'S)-1'-{4-[(1-propyl-1H-benzimidazol-2-yl)methyl]benzoyl}-1,3'-bipyrrolidine;
(3'S)-1'-{4-[(1-isopropyl-1H-benzimidazol-2-yl)methyl]benzoyl}-1,3'-bipyrrolidine;
(3'S)-1'-{4-[(1-isobutyl-1H-benzimidazol-2-yl)methyl]benzoyl}-1,3'-bipyrrolidine;
(3'S)-1'-(4-{[1-(cyclopropylmethyl)-1H-benzimidazol-2-yl]methyl}benzoyl)-1,3'-bipyrrolidine;
(3'S)-1'-(4-{[1-(phenylsulfonyl)-1H-benzimidazol-2-yl]methyl}benzoyl)-1,3'-bipyrrolidine;
(3'S)-1'-(4-{[1-(2-methoxyethyl)-1H-benzimidazol-2-yl]methyl}benzoyl)-1,3'-bipyrrolidine;
2-(2-{4-[(3'S)-1,3'-bipyrrolidin-1'-ylcarbonyl]benzyl}-1H-benzimidazol-1-yl)ethanol;
(3'S)-1'-{4-[(1-ethyl-1H-benzimidazol-2-yl)methyl]benzoyl}-1,3'-bipyrrolidine;
(3'S)-1'-(4-{[1-(2-phenylethyl)-1H-benzimidazol-2-yl]methyl}benzoyl)-1,3'-bipyrrolidine;
(3'S)-1'-{4-[(1-ethyl-1H-benzimidazol-2-yl)methyl]benzyl}-1,3'-bipyrrolidine;
(3'S)-1'-{4-[(1-phenyl-1H-benzimidazol-2-yl)methyl]benzoyl}-1,3'-bipyrrolidine;
5-methyl-1-{4-[(3-piperidin-1-ylpyrrolidin-1-yl)carbonyl]benzyl}-1H-benzimidazole;
4-fluoro-1-{4-[(3-piperidin-1-ylpyrrolidin-1-yl)methyl]benzyl}-1H-benzimidazole;
1'-[4-(1H-benzimidazol-1-ylmethyl)-3-chlorobenzyl]-1,3'-bipyrrolidine;
1-{4-[(4-fluoro-1H-benzimidazol-1-yl)methyl]benzyl}-N,N-dimethylpyrrolidin-3-amine;
5-methyl-1-(4-{[3-(2-methylpiperidin-1-yl)pyrrolidin-1-yl]carbonyl}benzyl)-1H-benzimidazole;
5-methyl-1-{4-[(3-morpholin-4-ylpyrrolidin-1-yl)carbonyl]benzyl}-1H-benzimidazole;
5-methyl-1-(4-{[3-(4-methylpiperidin-1-yl)pyrrolidin-1-yl]carbonyl}benzyl)-1H-benzimidazole;
5-methyl-1-(4-{[3-(4-methylpiperazin-1-yl)pyrrolidin-1-yl]carbonyl}benzyl)-1H-benzimidazole;
5-methyl-1-(4-{[3-(3-methylpiperidin-1-yl)pyrrolidin-1-yl]carbonyl}benzyl)-1H-benzimidazole;
((2S)-1'-{4-[5-methyl-1H-benzimidazol-1-yl)methyl]benzoyl}-1,3'-bipyrrolidin-2-yl)methanol;
N,N-dimethyl-1-{4-[(5-methyl-1H-benzimidazol-1-yl)methyl]benzoyl}pyrrolidin-3-amine;
N-ethyl-N-methyl-1-{4-[(5-methyl-1H-benzimidazol-1-yl)methyl]benzoyl}pyrrolidin-3-amine;
1-{2-chloro-4-[(3-piperidin-1-ylpyrrolidin-1-yl)methyl]benzyl}-1H-benzimidazole;
1-[4-(1H-benzimidazol-1-ylmethyl)-2-methozybenzoyl]-N,N-dimethylpyrrolidin-3-amine;
1-[4-(1H-benzimidazol-1-ylmethyl)-3-chlorobenzyl]-N-ethyl-N-methylpyrrolidin-3-amine;
(2R)-1'-[4-(1H-benzimidazol-1-ylmethyl)-2-methozybenzoyl]-2-methyl-1,3'-bipyrrolidine;
2-benzyl-1'-{4-[(5-methyl-1H-benzimidazol-1-yl)methyl]benzoyl}-1,3'-bipyrrolidine;
1'-{4-[(7-methyl-1H-benzimidazol-1-yl)methyl]benzoyl}-1,3'-bipyrrolidine;
(2R)-1'-{4-[(5-fluoro-1H-benzimidazol-1-yl)methyl]benzoyl}-2-methyl-1,3'-bipyrrolidine;
(2R)-2-methyl-1'-{4-[(5-methyl-1H-benzimidazol-1-yl)methyl]benzoyl}-1,3'-bipyrrolidine;
1-[4-(1H-benzimidazol-1-ylmethyl)-3-chlorobenzyl]-N,N-dimethylpyrrolidin-3-amine;
(2S)-1'-{4-[(5-fluoro-1H-benzimidazol-1-yl)methyl]benzoyl}-2-methyl-1,3'-bipyrrolidine;

1-{4-[(3-azepan-1-ylpyrrolidin-1-yl)carbonyl]benzyl}-5-methyl-1H-benzimidazole;

5-methyl-1-(4-{[3-(4-methyl-1,4-diazepan-1-yl)pyrrolidin-1-yl]carbonyl}benzyl)-1H-benzimidazole;

(3'S)-1'-{4-[(5-fluoro-1H-benzimidazol-1-yl)methyl]benzoyl}-1,3'-bipyrrolidine;

(3'S)-1'-{4-[(5-fluoro-1H-benzimidazol-1-yl)methyl]benzyl}-1,3'-bipyrrolidine;

7-methyl-1-{4-[(3-piperidin-1-ylpyrrolidin-1-yl)carbonyl]benzyl}-1H-benzimidazole;

(2R)-1'-{4-[(5-fluoro-1H-benzimidazol-1-yl)methyl]benzyl}-2-methyl-1,3'-bipyrrolidine;

1-{4-[(3-azetidin-1-ylpyrrolidin-1-yl)carbonyl]benzyl}-5-methyl-1H-benzimidazole;

1'-[4-(1H-benzimidazol-1-ylmethyl)-2-fluorobenzoyl]-1,3'-bipyrrolidine;

(3'S)-1'-{4-[(7-fluoro-1H-benzimidazol-1-yl)methyl]benzoyl}-1,3'-bipyrrolidine;

1-(4-{[(3S)-3-azepan-1-ylpyrrolidin-1-yl]carbonyl}benzyl)-7-fluoro-1H-benzimidazole;

7-fluoro-1-(4-{[(3S)-3-piperidin-1-ylpyrrolidin-1-yl]carbonyl}benzyl)-1H-benzimidazole;

(3S)-N-ethyl-1-{4-[(7-fluoro-1H-benzimidazol-1-yl)methyl]benzoyl}-N-methylpyrrolidin-3-amine;

7-fluoro-1-(4-{[(3S)-3-(3-methylpiperidin-1-yl)pyrrolidin-1-yl]carbonyl}benzyl)-1H-benzimidazole;

1-(4-{[(3S)-3-azetidin-1-ylpyrrolidin-1-yl]carbonyl}benzyl)-7-fluoro-1H-benzimidazole;

(3'S)-1'-(4-{[2-(trifluoromethyl)-1H-benzimidazol-1-yl]methyl}benzoyl)-1,3'-bipyrrolidine;

(3'S)-1'-{4-[1-(7-chloro-1H-indol-1-yl)ethyl]benzoyl}-1,3'-bipyrrolidine;

(3'S)-1'-{4-[1-(5-chloro-2-methyl-1H-benzimidazol-1-yl)ethyl]benzoyl}-1,3'-bipyrrolidine;

(3'S)-1'-{4-[(1S)-1-(1H-benzimidazol-1-yl)ethyl]benzoyl}-1,3'-bipyrrolidine;

(3'S)-1'-{4-[(1R)-1-(1H-benzimidazol-1-yl)ethyl]benzoyl}-1,3'-bipyrrolidine;

(3'S)-1'-{4-[(5-chloro-2-methyl-1H-benzimidazol-1-yl)methyl]benzoyl}-1,3'-bipyrrolidine;

(3'S)-1'-{4-[(6-chloro-2-methyl-1H-benzimidazol-1-yl)methyl]benzoyl}-1,3'-bipyrrolidine;

(3'S)-1'-{4-[(1S)-1-(5-chloro-2-methyl-1H-benzimidazol-1-yl)ethyl]benzoyl)-1,3'-bipyrrolidine;

(3'S)-1'-{4-[(1S)-1-(6-chloro-2-methyl-1H-benzimidazol-1-yl)ethyl]benzoyl}-1,3'-bipyrrolidine;

(3'S)-1'-{4-[(1R)-1-(5-chloro-2-methyl-1H-benzimidazol-1-yl)ethyl]benzoyl}-1,3'-bipyrrolidine;

(3'S)-1'-{4-[(1R)-1-(6-chloro-2-methyl-1H-benzimidazol-1-yl)ethyl]benzoyl}-1,3'-bipyrrolidine;

(3S)-1-{4-[(1R)-1-(6-chloro-2-methyl-1H-benzimidazol-1-yl)ethyl]benzoyl}pyrrolidine-3-amine;

(3S)-1-{4-[(1R)-1-(5-chloro-2-methyl-1H-benzimidazol-1-yl)ethyl]benzoyl}pyrrolidine-3-amine;

(3'S)-1'-{4-[(5-chloro-1H-benzimidazol-1-yl)methyl]benzoyl}-1,3'-bipyrrolidine;

(3'S)-1'-{4-[(6-chloro-1H-benzimidazol-1-yl)methyl]benzoyl}-1,3'-bipyrrolidine;

(3S)-1-{4-[(5-chloro-1H-benzimidazol-1-yl)methyl]benzoyl}pyrrolidin-3-amine;

(3S)-1-{4-[(1S)-1-(6-chloro-2-methyl-1H-benzimidazol-1-yl)ethyl]benzoyl}pyrrolidin-3-amine;

(3S)-1-{4-[(1S)-1-(5-chloro-2-methyl-1H-benzimidazol-1-yl)ethyl]benzoyl}pyrrolidine-3-amine;

(3'S)-1'-{4-[1-(5-chloro-1H-indol-1-yl)ethyl]benzoyl}-1,3'-bipyrrolidine;

1-(1-{4-[(3'S)-1,3'-bipyrrolidin-1'-ylcarbonyl]phenyl}ethyl)-1H-indole-5-carbonitrile;

2-methyl-1-[1-(4-{[1R,4R)-5-methyl-2,5-diazabicyclo[2.2.1]hept-2-yl]carbonyl}phenyl)-1H-benzimidazole;

1-{4-[(3-pyrrolidin-1-ylpiperidin-1-yl)carbonyl]benzyl}-1H-benzimidazole;

1'-[4-(1H-benzimidazol-1-ylmethyl)benzoyl]-1,3'-bipiperidine;

1-(4-{[3-(2-methylpyrrolidin-1-yl)piperidin-1-yl]carbonyl}benzyl)-1H-benzimidazole;

4-(1H-benzimidazol-1-ylmethyl)-N-(2-pyrrolidin-1-ylethyl)benzamide;

4-[(2-methyl-1H-benzimidazol-1-yl)methyl]-N-(2-pyrrolidin-1-ylethyl)benzamide;

1-(4-{[3-(4-methylpiperidin-1-yl)pyrrolidin-1-yl]carbonyl}benzyl)-1H-benzimidazole;

(2R,3'R)-1'-[4-(1H-benzimidazol-1-ylmethyl)benzoyl]-2-methyl-1,3'-bipyrrolidine and;

(2S,3'R)-1'-[4-(1H-benzimidazol-1-ylmethyl)benzoyl]-2-methyl-1,3'-bipyrrolidine; or a stereoisomer thereof; or a pharmaceutically acceptable salt thereof.

10. A pharmaceutical composition which comprises a pharmaceutically acceptable carrier and an effective amount of a compound of claim 1, a stereoisomer thereof or a pharmaceutically acceptable salt thereof 11. A process for the preparation of a compound of formula I

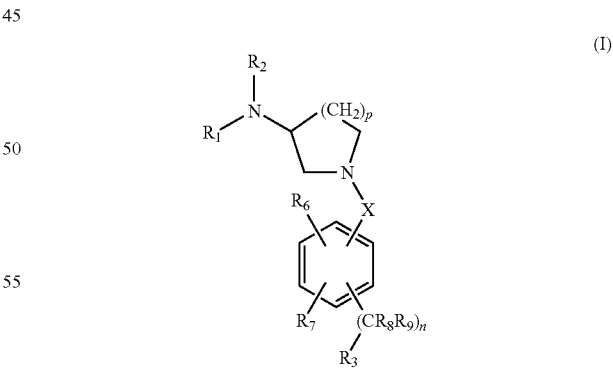

wherein

X is CO, $CH_2$ or $SO_m$;

p and n are each independently an integer of 1, 2 or 3;

m is 0 or an integer of 1 or 2;

$R_1$ and $R_2$ are each independently H or an optionally substituted alkyl group or $R_1$ and $R_2$ may be taken together with the atom to which they are attached to form an optionally substituted 4- to 7-membered ring optionally containing one or two additional heteroatoms selected from N, O or S $R_3$ is a benzimidazolyl, imidazolyl, indazolyl or indolyl group each group being optionally substituted;

$R_4$ and $R_5$ are taken together with the atom to which they are attached to form an optionally substituted fused bicyclic, tricyclic or tetracyclic 9- to 15-membered ring system optionally containing one to three additional heteroatoms selected from N, O or S;

$R_6$ and $R_7$ are each independently H, halogen, $OR_{10}$ or an alkyl, alkenyl, alkynyl, cycloalkyl, cycloheteroalkyl, aryl or heteroaryl group each optionally substituted;

$R_8$ and $R_9$ are each independently H, or an alkyl, cycloalkyl, or aryl group each optionally substituted; and $R_{10}$ is H or an optionally substituted alkyl group
which process comprises reacting a compound of formula XVI

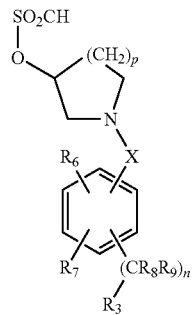

wherein X, n, p, $R_3$, $R_6$, $R_7$, $R_8$ and $R_9$ are as described hereinabove with an amine, $HNR_1R_2$, wherein $R_1$ and $R_2$ are as described hereinabove in the presence of microwave irradiation, optionally in the presence of a solvent.

* * * * *